US012629094B2

(12) United States Patent
Seeley et al.

(10) Patent No.: US 12,629,094 B2
(45) Date of Patent: May 19, 2026

(54) SYSTEM, SOFTWARE AND METHODS OF USING SOFTWARE FOR PREDICTING EFFICACY OF ALZHEIMER'S DISEASE TREATMENTS

(71) Applicants: THE REGENTS OF THE UNIVERSITY OF CALIFORNIA, Oakland, CA (US); KOREA UNIVERSITY RESEARCH AND BUSINESS FOUNDATION, Seoul (KR)

(72) Inventors: William W. Seeley, San Francisco, CA (US); Joon-Kyung Seong, Seoul (KR); Whajin Lee, Seoul (KR); Jesse Aaron Brown, Mill Valley, CA (US)

(73) Assignees: THE REGENTS OF THE UNIVERSITY OF CALIFORNIA, Oakland, CA (US); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 328 days.

(21) Appl. No.: 18/029,653

(22) PCT Filed: Sep. 30, 2021

(86) PCT No.: PCT/US2021/053031
§ 371 (c)(1),
(2) Date: Mar. 30, 2023

(87) PCT Pub. No.: WO2022/072738
PCT Pub. Date: Apr. 7, 2022

(65) Prior Publication Data
US 2024/0225538 A1 Jul. 11, 2024

Related U.S. Application Data

(60) Provisional application No. 63/085,749, filed on Sep. 30, 2020.

(51) Int. Cl.
A61B 5/00 (2006.01)
A61B 6/03 (2006.01)
G16H 30/40 (2018.01)

(52) U.S. Cl.
CPC .......... *A61B 5/4848* (2013.01); *A61B 5/0042* (2013.01); *A61B 6/037* (2013.01); *G16H 30/40* (2018.01)

(58) Field of Classification Search
CPC .................................................... A61B 5/4848
See application file for complete search history.

(56) References Cited

U.S. PATENT DOCUMENTS

| | | |
|---|---|---|
| 2011/0086776 A1 | 4/2011 | Jarrige-Le Prado et al. |
| 2017/0042476 A1 | 2/2017 | Reiman et al. |
| 2017/0112820 A1 | 4/2017 | Elenko et al. |

OTHER PUBLICATIONS

Sepulcre Jorge et al: "Tau and amyloid 1-16 [beta] proteins distinctively associate to functional network changes in the aging brain", Alzheimer's & Dementia, vol. 13, No. 11, Mar. 30, 2017 (Mar. 30, 2017), pp. 1261-1269.
(Continued)

*Primary Examiner* — Joseph M Santos Rodriguez
(74) *Attorney, Agent, or Firm* — John A. Zurawski; The Belles Group, P.C.

(57) ABSTRACT

The disclosure relates to a system comprising software that predicts responsiveness of healthy subjects or subjects at risk for or suffering from Alzheimer's Disease to certain disease modifying drugs. Embodiments of the disclosure include methods comprising analyzing images of the brain for depositions of amyloid-beta (Aβ) protein and tau protein, and correlating protein deposition levels to drug responsiveness.

22 Claims, 23 Drawing Sheets

Specification includes a Sequence Listing.

(56)　　　　　　References Cited

OTHER PUBLICATIONS

Matsuda Hiroshi et al: "Neuroimaging of 1-16 Alzheimer's disease: focus on amyloid and tau PET", Japanese Journal of Radiology, Springer Japan, Tokyo, vol. 37, No. 11, Sep. 6, 2019 {Sep. 6, 2019), pp. 735-749.
Leuzy Antoine et al: "Tau PET imaging in 1-16 neurodegenerative tauopathies-still a challenge", Molecular Psychiatry, Nature Publishing Group UK, London, vol. 24, No. 8, Jan. 11, 2019 (Jan. 11, 2019), pp. 1112-1134.

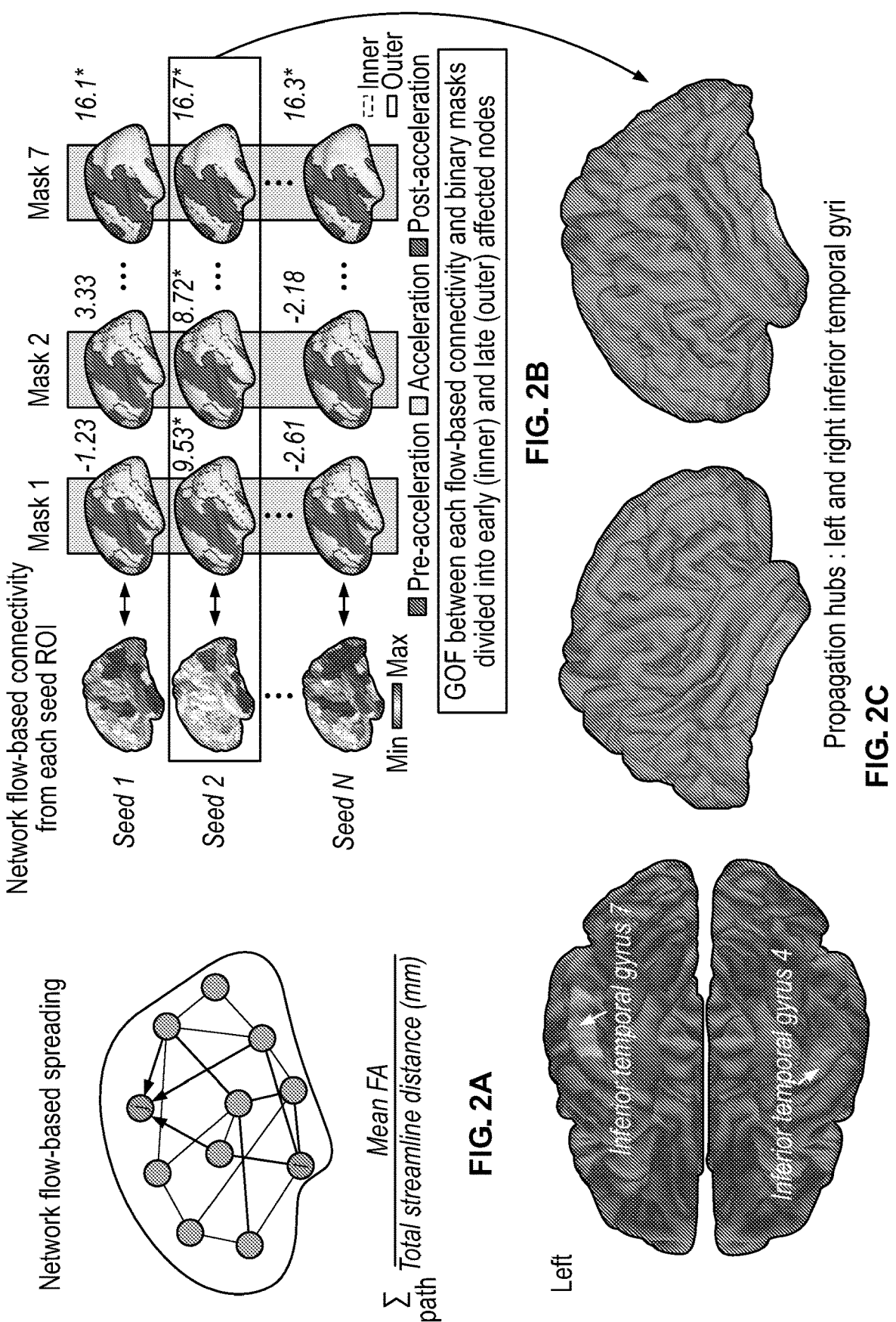

Network flow-based connectivity from each seed ROI

Mask 1    Mask 2    ...    Mask 7

Seed 1    -1.23    3.33    ...    16.1*

Seed 2    9.53*    8.72*    ...    16.7*

Seed N    -2.61    -2.18    ...    16.3*

Min ▬▬ Max

■ Pre-acceleration  □ Acceleration  ▨ Post-acceleration

GOF between each flow-based connectivity and binary masks
divided into early (inner) and late (outer) affected nodes ▦ Inner  □ Outer

FIG. 2B

Network flow-based spreading $$\alpha \sum_{path} \frac{\overline{Mean\ FA}}{Total\ streamline\ distance\ (mm)}$$

FIG. 2A

Left

Inferior temporal gyrus 1    Inferior temporal gyrus 4

Propagation hubs : left and right inferior temporal gyri

Remote Aβ-tau interaction pseudo-order (right)

EC (1st)    ITG (4th)

0.3   1

Local Aβ-tau interaction pseudo-order (right)

EC (19th)    ITG (3rd)

0.3   1

Remote Aβ-tau

Right EC

T-statistics

Frequency

Local Aβ-tau

RightITG

T-statistics

**Remote Aβ-*PRNP→FYN*-tau**

Right EC

T-statistics

Frequency

**Local Aβ-*PRNP-FYN*-tau**

Right ITG

T-statistics

FIG. 12C (Cont..)

Mask 1    Mask 2    Mask 3    Mask 4

Mask 5    Mask 6    Mask 7

▣ Inner mask
☐ Outer mask

SYSTEM, SOFTWARE AND METHODS OF USING SOFTWARE FOR PREDICTING EFFICACY OF ALZHEIMER'S DISEASE TREATMENTS

CROSS-REFERENCE TO RELATED APPLICATIONS

This application is a national phase application filed under 35 U.S.C. § 371 of International Application No. PCT/US2021/053031, filed Sep. 23, 2021, which claims priority to U.S. Provisional Application No. 63/085,749 filed on Sep. 30, 2021, both of which are incorporated by reference herein in its their entireties.

REFERENCE TO AN ELECTRONIC SEQUENCE LISTING

The contents of the electronic sequence listing (UCAL-017-US_SequenceListing_ST25.txt; size: 13,656 bytes; and date of creation: Oct. 10, 2023) is herein incorporated by reference in its entirety.

FIELD OF INVENTION

The disclosure relates to a system comprising computer program product or software that predicts responsiveness of healthy subjects or subjects at risk for or suffering from Alzheimer's Disease to certain disease modifying drugs. Embodiments of the disclosure include methods comprising analyzing images of the brain for depositions of amyloid-beta (Aβ) protein and tau protein, and correlating protein deposition levels to drug responsiveness.

BACKGROUND

Alzheimer's disease ("AD") is a progressive disease of the human central nervous system. AD manifests in gradual loss of memory, language, calculation, and visual-spatial skills, as well as psychiatric and other cognitive symptoms that reflect the pattern of regional neurodegeneration.

Parenchymal Aβ protein deposition and hyperphosporylated tau neurofibrillary tangle formation are the defining neuropathological features of Alzheimer's disease.[1,2,4] Aβ has been proposed to trigger tau spreading,[1,2] but the spatial incongruity of Aβ and tau during early AD has cast doubt on this hypothesis.[2] Aβ protein deposition begins in heteromodal association neocortices,[5] but the earliest forebrain neurofibrillary tangles emerge within the lateral entorhinal cortex.[6] Despite being the key molecules in the pathogenesis of AD, how Aβ protein deposition and tau protein deposition interact to promote AD remains unclear.[1,2]

SUMMARY OF EMBODIMENTS

Recently developed brain imaging tools have enabled researchers to estimate the brain structural connectome[3] and to quantify regional Aβ and tau deposition in living humans,[2] making it possible to study network-based Aβ-tau interactions. In the present disclosure, two Aβ-tau interactions involved in the onset and propagation of tau spreading in AD were identified. First, it is shown that the lateral entorhinal cortex, an early site of tau neurofibrillary tangle formation, is the brain region most strongly connected to distant neocortical regions that accumulate Aβ during pre-symptomatic and early prodromal AD. Second, it is identified that the inferior temporal gyrus is the region featuring the greatest local amyloid-tau interactions and the structural connections best suited to facilitate exponential tau propagation during late prodromal AD.

The present disclosure therefore relates to a method of identifying a subject likely to respond to an Alzheimer's disease (AD) treatment comprising: (a) imaging a brain of the subject; (b) analyzing Aβ protein deposition in at least one region within the brain of the subject; (c) analyzing tau protein deposition in at least one region within the brain of the subject; and (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject.

The disclosure further relates to a method of identifying a subject responsive to an Alzheimer's disease (AD) treatment comprising: (a) imaging a brain of the subject; (b) analyzing amyloid-beta (Aβ) protein deposition in at least one region within the brain of the subject; (c) analyzing tau protein deposition in at least one region within the brain of the subject; and (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject.

The disclosure also relates to a method of predicting a likelihood of a subject or population of subjects does or does not respond to an Aβ modulating agent comprising: (a) imaging a brain of the subject; (b) analyzing amyloid-beta (Aβ) protein deposition in at least one region within the brain of the subject; (c) analyzing tau protein deposition in at least one region within the brain of the subject; and (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject.

The disclosure additionally relates to a method predicting a pathological prognosis and/or a clinical outcome of a subject or population of subjects suffering from Alzheimer's Disease comprising: (a) imaging a brain of the subject; (b) analyzing amyloid-beta (Aβ) protein deposition in at least one region within the brain of the subject; (c) analyzing tau protein deposition in at least one region within the brain of the subject; and (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject.

The disclosure further relates to a method of selecting or optimizing an AD therapy in a subject or population of subjects, the method comprising: (a) imaging a brain of the subject; (b) analyzing amyloid-beta (Aβ) protein deposition in at least one region within the brain of the subject; (c) analyzing tau protein deposition in at least one region within the brain of the subject; and (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject.

In some embodiments, the first normalized and second normalized scores in any of the disclosed method correspond to analysis performed using a plurality of regions of the brain of the subject. In some embodiments, any of the disclosed methods further comprises a step of calculating a first threshold relative to a first control dataset and calculating a second threshold relative to a second control dataset. In some embodiments, any of the disclosed methods further comprises: (e) comparing the first normalized score to a first threshold and comparing a second normalized score to a second threshold; and (f) classifying the subject as being likely to respond to an AD treatment based upon results of comparing of step (e) relative to the first and/or second threshold, wherein each of steps (e) and (f) are performed after step (d), and wherein the first threshold is calculated relative to a first control dataset and the second threshold is calculated relative to a second control dataset.

In some embodiments, the analyzing step (b) of any of the disclosed methods comprises: (i) determining an absence, presence or quantity of Aβ protein deposition within one or a plurality of regions of the brain of the subject, wherein step (i) is performed prior to step (e), and wherein the normalized score of step (d) is based upon step (i). In some embodiments, the analyzing step (c) of any of the disclosed methods comprises: (ii) determining an absence, presence or quantity of tau protein deposition within one or a plurality of regions of the brain of a subject, wherein step (ii) is performed prior to step (e), and wherein the normalized score of step (d) is based upon step (ii).

In some embodiments, the step of imaging the brain in any of the disclosed methods is performed through a positron emission tomography (PET) scan. In some embodiments, the step of analyzing the Aβ protein deposition and/or tau protein deposition is performed through analysis of one or a plurality of PET scan images. In some embodiments, the step of calculating the first normalized score in any of the disclosed methods comprises comparing the interaction of tau protein deposition in at least one first region of interest of the brain as compared to Aβ protein deposition in one or a plurality of regions of the brain outside of the first region of interest, and the step of calculating the second normalized score in any of the disclosed methods comprises comparing Aβ protein deposition and tau protein deposition in at least one second region of interest of the brain of the subject.

In some embodiments, the first normalized score of any of the disclosed methods is calculated by the following formula:

$$\left(\sum_j \delta_{ij} \cdot A\beta\,SUVR_j\right) \times \left(Tau\ W\text{–score}_i\right)$$

wherein $\sum_j \delta_{ij}$ is the structural or functional connectivity between the first region of interest, region i, and the one or plurality of regions, denoted here as region(s) j, of the brain outside of the first region of interest; wherein $SUVR_j$ is a first standardized uptake value ratio (SUVR) corresponding to the Aβ protein deposition in the one or plurality of regions, denoted here as region(s) j, of the brain outside of the first region of interest, wherein Tau W-score$_i$ is a first standardized value corresponding to the tau protein deposition in the first region of interest of the brain, the first standardized value being calculated based on a control population of subjects, wherein the second normalized score is calculated by the following formula:

$$(A\beta\ SUVR_k) \times \left(Tau\ W\text{–score}_k\right)$$

wherein $SUVR_k$ is a second SUVR corresponding to the Aβ protein deposition in the second region of interest of the brain, denoted here as region k, and wherein Tau W-score$_k$ is a second standardized value corresponding to the tau protein deposition in the second region of interest of the brain, denoted here as k, the second standardized value being calculated based on the control population of subjects.

In some embodiments, the first threshold used in any of the disclosed methods is from about 1 to about 10 in each cerebral hemisphere and is determined by the following formula:

$$a_1 \times b_1$$

wherein $a_1$ is a regional cutoff value of remote Aβ influence metric at the ERC region calculated by iteratively removing outliers within the ERC region's data from the control population (e.g., Aβ-negative cognitively normal (CN) group) until no outlier arises and multiplies the maximum of remaining values by a small number as a buffer, values higher than about 1.5× the interquartile range over the third quartile are considered as outliers, and about the 95$^{th}$ percentile value of the remaining data after removing outliers being identified as the regional cutoff value of remote Aβ influence metric at the ERC region, and wherein $b_1$ is a tau W-score threshold of about 2.5.

In some embodiments, the second threshold used in any of the disclosed methods is from about 1 to about 10 in each cerebral hemisphere. In some embodiments, the second threshold is determined by the following formula:

$$a_2 \times b_2$$

wherein $a_2$ is a regional cutoff value of local Aβ deposition value at the ITG region calculated by iteratively removing outliers within the ITG region's data from the control population (e.g., Aβ-negative cognitively normal (CN) group) until no outlier arises and multiplies the maximum of remaining values by a small number as a buffer, values higher than about 1.5× the interquartile range over the third quartile are considered as outliers, and about 95$^{th}$ percentile value of the remaining data after removing outliers being identified as the regional cutoff value of local Aβ deposition value at the ITG region, and wherein $b_2$ is a tau W-score threshold of about 2.5.

In some embodiments, the one or plurality of regions of the brain of the subject to be analyzed in any of the disclosed methods are determined by calculating a goodness of fit (GOF) between a map of structural and/or functional connections of one or a plurality of regions of a brain of one or a plurality of subjects and a map of regions showing tau protein deposition in the brain of the one or plurality of subjects.

In some embodiments, comparing the Aβ protein deposition and/or the tau protein deposition in any of the disclosed method comprises quantifying a relative amount of Aβ protein deposition within left and/or right inferior temporal gyri (ITG) and quantifying a relative amount of tau protein deposition within left and/or right ITG. In some embodiments, calculating the first normalized score corresponding to interaction of Aβ protein deposition and tau protein deposition in any of the disclosed methods comprises calculating a likelihood of tau-positive neural tissue in one or a plurality of entorhinal cortex (ERC) regions of the brain of the subject interacting with Aβ-positive neural tissue in one or a plurality of non-ERC regions of the brain. In some embodiments, calculating the second normalized score in any of the disclosed methods comprises calculating a likelihood of tau-positive neural tissue interacting with Aβ-positive neural tissue locally within left and/or right inferior temporal gyri (ITG) of the brain of the subject.

In some embodiments, a subject is identified as being likely to respond to the AD treatment if the normalized first and second scores of step (d) comprise a high degree of interactions between ERC neural tissue with tau protein deposition and non-ERC neural tissue with Aβ protein deposition and a low degree of local interactions between tau protein deposition and Aβ protein deposition within the ITG. In some embodiments, a subject is identified as being likely to respond to the AD treatment if the normalized first and second scores of step (d) comprise a low degree of interactions between ERC neural tissue with tau protein deposition and non-ERC neural tissue with Aβ protein deposition and a low degree of local interactions between tau protein deposition and Aβ protein deposition within the ITG. In some embodiments, a subject is identified as being likely to respond to the AD treatment if the normalized first and second scores of step (d) comprise a high degree of interactions between ERC neural tissue with tau protein deposition and non-ERC neural tissue with Aβ protein deposition and a high degree of local interactions between tau protein deposition and Aβ protein deposition within the ITG.

In some embodiments, a likelihood of a subject or population of subjects responding to an Aβ modulating agent is predicted if the normalized first and second scores of step (d) comprise a high degree of interactions between ERC neural tissue with tau protein deposition and non-ERC neural tissue with Aβ protein deposition and a low degree of local interactions between tau protein deposition and Aβ protein deposition within the ITG. In some embodiments, a likelihood of a subject or population of subjects responding to a combinational treatment comprising both Aβ modulating agent and tau modulating agent is predicted if the normalized first and second scores of step (d) comprise a high degree of interactions between ERC neural tissue with tau protein deposition and non-ERC neural tissue with Aβ protein deposition and a high degree of local interactions between tau protein deposition and Aβ protein deposition within the ITG. In some embodiments, a likelihood of a subject or population of subjects benefiting from an Aβ prevention regime, such as by administering an Aβ vaccine, is predicted if the normalized first and second scores of step (d) comprise a low degree of interactions between ERC neural tissue with tau protein deposition and non-ERC neural tissue with Aβ protein deposition and a low degree of local interactions between tau protein deposition and Aβ protein deposition within the ITG.

In some embodiments, a pathological prognosis and/or a clinical outcome of a healthy subject and/or subject diagnosed with a particular disorder (e.g. a neurodegenerative disorder) or population of healthy subjects or subjects suffering from or at risk of developing a neurodegenerative disorder (e.g., Alzheimer's Disease) is predicted if the normalized first and second scores of step (d) comprise a high degree of interactions between ERC neural tissue with tau protein deposition and non-ERC neural tissue with Aβ protein deposition and a low degree of local interactions between tau protein deposition and Aβ protein deposition within the ITG. In such embodiments, a clinical outcome that the subject or population of subjects are likely at an early stage of developing AD can be predicted. In some embodiments, a pathological prognosis and/or a clinical outcome of a healthy subject and/or subject diagnosed with a particular disorder (e.g. a neurodegenerative disorder) or population of healthy subjects or subjects suffering from or at risk of developing a neurodegenerative disorder (e.g., Alzheimer's Disease) is predicted if the normalized first and second scores of step (d) comprise a high degree of interactions between ERC neural tissue with tau protein deposition and non-ERC neural tissue with Aβ protein deposition and a high degree of local interactions between tau protein deposition and Aβ protein deposition within the ITG. In such embodiments, a clinical outcome that the subject or population of subjects are likely at a more severe stage of AD. In some embodiments, a pathological prognosis and/or a clinical outcome of a healthy subject and/or subject diagnosed with a particular disorder (e.g. a neurodegenerative disorder) or population of healthy subjects or subjects suffering from or at risk of developing a neurodegenerative disorder (e.g., Alzheimer's Disease) is predicted if the normalized first and second scores of step (d) comprise a low degree of interactions between ERC neural tissue with tau protein deposition and non-ERC neural tissue with Aβ protein deposition and a low degree of local interactions between tau protein deposition and Aβ protein deposition within the ITG. In such embodiments, a clinical outcome that the subject or population of subjects are likely at low risk of developing AD.

In some embodiments, an AD therapy comprising administering an Aβ modulating agent in a subject or population of subjects is selected or optimized if the normalized first and second scores of step (d) comprise a high degree of interactions between ERC neural tissue with tau protein deposition and non-ERC neural tissue with Aβ protein deposition and a low degree of local interactions between tau protein deposition and Aβ protein deposition within the ITG. In some embodiments, an AD therapy is free of a step of administering a tau modulating agent in a subject or population of subjects is selected or optimized if the normalized first and second scores of step (d) comprise a high degree of interactions between ERC neural tissue with tau protein deposition and non-ERC neural tissue with Aβ protein deposition and a low degree of local interactions between tau protein deposition and Aβ protein deposition within the ITG. In some embodiments, an AD therapy comprising administering an Aβ modulating agent and a tau modulating agent in a subject or population of subjects is selected or optimized if the normalized first and second scores of step (d) comprise a high degree of interactions between ERC neural tissue with tau protein deposition and non-ERC neural tissue with Aβ protein deposition and a high degree of local interactions between tau protein deposition and Aβ protein deposition within the ITG. In some embodiments, an AD prevention therapy comprising, for example, administering an Aβ vaccine and/or tau vaccine in a subject or population of subjects is selected or optimized if the normalized first and second scores of step (d) comprise a low degree of interactions between ERC neural tissue with tau protein deposition and non-ERC neural tissue with Aβ protein deposition and a low degree of local interactions between tau protein deposition and Aβ protein deposition within the ITG.

The disclosure also relates to a computer program product encoded on a computer-readable storage medium comprising instructions for: (a) imaging a brain of the subject; (b) analyzing amyloid-beta (Aβ) protein deposition in at least one region within the brain of the subject; (c) analyzing tau protein deposition in at least one region within the brain of the subject; and (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject.

In some embodiments, the first normalized and second normalized scores calculated by the computer program product of the disclosure correspond to a plurality of regions of the brain of the subject. In some embodiments, the computer program product of the disclosure further comprises a step of calculating a first threshold relative to a first control dataset and calculating a second threshold relative to a second control dataset. In some embodiments, the computer program product of the disclosure further comprises (e) comparing the first normalized score to a first threshold and comparing a second normalized score to a second threshold; and (f) classifying the subject as being likely to respond to an AD treatment based upon results of comparing of step (e) relative to the first and/or second threshold, wherein each of steps (e) and (f) are performed after step (d), and wherein the first threshold is calculated relative to a first control dataset and the second threshold is calculated relative to a second control.

In some embodiments, the analyzing step (b) of the computer program product of the disclosure comprises: (i) determining an absence, presence or quantity of Aβ protein deposition within one or a plurality of regions of the brain of the subject, wherein step (i) is performed prior to step (e), and wherein the normalized score of step (d) is based upon step (i). In some embodiments, the analyzing step (c) of the computer program product of the disclosure comprises: (ii) determining an absence, presence or quantity of tau protein deposition within one or a plurality of regions of the brain of a subject, wherein step (ii) is performed prior to step (e), and wherein the normalized score of step (d) is based upon steps (ii).

The disclosure further relates to a system comprising: (i) any of the disclosed computer program product; and (ii) a processor operable to execute programs; and/or a memory associated with the processor.

The disclosure additionally relates to a system for identifying a protein interaction network in a subject or population of subjects comprising: a processor operable to execute programs; a memory associated with the processor; a database associated with said processor and said memory; a program stored in the memory and executable by the processor, the program being operable for: (a) imaging a brain of the subject; (b) analyzing Aβ protein deposition in at least one region within the brain of the subject; (c) analyzing tau protein deposition in at least one region within the brain of the subject; and (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject.

In some embodiments, the methods disclosed in the application comprise a step of calculating a first and second normalized score based upon Aβ deposition in a first and second region of the brain, respectively. In some embodiments, a first normalized score can be calculated by calculation of remote Aβ-tau interactions in three successive steps involving the disclosed algorithm. In some embodiments, the calculation of remote Aβ-tau interaction by calculating each region-of-interest's weighted connectivity strength, which is derived from a connectome selected from: the healthy structural connectome, a healthy functional connectome, an AD patient functional connectome, or an AD patient functional connectome, in each case, as compared to all other regions of the brain. In some embodiments, the region-of-interest is the region of interest in the brain where beta-amyloid and/or tau are being measured in the patient or patients. In some embodiments, the region of interest is chosen from any of the disclosed regions in Table 9 or the Figures. In some embodiments, the calculation of the remote Aβ-tau interaction comprises calculating connectivity strength followed by multiplying the connectivity strength of one or a plurality of regions of interest by the magnitude of Aβ-deposition within the one or plurality of regions, and subsequently adding any of those one or a plurality of products. In such embodiments, the sum of the aforementioned products is the Aβ influence metric. In some embodiments, the remote Aβ influence metric was multiplied by the magnitude of tau deposition within the region-of-interest. In some embodiments, the calculation of remote Aβ-tau interaction comprises calculating the connectivity strength, the Aβ influence metric and then multiplying the Aβ influence metric by tau-deposition in a localized region of the brain to arrive at the final interaction level. In some embodiments, the variation of interaction if measured by W and calculated as described in the specification and can be a range of from about 0.1 to 10.1.

The disclosure relates to a system for identifying a protein interaction network in a subject or population of subjects comprising:
- a processor operable to execute programs;
- a memory associated with the processor;
- a database associated with said processor and said memory;
- a program stored in the memory and executable by the processor, the program being operable for:
  - (a) analyzing amyloid-beta (Aβ) protein deposition in at least one region within the brain of the subject;
  - (b) analyzing tau protein deposition in at least one region within the brain of the subject; and
  - (c) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject.

In some embodiments, the system for identifying a protein interaction network of a subject comprises a program stored in the memory and executable by the processor, the program being further operable for: imaging the brain of the subject for beta-amyloid and/or tau deposition in regions of the brain. In some embodiments, the system for identifying a protein interaction network of a subject comprises a program stored in the memory and executable by the processor, the program being further operable for:

(e) comparing the first normalized score to a first threshold and comparing a second normalized score to a second threshold; and (f) classifying the subject as being likely to respond to an AD treatment based upon results of comparing of step (e) relative to the first and/or second threshold, wherein each of steps (e) and (f) are performed after step (d), and wherein the first threshold is calculated relative to a first control dataset and the second threshold is calculated relative to a second control.

In some embodiments the step of classifying comprise calculating the scores in respect to the subject and comparing that to the first and second thresholds, such that if the subject's score exceed or fall below a W value, the subject is classified as being responsive or nonresponsive to a therapy. In some embodiments, the W value is calculated according to the description of FIG. 5.

In some embodiments, the disclosure relates to methods disclosed in the application comprising a step of calculating a first and second normalized score based upon Aβ deposition in a first and second region of the brain, respectively. In some embodiments, a first normalized score can be calculated by calculation of remote Aβ-tau interactions in three successive steps involving the disclosed algorithm. In some embodiments, the calculation of remote Aβ-tau interaction by calculating each region-of-interest's weighted connectivity strength, which is derived from a connectome selected from: the healthy structural connectome, a healthy functional connectome, an AD patient functional connectome, or an AD patient functional connectome, in each case, as compared to all other regions of the brain. In some embodiments, the region-of-interest is the region of interest in the brain where beta-amyloid and/or tau are being measured in the patient or patients. In some embodiments, the region of interest is chosen from any of the disclosed regions in Table 9 or the Figures. In some embodiments, the calculation of the remote Aβ-tau interaction comprises calculating connectivity strength followed by multiplying the connectivity strength of one or a plurality of regions of interest by the magnitude of Aβ-deposition within the one or plurality of regions, and subsequently adding any of those one or a plurality of products. In such embodiments, the sum of the aforementioned products is the Aβ influence metric. In some embodiments, the remote Aβ influence metric was multiplied by the magnitude of tau deposition within the region-of-interest. In some embodiments, the calculation of remote Aβ-tau interaction comprises calculating the connectivity strength, the Aβ influence metric and then multiplying the Aβ influence metric by tau-deposition in a localized region of the brain to arrive at the final interaction level. In some embodiments, the thresholds are measured by W and calculated as described in the specification according to the descriptions of FIGS. 5 and 6.

In some embodiments, the program stored in the memory and executable by the processor of the system of the disclosure is further operable for: (e) comparing the first normalized score to a first threshold and comparing a second normalized score to a second threshold; and (f) classifying the subject as being likely to respond to an AD treatment based upon results of comparing of step (e) relative to the first and/or second threshold, wherein each of steps (e) and (f) are performed after step (d), and wherein the first threshold is calculated relative to a first control dataset and the second threshold is calculated relative to a second control. In some embodiments, the analyzing step (b) operated by the program of the disclosed system comprises: (i) determining an absence, presence or quantity of Aβ protein deposition within one or a plurality of regions of the brain of the subject, wherein step (i) is performed prior to step (e), and wherein the normalized score of step (d) is based upon step (i).

The disclosure further relates to a method of treating a subject diagnosed with or suspected or having AD comprising: (a) imaging a brain of the subject; (b) analyzing Aβ protein deposition in at least one region within the brain of the subject; (c) analyzing tau protein deposition in at least one region within the brain of the subject; (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject; (e) comparing the first normalized score to a first threshold and comparing a second normalized score to a second threshold; (f) classifying the subject as being likely to respond to an AD treatment based upon results of comparing of step (e) relative to the first and/or second threshold; wherein each of steps (e) and (f) are performed after step (d), and wherein the first threshold is calculated relative to a first control dataset and the second threshold is calculated relative to a second control; and (g) treating the subject with an AD treatment that comprises an Aβ modulating agent with or without a tau modulating agent.

BRIEF DESCRIPTION OF DRAWINGS

FIG. 1A. Dynamic biomarker models of AD[1,2] propose that tau aggregation undergoes non-linear acceleration in early MCI. FIG. 1B. Tau-PET data from the ADNI cohort (present study) support this concept by demonstrating a sharp increase in brain-wide tau deposition that begins in Aβ+ subjects with early MCI and accelerates in late MCI. Color bar in Aβ+ CN inset indicates tau-PET W-scores. FIG. 1C. Across the presymptomatic and prodromal AD cohorts, we estimated the sequence of regional tau-PET positivity in a data-driven, pseudo-longitudinal manner, using the group-level frequency distribution to infer the order. Subjects were sorted based on the number of tau-PET-positive ROIs, and tau-PET-positive regions in subjects representing the pre-acceleration, acceleration, and post-acceleration periods are shown. The acceleration period was defined as beginning where the slope in the frequency graph becomes greater than two and ending where that slope shows a second inflection, such that the second derivative becomes zero. Number labels on magnified insets (panels b and c) show ranks from the frequency distribution of tau-PET positivity. This approach identifies the entorhinal cortex (region labeled 1 in insets) as the most frequently tau-positive region, in keeping with cross-sectional neuropathological data[3]. CN, cognitively normal; MCI, mild cognitive impairment.

FIG. 2A-2C depict that network flow-based tau spreading model identifies tau propagation hubs in the inferior temporal gyri. FIG. 2A. A simplified network graph illustrates the network flow-based propagation model of tau spreading. Circles represent brain regions (nodes) and lines represent structural connections between node pairs (edges). The network flow-based model adopts a definition of maximum inter-nodal flow, which considers multiple distinct paths. Tau spreading from node i to node j is proportional to the total flow value, which is calculated as the sum of the maximum flow for each possible path. FIG. 2B. Searching across all brain regions (examples in yellow shading), propagation hubs were identified based on the goodness-of-fit (GOF) of their network flow-based connectivity maps, derived from healthy controls, to 7 pairs of binary inner/outer masks defined using the regions that represent the tau acceleration phase (see FIG. 1C and Example 6; GOF scores from example seed ROIs are shown). FIG. 2C. Two regions were identified as propagation hubs, having significant GOF scores across all inner/outer mask thresholds, and both were subregions of the inferior temporal gyrus (ITG). FA, fractional anisotropy; ROI, region-of-interest.

FIG. 3A. Using the network flow-based model of tau spreading, we examined the connectivity patterns of the two inferior temporal gyrus regions identified as propagation hubs. The connectivity maps of these hubs (Right ITG4 is highlighted in yellow) show high spatial correlation with the group-averaged tau W-score maps representing early and late MCI (scatter plots). FIG. 3B. Null hypothesis distributions of spatial correlations between the total network flow-based maps and tau W-score maps. The correlation coefficients were converted to z-scores, and the corresponding one-tailed p values were obtained for the two ITG propagation hubs. The red areas show correlation coefficients more than 2 s.d. greater than the mean. ITG, inferior temporal gyrus.

FIG. 4A. Aβ-tau interactions were modeled using two interaction types: remote and local. Remote interaction measures the effect of Aβ deposition within regions to which a given region is connected, weighted by the strength of those connections, whereas local interaction requires the presence of Aβ and tau deposition within the same region. For remote Aβ-tau interactions, the lateral entorhinal cortex (EC) regions ranked first within the frequency distribution for each hemisphere. In contrast, the identified left and right ITG propagation hubs ranked first and second for local Aβ-tau interaction frequency within left and right hemisphere, respectively. T-statistic distributions of continuous remote Aβ-tau and local Aβ-tau interaction values also show greater interactions in the lateral EC and ITG, respectively, compared to other brain regions. FIG. 4B. PrPc has been proposed to act as a receptor for oligomeric Aβ and to promote tau misfolding by stimulating Fyn kinase activity. PRNP and FYN RNA expression levels were mapped on the cortical surface based on microarray data from the Allen Human Brain Atlas. T-statistic distributions of remote Aβ-PRNP→tau-FYN and local Aβ-tau-PRNP-FYN show greater interactions in the lateral EC and ITG, respectively, compared to other brain regions.

FIG. 5A-5B depict a network-based molecular therapeutic window for Aβ-lowering therapy. FIG. 5A. Schematic representation of the AD progression model and a proposed therapeutic window for Aβ-lowering therapy based on the risk conferred by sufficient EC remote Aβ-tau interaction (Threshold 1, x-axis in top panel) and the probable Aβ-independence of tau spreading once tau interacts with Aβ within the ITG propagation hubs (Threshold 2, y-axis in top panel). FIG. 5B. Each subject's data are plotted for each hemisphere, with a line connecting left and right. The nonlinear relationship between metrics representing EC remote Aβ-tau interaction and ITG local Aβ-tau interaction support the notion that these phenomena represent a temporal progression. The discovery and validation datasets include similar proportions of subjects falling within the therapeutic window at each clinical stage. According to this model, suitability for Aβ-lowering therapy is most prevalent though still modest, in presymptomatic AD (Aβ+ CN) and prodromal AD (Aβ+ MCI), falling to only a small minority of subjects with dementia due to AD (Aβ+ AD). Group color-coding in (b) was chosen to reflect the predominant color in the model schematic (a).

FIG. 6A. Schematic representation of the AD progression model. FIG. 6B. Each subject's data are plotted, with an arrow connecting the baseline and follow-up scans (arrowhead points to later timepoint) where available. The nonlinear relationship between metrics representing EC remote Aβ-tau interaction and ITG local Aβ-tau interaction are supported by the overall trend in the data and support the notion that these phenomena represent a temporal progression. FIG. 6C. Subjects were stratified into four groups and overlaid on the pseudo-longitudinal subject order derived from the tau frequency distribution approach. Group color-coding in FIG. 6B and FIG. 6C indicates four tau group assignments at baseline. FIG. 6D. Annualized longitudinal tau W-score change maps, stratified by baseline tau group assignment, demonstrate the dramatic increase in tau spreading in the propagating tau group.

FIG. 10A. In the left hemisphere, the ITG propagation hub showed a network flow-based connectivity pattern that correlates strongly with the left hemisphere tau-PET W-score maps in early and late MCI, mirroring the findings for the right hemisphere (FIG. 3A).
FIG. 10B. A simplified network graph illustrates two other distinct potential contributors to tau propagation. Circles represent nodes (brain regions) and lines represent edges (structural connections between node pairs). Propagation based on physical proximity (Euclidean distance) and shortest network path length consider only one path each, with spreading predicted by the reciprocals of intermodal Euclidean distance and shortest path length. The total network flow-based connectivity map of the ITG propagation hubs shows higher spatial correlation with the patient-derived tau W-score maps vs. the other propagation models.
FIG. 10C. Key findings from the tau propagation model were reproduced with the Korean validation dataset. Null hypothesis distribution of spatial corre-
lations between the total network flow-based maps and tau
W-score maps mirror the format of FIG. 3B.

FIG. 12A. Assess-
ment of the network-based Aβ-tau interaction model in the
right hemisphere with the ADNI discovery dataset.
FIG.
12B. PRNP and FYN expression maps from the right
hemisphere from the 2 cases available through the Allen
Human Brain Atlas.
FIG. 12C. The network-based Aβ-tau
interaction model was broadly reproduced with Korean
validation dataset. Panels a-c mirror the format of FIG. 4.

FIG. 15A. In Aβ+ MCI subjects, tau-PET showed longitudinal tau
accumulation in a regional pattern that strongly correlated
with the network flow-based connectivity maps of the ITG
propagation hubs. Correlation coefficients describing the
relationship between each brain region's connectivity map
and the Aβ+ MCI tau accumulation map were converted to
z-scores and used to form a null hypothesis distribution;
one-tailed p values were computed for the two ITG hubs.
The red bars in the histogram show correlation coefficients
more than 2 s.d. greater than the mean.
FIG. 15B. The
Aβ-tau interaction model was assessed longitudinally with
the EC using the entire longitudinal dataset. For the EC, the
subjects were classified into 4 subgroups according to the
status of each region with respect to local Aβ and tau at
baseline. In subjects with tau in the EC at baseline, local EC
Aβ showed no effect on tau spreading. In subjects who
lacked EC Aβ, however, those with remote, connectivity-
based Aβ-tau interaction showed dramatically higher tau
spreading than those without (FIG. 15B inset).
FIG. 15C.
The Aβ-tau interaction model was assessed longitudinally
with the ITG using the entire longitudinal dataset. In contrast
to the EC, for the ITG regions, a transition to local Aβ-tau interaction was associated with significantly greater longi-
tudinal tau accumulation in downstream regions (FIG. 15C
inset).

DETAILED DESCRIPTION OF EMBODIMENTS

Figures 1A, 1B, 1C:
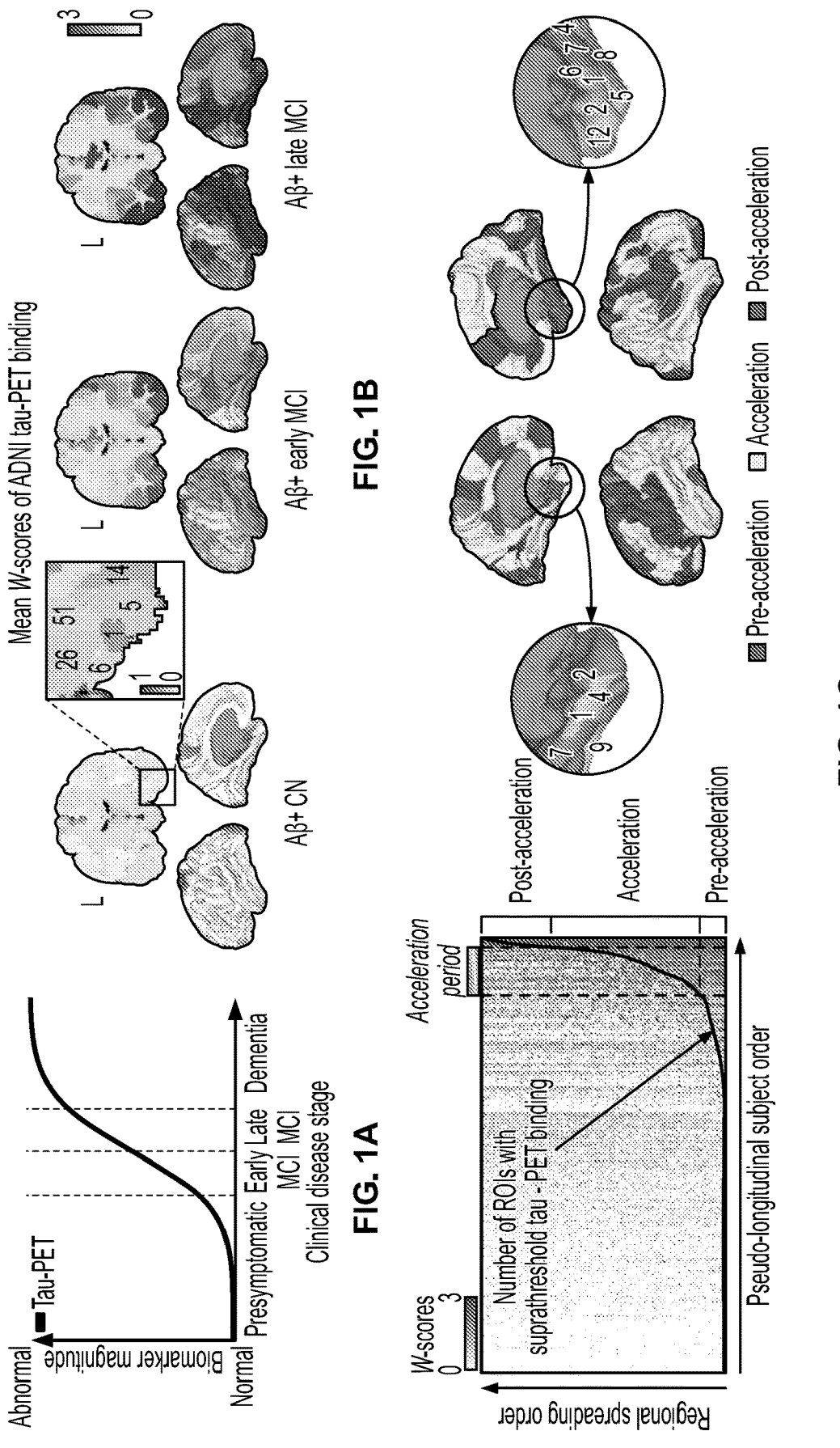
FIG. 1A-1C depict pseudo-longitudinal tau regional spreading order.

Before the present systems and methods are described, it
is to be understood that the present disclosure is not limited
to the particular processes, compositions, or methodologies
described, as these may vary. It is also to be understood that
the terminology used in the description is for the purposes of
describing the particular versions or embodiments only, and
is not intended to limit the scope of the present disclosure.
Unless defined otherwise, all technical and scientific terms
used herein have the same meanings as commonly under-
stood by one of ordinary skill in the art. Although any
methods and materials similar or equivalent to those
described herein can be used in the practice or testing of
embodiments of the present disclosure, the methods,
devices, and materials in some embodiments are now
described. All publications listed or disclosed herein are
incorporated by reference in their entirety. Nothing herein is
to be construed as an admission that the present disclosure
is not entitled to antedate such disclosure by virtue of prior
invention.

Definitions

Unless otherwise defined herein, scientific and technical
terms used in connection with the present disclosure shall
have the meanings that are commonly understood by those
of ordinary skill in the art. The meaning and scope of the
terms should be clear, however, in the event of any latent
ambiguity, definitions provided herein take precedent over
any dictionary or extrinsic definition. Further, unless other-
wise required by context, singular terms shall include plu-
ralities and plural terms shall include the singular.

The indefinite articles "a" and "an," as used herein in the
specification and in the claims, unless clearly indicated to
the contrary, should be understood to mean "at least one."
The phrase "and/or," as used herein in the specification and
in the claims, should be understood to mean "either or both"
of the elements so conjoined, i.e., elements that are con-
junctively present in some cases and disjunctively present in
other cases. Other elements may optionally be present other
than the elements specifically identified by the "and/or"
clause, whether related or unrelated to those elements spe-
cifically identified unless clearly indicated to the contrary.
Thus, as a non-limiting example, a reference to "A and/or
B," when used in conjunction with open-ended language
such as "comprising" can refer, in one embodiment, to A
without B (optionally including elements other than B); in
another embodiment, to B without A (optionally including
elements other than A); in yet another embodiment, to both
A and B (optionally including other elements); etc.

As used herein in the specification and in the claims, "or"
should be understood to have the same meaning as "and/or"
as defined above. For example, when separating items in a
list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of" "Consisting essentially of," when used in the claims, shall have its ordinary meaning as used in the field of patent law.

The term "about" is used herein to mean within the typical ranges of tolerances in the art. For example, "about" can be understood as about 2 standard deviations from the mean. According to certain embodiments, when referring to a measurable value such as an amount and the like, "about" is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value as such variations are appropriate to perform the disclosed methods. When "about" is present before a series of numbers or a range, it is understood that "about" can modify each of the numbers in the series or range.

The term "at least" prior to a number or series of numbers (e.g. "at least two") is understood to include the number adjacent to the term "at least," and all subsequent numbers or integers that could logically be included, as clear from context. When "at least" is present before a series of numbers or a range, it is understood that "at least" can modify each of the numbers in the series or range.

Ranges provided herein are understood to include all individual integer values and all subranges within the ranges.

As used herein, the terms "Alzheimer's patient," "AD patient," "individual diagnosed with AD" and "individual suspected of having AD" all refer to an individual who has been diagnosed with AD, has been given a probable diagnosis of AD, or an individual who has positive PET scans but otherwise lack major symptoms of AD and is without a clinical diagnosis of AD.

As used herein, the terms "amyloid-beta," "β-amyloid," "amyloid-β," "Aβ" and the like refer to β-amyloid proteins or peptides, proteins or peptides of a β-amyloid precursor, intermediates and their modifications and fragments, unless otherwise specified. In particular, "Aβ" refers to any peptide obtained by proteolytic treatment of a gene product, especially peptides that are associated with amyloid pathologies, including Aβ1-39, Aβ1-40, Aβ1-41, Aβ1-42 and Aβ1-43. As used herein, the terms "amyloid-beta," "β-amyloid," "amyloid-β," "Aβ" are synonymous. Unless otherwise indicated, the term "amyloid" refers to amyloidogenic proteins, peptides, fragments thereof, which may be soluble (e.g., monomeric or oligomeric) or insoluble (e.g., having a fibrillary structure or in an amyloid plaque). The full-length β-amyloid precursor protein A4 has the following amino acid sequence (UniProt Database accession No. P05067):

(SEQ ID NO: 1)
```
MLPGLALLLLAAWTARALEVPTDGNAGLLAEPQIAMFCGRLNMHM

NVQNGKWDSDPSGTKTCIDTKEGILQYCQEVYPELQITNVVEANQ

PVTIQNWCKRGRKQCKTHPHFVIPYRCLVGEFVSDALLVPDKCKF

LHQERMDVCETHLHWHTVAKETCSEKSTNLHDYGMLLPCGIDKFR
```

-continued
```
GVEFVCCPLAEESDNVDSADAEEDDSDVWWGGADTDYADGSEDKV

VEVAEEEEVAEVEEEEADDDEDDEDGDEVEEEAEEPYEEATERTT

SIATTTTTTTESVEEVVREVCSEQAETGPCRAMISRWYFDVTEGK

CAPFFYGGCGGNRNNFDTEEYCMAVCGSAMSQSLLKTTQEPLARD

PVKLPTTAASTPDAVDKYLETPGDENEHAHFQKAKERLEAKHRER

MSQVMREWEEAERQAKNLPKADKKAVIQHFQEKVESLEQEAANER

QQL VETHMARVEAMLNDRRRLALENYITALQAVPPRPRHVFNML

KKYVRAEQKDRQHTLKHFEHVRMVDPKKAAQIRSQVMTHLR VIY

ERMNQSLSLLYNVPAVAEEIQDEVDELLQKEQNYSDDVLANMISE

PRISYGNDALMPSLTETKTTVELLPVNGEFSLDDLQPWHSFGADS

VPANTENEVEPVDARPAADRGLTTRPGSGLTNIKTEEISEVKMDA

EFRHDSGYEVHHQKLVFFAEDVGSNKGAIIGLMVGGVVIATVIVI

TLVMLKKKQYTSIHHGVVEVDAAVTPEERHLSKMQQNGYENPTYK

FFEQMQN.
```

The term "Aβ modulating agent," as used herein, refers to any compound or agent that can modulate the amount of or prevent Aβ secretion, aggregation or deposition. In some embodiments, the Aβ modulating agent reduces Aβ secretion, deposition or production. In some embodiments, an Aβ modulating agent will reduce Aβ secretion, deposition or production by more than 10%. In some embodiments, an Aβ modulating agent will reduce Aβ secretion, deposition or production by more than 30%. In some embodiments, an Aβ modulating agent will reduce Aβ secretion, deposition or production by more than 50%. In some embodiments, an Aβ modulating agent will reduce Aβ secretion, deposition or production by more than 70%. In some embodiments, an Aβ modulating agent will reduce Aβ secretion, deposition or production by more than 90%. Examples of Aβ modulating agents include, but not limited to, aducanumab, AL-002, AL-003, amilomotide, umibecestat, bromocriptine mesylate, candesartan cilexetil, crenezumab, donanemab, elenbecestat, elenbecestat, lecanemab, gantenerumab, lanabecestat, lecanemab, levetiracetam ER, LDDN-9918, NPT-088, PU-AD, semorinemab, solanezumab, tarenflurbil, tilavonemab, trappsol cyclo, valacyclovir hydrochloride, zagotenemab, verubecestat and semagacestat.

The term "Aβ vaccine" used herein refers to a biological preparation that provides active, acquired anti-Aβ immunity for AD prevention and/or treatment. An Aβ vaccine may contain one or a plurality of peptides or fragments of an Aβ protein, such as the Aβ precursor protein provided elsewhere herein, in any length, or one or a plurality of nucleic acids (DNA and/or RNA) encoding such peptides or fragments of an Aβ protein.

As used herein, the term "tau" or "tau protein" refers to a group of highly soluble protein isoforms produced by alternative splicing from the gene MAPT (microtubule-associated protein tau). Tau can exist in phosphorylated forms (see, e.g., Goedert, Proc. Natl. Acad. Sci. U.S.A. 85:4051-4055(1988); Goedert, EMBO J. 8:393-399(1989); Lee, Neuron 2:1615-1624(1989); Goedert, Neuron 3:519-526(1989); Andreadis, Biochemistry 31:10626-10633 (1992) and has been reported to have a role in stabilizing microtubules, particularly in the central nervous system. Unless otherwise apparent from the context, reference to tau means a natural human form of tau including all isoforms irrespective of whether posttranslational modification (e.g., phosphorylation, glycation, or acetylation) is present. The full-length tau protein has the following amino acid sequence (UniProt Database accession No. P10636):

```
                                         (SEQ ID NO: 2)
MAEPRQEFEVMEDHAGTYGLGDRKDQGGYTMHQDQEGDTDAGLKE

SPLQTPTEDGSEEPGSETSDAKSTPTAEDVTAPLVDEGAPGKQAA

AQPHTEIPEGTTAEEAGIGDTPSLEDEAAGHVTQEPESGKVVQEG

FLREPGPPGLSHQLMSGMPGAPLLPEGPREATRQPSGTGPEDTEG

GRHAPELLKHQLLGDLHQEGPPLKGAGGKERPGSKEEVDEDRDVD

ESSPQDSPPSKASPAQDGRPPQTAAREATSIPGFPAEGAIPLPVD

FLSKVSTEIPASEPDGPSVGRAKGQDAPLEFTFHVEITPNVQKEQ

AHSEEHLGRAAFPGAPGEGPEARGPSLGEDTKEADLPEPSEKQPA

AAPRGKPVSRVPQLKARMVSKSKDGTGSDDKKAKTSTRSSAKTLK

NRPCLSPKHPTPGSSDPLIQPSSPAVCPEPPSSPKYVSSVTSRTG

SSGAKEMKLKGADGKTKIATPRGAAPPGQKGQANATRIPAKTPPA

PKTPPSSGEPPKSGDRSGYSSPGSPGTPGSRSRTPSLPTPPTREP

KKVAVVRTPPKSPSSAKSRLQTAPVPMPDLKNVKSKIGSTENLKH

QPGGGKVQIINKKLDLSNVQSKCGSKDNIKHVPGGGSVQIVYKPV

DLSKVTSKCGSLGNIHHKPGGGQVEVKSEKLDFKDRVQSKIGSLD

NITHVPGGGNKKIETHKLTFRENAKAKTDHGAEIVYKSPVVSGDT

SPRHLSNVSSTGSIDMVDSPQLATLADEVSASLAKQGL.
```

The term "tau modulating agent," as used herein, refers to any compound or agent that can modulate the amount of or prevent tau secretion, aggregation or deposition. In some embodiments, the tau modulating agent reduces tau secretion, deposition or production. In some embodiments, a tau modulating agent will reduce tau secretion, deposition or production by more than 10%. In some embodiments, a tau modulating agent will reduce tau secretion, deposition or production by more than 30%. In some embodiments, a tau modulating agent will reduce tau secretion, deposition or production by more than 50%. In some embodiments, a tau modulating agent will reduce tau secretion, deposition or production by more than 70%. In some embodiments, a tau modulating agent will reduce tau secretion, deposition or production by more than 90%. Examples of tau modulating agents include, but not limited to PP2A activators such as memantine and sodium selenite, GSK3β inhibitors such as tideglusib and lithium chloride, acetylation inhibitors such as salsalate, OGA inhibitors such as MK-8719, aggregation inhibitors such as LMTX and curcumin, microtubule stabilizers such as epithilone D, NAP and TPI 287, PDE4 inhibitors such as BPN14770, and anti-tau antibodies, such as ABBV-8E12.

The term "tau vaccine" used herein refers to a biological preparation that provides active, acquired anti-tau immunity for AD prevention and/or treatment. A tau vaccine may contain one or a plurality of peptides or fragments of a tau protein, such as the tau protein provided elsewhere herein, in any length, or one or a plurality of nucleic acids (DNA and/or RNA) encoding such peptides or fragments of an tau protein.

As used herein, the term "animal" includes, but is not limited to, humans and non-human vertebrates such as wild animals, rodents, such as rats, ferrets, and domesticated animals, and farm animals, such as dogs, cats, horses, pigs, cows, sheep, and goats. In some embodiments, the animal is a mammal. In some embodiments, the animal is a human. In some embodiments, the animal is a non-human mammal.

As used herein, the terms "comprising" (and any form of comprising, such as "comprise," "comprises," and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

The term "diagnosis" or "prognosis" as used herein refers to the use of information (e.g., genetic information or data from other molecular tests on biological samples, signs and symptoms, physical exam findings, cognitive performance results, etc.) to anticipate the most likely outcomes, timeframes, and/or response to a particular treatment for a given disease, disorder, or condition, based on comparisons with a plurality of individuals sharing common nucleotide sequences, symptoms, signs, family histories, or other data relevant to consideration of a patient's health status.

As used herein, the term "goodness of fit" or "GOF" refers to a test that is used to test if sample data fits a distribution from a certain population (i.e. a population with a normal distribution or one with a Weibull distribution). In some embodiments, the GOF score of the disclosure can be calculated as described in Example 6.

As used herein, the phrase "in need thereof" means that the animal or mammal has been identified or suspected as having a need for the particular method or treatment. In some embodiments, the identification can be by any means of diagnosis or observation. In any of the methods and treatments described herein, the animal or mammal can be in need thereof. In some embodiments, the subject in need thereof is a human seeking prevention of AD. In some embodiments, the subject in need thereof is a human diagnosed with AD. In some embodiments, the subject in need thereof is a human seeking treatment for AD. In some embodiments, the subject in need thereof is a human undergoing treatment for AD.

The term "interaction" as used herein refers to a reciprocal action between Aβ protein deposition and tau protein deposition. In some embodiments, an interaction between Aβ protein deposition and tau protein deposition is their relative amount within one or a plurality of regions within the brain. In some embodiments, an interaction between Aβ protein deposition and tau protein deposition is their relative amount within the same region(s) of the brain. In some embodiments, an interaction between Aβ protein deposition and tau protein deposition is their relative amount within different region(s) of the brain.

The "remote Aβ influence metric" as used herein is a value used to quantify the value assigned to the influence of beta-amyloid expression or deposition within regions of the brain of a patient, and, in some embodiments, a human patient, on another region or regions within a brain of the same patient. The remote Aβ influence metric involves weighting the influence of amyloid deposition in one set of regions on other brain regions based on the estimated neural connectivity between the involved brain regions. In some embodiments, the methods of selecting an AD therapy of a patient or prognosing the clinical outcome of a patient comprise the step of multiplying the remote Aβ influence metric by the magnitude of tau deposition in certain localized portions of the brain to arrive at a value that correlates to, among other things, prognosis of the patient and potential responsiveness to treatments/therapies of AD. In some embodiments, the neural connectivity variables used to calculate the remote Aβ influence metric comprises reviewing datasets from a structural connectome of healthy subject populations. In some embodiments, the neural connectivity variables used to calculate the remote Aβ influence metric comprises reviewing datasets from a functional connectome of healthy subject populations. In some embodiments, the neural connectivity variables used to calculate the remote Aβ influence metric comprises reviewing datasets from a structural connectome of subject populations with Alzheimer's disease. In some embodiments, the neural connectivity variables used to calculate the remote Aβ influence metric comprises reviewing datasets from a functional connectome of healthy subject populations. In some embodiments, the neural connectivity variables used to calculate the remote Aβ influence metric comprises reviewing datasets from a structural connectome of the individual subject in question. In some embodiments, the neural connectivity variables used to calculate the remote Aβ influence metric comprises reviewing datasets from a functional connectome of the individual subject in question. The value can be multiplied by the magnitude of tau deposition in a certain localized portion or portions of the brain to arrive at a value that correlates to, among other things, prognosis of the patient and potential responsiveness to treatments/therapies of AD.

The term "structural connectome" as used herein is a set of estimated neural connections between brain regions, with or without the estimated strengths of those connections, derived from a brain imaging method, such as diffusion tensor magnetic resonance imaging, designed to determine a physical (i.e., axonal) connection between brain regions. A non-limiting example of how to calculate the structural connectome appears on page 85 of the specification.

The term "functional connectome" as used herein is a set of estimated neural connections between brain regions, with or without the estimated strengths of those connections, derived from a brain imaging method, such as "resting-state" or "task-free" functional magnetic resonance imaging, designed to determine a functional connection (based on correlated activity signals) between brain regions. A non-limiting example of how to calculate the functional connectome can be found in citation number 29, which is incorporated by reference in its entirety.

As used herein, the term "mammal" means any animal in the class Mammalia such as rodent (i.e., mouse, rat, or guinea pig), monkey, cat, dog, cow, horse, pig, or human. In some embodiments, the mammal is a human. In some embodiments, the mammal refers to any non-human mammal. The present disclosure relates to any of the methods or compositions of matter wherein the sample is taken from a mammal or non-human mammal. The present disclosure relates to any of the methods or compositions of matter wherein the sample is taken from a human or non-human primate.

As used herein, the term "predicting" refers to making a finding that an individual has a significantly enhanced probability or likelihood of benefiting from and/or responding to an AD treatment. In some embodiments, the AD treatment is administration of an Aβ modulating agent. In some embodiments, the AD treatment is administration of an Aβ vaccine. In some embodiments, the AD treatment is administration of a tau modulating agent. In some embodiments, the AD treatment is administration of a tau vaccine.

In some embodiments, the AD treatment is a combinational treatment by administering an Aβ modulating agent together with a tau modulating agent. In some embodiments, the AD treatment is a therapy capable of modifying the effects of Aβ and/or tau depositions.

A "score" is a numerical value that may be assigned or generated after normalization of the value based upon the presence, absence, or quantity of deposition of amyloid-beta (Aβ) protein and tau protein in the brain of a subject. In some embodiments, the score is normalized in respect to a control data value.

As used herein, the term "stratifying" refers to sorting individuals into different classes or strata based on the features of a neurological disease. For example, stratifying a population of individuals with Alzheimer's disease involves assigning the individuals on the basis of the severity of the disease (e.g., mild, moderate, advanced, etc.).

As used herein, the term "subject," "individual" or "patient," used interchangeably, means any animal, including mammals, such as mice, rats, other rodents, rabbits, dogs, cats, swine, cattle, sheep, horses, or primates, such as humans. In some embodiments, the subject is a human seeking treatment for Alzheimer's disease. In some embodiments, the subject is a human diagnosed with Alzheimer's disease. In some embodiments, the subject is a human suspected of having Alzheimer's disease. In some embodiments, the subject is a healthy human being.

As used herein, the term "threshold" refers to a defined value by which a normalized score can be categorized. By comparing to a preset threshold, a subject, with corresponding qualitative and/or quantitative data corresponding to a normalized score, can be classified based upon whether it is above or below the preset threshold.

As used herein, the terms "treat," "treated," or "treating" can refer to therapeutic treatment and/or prophylactic or preventative measures wherein the object is to prevent or slow down (lessen) an undesired physiological condition, disorder or disease, or obtain beneficial or desired clinical results. For purposes of the embodiments described herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment can also include eliciting a clinically significant response without excessive levels of side effects. Treatment also includes prolonging survival as compared to expected survival if not receiving treatment.

As used herein, the term "therapeutic" means an agent utilized to treat, combat, ameliorate, prevent or improve an unwanted condition or disease of a patient.

A "therapeutically effective amount" or "effective amount" of a composition is a predetermined amount calculated to achieve the desired effect, i.e., to treat, combat, ameliorate, prevent or improve one or more symptoms of a viral infection. The activity contemplated by the present methods includes both medical therapeutic and/or prophylactic treatment, as appropriate. The specific dose of a compound administered according to the present disclosure to obtain therapeutic and/or prophylactic effects will, of course, be determined by the particular circumstances surrounding the case, including, for example, the compound administered, the route of administration, and the condition being treated. It will be understood that the effective amount administered will be determined by the physician in the light of the relevant circumstances including the condition to be treated, the choice of compound to be administered, and the chosen route of administration, and therefore the above dosage ranges are not intended to limit the scope of the present disclosure in any way. A therapeutically effective amount of compounds of embodiments of the present disclosure is typically an amount such that when it is administered in a physiologically tolerable excipient composition, it is sufficient to achieve an effective systemic concentration or local concentration in the tissue.

Methods

The disclosure relates to methods of predicting efficacy of Alzheimer's disease treatments. In some embodiments, the disclosure provides a method of identifying a subject likely to respond to an Alzheimer's disease (AD) treatment. In some embodiments, the disclosure provides a method of identifying a subject's responsiveness to an AD treatment. In some embodiments, the disclosure provides a method of predicting a likelihood of a subject or population of subjects does or does not respond to an AD treatment. In some embodiments, the AD treatment is administration of an Aβ modulating agent. In some embodiments, the AD treatment is administration of an Aβ vaccine. In some embodiments, the AD treatment is administration of a tau modulating agent. In some embodiments, the AD treatment is administration of a tau vaccine. In some embodiments, the AD treatment is a combinational treatment by administering an Aβ modulating agent together with a tau modulating agent. In some embodiments, the AD treatment is a therapy capable of modifying the effects of Aβ and/or tau depositions. In some embodiments, the disclosure provides a method of predicting a pathological prognosis and/or a clinical outcome of a subject or population of healthy subjects or subjects at risk for or suffering from AD. In some embodiments, the disclosure provides a method of selecting or optimizing an AD therapy in a subject or population of subjects.

The disclosure also relates to a method of categorizing a subject as having a probability or likelihood of benefiting or not benefiting from one or a plurality of AD treatments. In some embodiments, the method comprises a step of analyzing protein deposition in the brain of the subject, such as by PET scan. In some embodiments, the method comprises analyzing the Aβ protein deposition and the tau protein deposition in the brain of the subject. In some embodiments, the method comprises comparing the Aβ protein deposition and the tau protein deposition in one or more regions of the brain. In some embodiments, the method comprises a step of classifying the subject as having a probability or likelihood of benefiting or not benefiting from an AD treatment based upon the severity or pervasiveness of Aβ and/or tau protein depositions in the brain.

The disclosure further relates to a method of modifying an AD treatment regimen of a subject in need thereof, the method comprising: (i) imaging the brain of the subject; (ii) performing algorithmic analysis on the images of the subject's brain; and (iii) altering an AD treatment regimen of the subject, wherein the altering is determined by classifying the probability or likelihood that the subject will benefit from or be responsive to one or more AD treatments. In some embodiments, the probability or likelihood of the subject to benefit from or be responsive to one or more AD treatments is based upon the severity or pervasiveness of Aβ and/or tau protein depositions in the brain.

The disclosure also relates to a method of treating and/or preventing AD in a subject in need thereof, the method comprising: (i) imaging the brain of the subject; (ii) performing algorithmic analysis on the images of the subject's brain; and (iii) administering to the subject one or a plurality of AD treatments. In some embodiments, the one or plurality of AD treatments administered to the subject are determined based upon the severity or pervasiveness of Aβ and/or tau protein depositions in the brain.

The disclosed methods comprise: (a) imaging a brain of the subject; (b) analyzing amyloid-beta (Aβ) protein deposition in at least one region within the brain of the subject; (c) analyzing tau protein deposition in at least one region within the brain of the subject; and (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject. In some embodiments, the method further comprises (e) comparing the first normalized score to a first threshold and comparing a second normalized score to a second threshold; and (f) c classifying the subject as being likely to respond to an AD treatment based upon results of comparing of step (e) relative to the first and/or second threshold; wherein each of steps (e) and (f) are performed after step (d), and wherein the first threshold is calculated relative to a first control dataset and the second threshold is calculated relative to a second control.

Any method suitable for imaging a brain of the subject may be used. Examples include, but are not limited to, brain scanning technologies such as magnetic resonance imaging (MRI), single-photon emission-computed tomography (SPECT) and positron emission tomography (PET) scanning, and other available methods of measuring and recording brain structure or activity. In some embodiments, the disclosed methods involve collection of structural MRI scans of a subject. In some embodiments, the disclosed methods involve collection of PET scans of a subject. In some embodiments, the disclosed methods involve collection of structural MRI and PET scans of a subject. In some embodiments, the disclosed methods involve collection of structural MRI or PET scans of one or a plurality of subjects from two groups of subjects (e.g., a group comprising individuals diagnosed with or suspected of having AD and a reference group comprising individuals not having AD). In some embodiments, the disclosed methods involve collection of structural MRI and PET scans of one or a plurality of subjects from two groups of subjects (e.g., a group comprising individuals diagnosed with or suspected of having AD and a reference group comprising individuals not having AD).

Structural MRIs may be obtained using, for instance, 3T MRI scanners with 3D magnetization-prepared rapid gradient echo (MP-RAGE) or inversion recovery-fast spoiled gradient recalled (IR-SPGR) sequences. Depending on MRI scanner vendors, the scanning protocols may differ.

PET scans can be performed using, for example, a conventional PET imager and auxiliary equipment. The scan typically includes one or more regions of the brain known in general to be associated with Aβ and/or tau protein deposits and one or more regions in which few if any deposits are generally present to serve as controls. In some embodiments, the PET scan can be performed using a radiotracer. In other embodiments, the PET signal can be from a specific radiotracer such as one that binds to molecules found in altered amounts in AD. Suitable PET ligands include radiolabeled compounds or antibodies. The radioisotope used can be, for example, $C^{11}$, $N^{13}$, $O^{15}$, $F^{18}$, or $I^{123}$. The interval between administering the PET ligand and performing the scan can depend on the PET ligand and particularly its rate of uptake and clearing into the brain, and the half-life of its radiolabel.

In some embodiments, the PET signal is from a specific radiotracer useful for measuring Aβ protein deposition in the brain of the subject. Any suitable radiotracer for detecting Aβ protein deposition in the brain may be used, which includes but not limited to, Pittsburgh compound B ($^{11}$C-PiB), $^{18}$F-FDG (fluorodeoxyglucose), $^{18}$F-florbetapir (AV45 or $^{18}$F-FBP), $^{18}$F-florbetaben ($^{18}$F-FBB) and $^{18}$F-Flutemetamol ($^{18}$F-FMT).

In some embodiments, the PET signal is from a specific radiotracer useful for measuring tau protein deposition in the brain of the subject. Any suitable radiotracer for detecting tau protein deposition in the brain may be used, which includes but not limited to, $^{18}$F-flortaucipir (AV1451), THK5317, $^{18}$F-MK6240 and PBB3.

The signal detected in a PET scan can be represented as a multidimensional image. The multidimensional image can be in two dimensions representing a cross-section through the brain, in three dimensions, representing the three dimensional brain, or in four dimensions representing changes in the three dimensional brain over time. In some embodiments, a color scale can be used with different colors indicating different amounts of label and, inferentially, Aβ and tau protein deposits detected. In some embodiments, the results of the scan can be presented numerically, with numbers relating to the amount of label detected and consequently amounts of Aβ and tau protein deposits. The label present in a region of the brain known to be associated with deposits for Aβ and tau can be compared with the label present in a region known not to be associated with deposits to provide a ratio indicative of the extent of deposits within the former region. For the same radiolabeled ligand, such ratios provide a comparable measure of Aβ and tau protein deposits and changes thereof between different patients. In some embodiments, the disclosed methods use a PET scan to image the brain of a subject. In some embodiments, the disclosed methods use a MRI scan to image the brain of a subject. In some embodiments, the disclosed methods analyze one or a plurality of PET scan images to determine the Aβ protein deposition in the brain. In some embodiments, the disclosed methods analyze one or a plurality of PET scan images to determine the tau protein deposition in the brain.

In some embodiments, normal levels of Aβ deposits can be determined by the amount of Aβ deposits detected in the brains of a representative sample of individuals in the general population who have not been diagnosed with AD and are not considered at elevated risk of developing such disease (e.g., a representative sample of disease-free individuals under 50 years of age). Alternatively, a normal level can be recognized in an individual patient if the PET signal in a region of the brain in which Aβ deposits are known to develop is not different (within the accuracy of measurement) from the signal from a region of the brain in which it is known that such deposits do not normally develop. An elevated level in an individual can be recognized by comparison to the normal levels (e.g., outside mean and variance of a standard deviation) or simply from an elevated signal beyond experimental error in a region of the brain associated with Aβ deposits compared with a region not known to be associated with Aβ deposits. For purposes of comparing the levels of Aβ deposits in an individual and population, the Aβ deposits should preferably be determined in the same region(s) of the brain, these regions including at least one region in which Aβ deposits associated with AD are known to form. In some embodiments, the disclosed methods analyze Aβ protein deposition in the brain of a subject by determining an absence, presence or quantity of Aβ protein deposition within one region of the brain. In some embodiments, the disclosed methods analyze Aβ protein deposition in the brain of a subject by determining an absence, presence or quantity of Aβ protein deposition within a plurality of regions of the brain.

In some embodiments, normal levels of tau deposits can be determined by the amount of tau deposits detected in the brains of a representative sample of individuals in the general population who have not been diagnosed with tau and are not considered at elevated risk of developing such disease (e.g., a representative sample of disease-free individuals under 50 years of age). Alternatively, a normal level can be recognized in an individual patient if the PET signal in a region of the brain in which tau deposits are known to develop is not different (within the accuracy of measurement) from the signal from a region of the brain in which it is known that such deposits do not normally develop. An elevated level in an individual can be recognized by comparison to the normal levels (e.g., outside mean and variance of a standard deviation) or simply from an elevated signal beyond experimental error in a region of the brain associated with tau deposits compared with a region not known to be associated with tau deposits. For purposes of comparing the levels of tau deposits in an individual and population, the tau deposits should preferably be determined in the same region(s) of the brain, these regions including at least one region in which tau deposits associated with AD are known to form. In some embodiments, the disclosed methods analyze tau protein deposition in the brain of a subject by determining an absence, presence or quantity of tau protein deposition within one region of the brain. In some embodiments, the disclosed methods analyze tau protein deposition in the brain of a subject by determining an absence, presence or quantity of tau protein deposition within a plurality of regions of the brain.

Based on the levels of Aβ deposits and the levels of tau deposits determined in various regions within the brain of an individual, a normalized score corresponding to the interaction, or relative level, of Aβ protein deposition and tau protein deposition in one or a plurality of regions of the brain can be calculated. In some embodiments, the normalized score corresponds to the interaction of Aβ protein deposition and tau protein deposition in one single region of the brain. In some embodiments, the normalized score corresponds to the interaction of Aβ protein deposition and tau protein deposition in two regions of the brain. In some embodiments, the normalized score corresponds to the interaction of Aβ protein deposition and tau protein deposition in three regions of the brain. In some embodiments, the normalized score corresponds to the interaction of Aβ protein deposition and tau protein deposition in four regions of the brain. In some embodiments, the normalized score corresponds to the interaction of Aβ protein deposition and tau protein deposition in five regions of the brain. In some embodiments, the normalized score corresponds to the interaction of Aβ protein deposition and tau protein deposition in more than five regions of the brain. In some embodiments, the normalized score corresponds to the interaction of Aβ protein deposition and tau protein deposition in less than 10 regions of the brain. In some embodiments, the normalized score corresponds to the interaction of Aβ protein deposition and tau protein deposition in more than 10 regions of the brain.

In some embodiments, the disclosed methods calculate a normalized score by comparing tau protein deposition in at least one region of interest within the brain to Aβ protein deposition in one or a plurality of regions of the brain outside of the at least one region of interest. In some embodiments, the disclosed methods calculate a normalized score by comparing Aβ protein deposition and tau protein deposition in the same at least one region of interest of the brain. In some embodiments, the disclosed methods calculate a first normalized score by comparing tau protein deposition in at least one first region of interest within the brain to Aβ protein deposition in one or a plurality of regions of the brain outside of the at least one first region of interest, and calculate a second normalized score by comparing Aβ protein deposition and tau protein deposition in at least one second region of interest of the brain. In some embodiments, the disclosed methods calculate the first normalized score by the following formula:

$$\left(\sum_j \delta_{ij} \cdot A\beta\,SUVR_j\right) \times \left(Tau\ W\text{--score}_i\right)$$

wherein $\Sigma_j\ \delta_{ij}$ is the structural or functional connectivity between the first region of interest, region i, and the one or plurality of regions, denoted here as region(s) j, of the brain outside of the first region of interest; wherein $SUVR_j$ is a first standardized uptake value ratio (SUVR) corresponding to the Aβ protein deposition in the one or plurality of regions, denoted here as region(s) j, of the brain outside of the first region of interest, wherein Tau W-score, is a first standardized value corresponding to the tau protein deposition in the first region of interest of the brain, the first standardized value being calculated based on a control population of subjects, wherein the second normalized score is calculated by the following formula: $(A\beta\ SUVR_k) \times (Tau\ W\text{-score}_k)$ wherein $SUVR_k$ is a second SUVR corresponding to the Aβ protein deposition in the second region of interest of the brain, denoted here as region k, and wherein Tau W-score$_k$ is a second standardized value corresponding to the tau protein deposition in the second region of interest of the brain, denoted here as k, the second standardized value being calculated based on the control population of subjects.

In some embodiments, the disclosed methods further comprise a step of calculating a first threshold relative to a first control dataset. Threshold calculation is an influence metric derived from the control dataset. In some embodiments, the first threshold calculated by any of the disclosed methods is determined by the following formula:

$$a_1 \times b_1$$

wherein $a_1$ is a regional cutoff value of remote Aβ influence metric at the ERC region calculated by iteratively removing outliers within the ERC region's data from the control population (e.g., Aβ-negative cognitively normal (CN) group) until no outlier arises and multiplies the maximum of remaining values by a small number as a buffer, values higher than about 1.5× the interquartile range over the third quartile are considered as outliers, and about the 95$^{th}$ percentile value of the remaining data after removing outliers being identified as the regional cutoff value of remote Aβ influence metric at the ERC region, and wherein $b_1$ is a tau W-score threshold of about 2.5.

In some embodiments, the first threshold is from about 1 to about 10 in each cerebral hemisphere. In some embodiments, the first threshold is from about 2 to about 9 in each cerebral hemisphere. In some embodiments, the first threshold is from about 3 to about 8 in each cerebral hemisphere. In some embodiments, the first threshold is from about 4 to about 7 in each cerebral hemisphere. In some embodiments, the first threshold is from about 5 to about 6 in each cerebral hemisphere. In some embodiments, the first threshold is about 1 in each cerebral hemisphere. In some embodiments, the first threshold is about 2 in each cerebral hemisphere. In some embodiments, the first threshold is about 3 in each cerebral hemisphere. In some embodiments, the first threshold is about 4 in each cerebral hemisphere. In some embodiments, the first threshold is about 5 in each cerebral hemisphere. In some embodiments, the first threshold is about 6 in each cerebral hemisphere. In some embodiments, the first threshold is about 7 in each cerebral hemisphere. In some embodiments, the first threshold is about 8 in each cerebral hemisphere. In some embodiments, the first threshold is about 9 in each cerebral hemisphere. In some embodiments, the first threshold is about 10 in each cerebral hemisphere.

In some embodiments, the disclosed methods further comprise a step of calculating a second threshold relative to a second control dataset. In some embodiments, the second threshold is determined by the following formula:

$$a_2 \times b_2$$

wherein $a_2$ is a regional cutoff value of local Aβ deposition value at the ITG region calculated by iteratively removing outliers within the ITG region's data from the control population (e.g., Aβ-negative cognitively normal (CN) group) until no outlier arises and multiplies the maximum of remaining values by a small number as a buffer, values higher than about 1.5× the interquartile range over the third quartile are considered as outliers, and about the 95$^{th}$ percentile value of the remaining data after removing outliers being identified as the regional cutoff value of local Aβ deposition value at the ITG region, and wherein $b_2$ is a tau W-score threshold of about 2.5.

In some embodiments, the second threshold is from about 1 to about 10 in each cerebral hemisphere. In some embodiments, the second threshold is from about 2 to about 9 in each cerebral hemisphere. In some embodiments, the second threshold is from about 3 to about 8 in each cerebral hemisphere. In some embodiments, the second threshold is from about 4 to about 7 in each cerebral hemisphere. In some embodiments, the second threshold is from about 5 to about 6 in each cerebral hemisphere. In some embodiments, the second threshold is about 1 in each cerebral hemisphere. In some embodiments, the second threshold is about 2 in each cerebral hemisphere. In some embodiments, the second threshold is about 3 in each cerebral hemisphere. In some embodiments, the second threshold is about 4 in each cerebral hemisphere. In some embodiments, the second threshold is about 5 in each cerebral hemisphere. In some embodiments, the second threshold is about 6 in each cerebral hemisphere. In some embodiments, the second threshold is about 7 in each cerebral hemisphere. In some embodiments, the second threshold is about 8 in each cerebral hemisphere. In some embodiments, the second threshold is about 9 in each cerebral hemisphere. In some embodiments, the second threshold is about 10 in each cerebral hemisphere.

The first dataset and the second dataset used in the disclosed methods for calculating the first threshold and the second threshold may be the same dataset or different datasets. In some embodiments, the first dataset used for calculating the first threshold is the same as the second dataset used for calculating the second threshold. In some embodiments, the first dataset used for calculating the first threshold is a different dataset from the second dataset used for calculating the second threshold.

In some embodiments, the one or plurality of regions of the brain of a subject to be analyzed are determined by calculating a goodness of fit (GOF) between a map of structural and/or functional connections of one or a plurality of regions of a brain of one or a plurality of subjects and a map of regions showing tau protein deposition in the brain of the one or plurality of subjects. In some embodiments, the region of the brain to be analyzed is the left inferior temporal gyri (ITG). In some embodiments, the region of the brain to be analyzed is the right ITG. In some embodiments, the regions of the brain to be analyzed are the left and right ITG. In some embodiments, the regions of the brain to be analyzed are entorhinal cortex (ERC) regions of the brain. In some embodiments, the regions of the brain to be analyzed are non-ERC regions of the brain. In some embodiments, the regions of the brain to be analyzed include ERC regions and non-ERC regions.

In some embodiments, the disclosed methods analyze the Aβ protein deposition by quantifying a relative amount of Aβ protein deposition within left ITG. In some embodiments, the disclosed methods analyze the Aβ protein deposition by quantifying a relative amount of Aβ protein deposition within right ITG. In some embodiments, the disclosed methods analyze the Aβ protein deposition by quantifying a relative amount of Aβ protein deposition within left and right ITG.

In some embodiments, the disclosed methods analyze the tau protein deposition by quantifying a relative amount of tau protein deposition within left ITG. In some embodiments, the disclosed methods analyze the tau protein deposition by quantifying a relative amount of tau protein deposition within right ITG. In some embodiments, the disclosed methods analyze the tau protein deposition by quantifying a relative amount of tau protein deposition within left and right ITG.

In some embodiments, the disclosed methods compare the Aβ protein deposition and the tau protein deposition by comparing their relative amounts within left ITG. In some embodiments, the disclosed methods compare the Aβ protein deposition and the tau protein deposition by comparing their relative amounts within right ITG. In some embodiments, the disclosed methods compare the Aβ protein deposition and the tau protein deposition by comparing their relative amounts within left and right ITG.

In some embodiments, the disclosed methods comprise calculating the first normalized score corresponding to the interaction of Aβ protein deposition and tau protein deposition in a first region of the brain by calculating a likelihood of tau-positive neural tissue in one or a plurality of ERC regions of the brain interacting with Aβ-positive neural tissue in one or a plurality of non-ERC regions of the brain. In some embodiments, the disclosed methods calculate the first normalized score by calculating a likelihood of tau-positive neural tissue in one or a plurality of non-ERC regions of the brain interacting with Aβ-positive neural tissue in one or a plurality of ERC regions of the brain.

In some embodiments, the disclosed methods calculate the second normalized score corresponding to the interaction of Aβ protein deposition and tau protein deposition in a second region of the brain by calculating a likelihood of tau-positive neural tissue interacting with Aβ-positive neural tissue locally within left ITG of the brain. In some embodiments, the disclosed methods calculate the second normalized score by calculating a likelihood of tau-positive neural tissue interacting with Aβ-positive neural tissue locally within right ITG of the brain. In some embodiments, the disclosed methods calculate the second normalized score by calculating a likelihood of tau-positive neural tissue interacting with Aβ-positive neural tissue locally within left and right ITG of the brain.

Based on the calculated first and second normalized scores, the methods of the disclosure make it possible to assess the suitability of a given AD therapy for the subject. Referring to FIG. 5, for example, when the calculated first normalized score is below the first threshold and the calculated second normalized score is also below the second threshold, the subject is likely to be at low risk of imminently developing AD and thus can benefit from an AD preventive therapy, such as by administration of an Aβ vaccine and/or tau vaccine. When the calculated first normalized score exceeds the first threshold but the calculated second normalized score remains below the second threshold, the subject is likely at an early stage of AD and thus can benefit from an AD therapy that comprises an Aβ modulating agent, such as anti-Aβ antibodies. When the calculated first normalized score exceeds the first threshold and the calculated second normalized score also exceeds the second threshold, the subject is likely at a later stage of AD and can benefit from a more aggressive AD treatment that comprises both an Aβ modulating agent and a tau modulating agent. In some embodiments therefore, the calculated first normalized score must exceed the first threshold before the calculated second normalized score exceeds the second threshold. Throughout the entire disclosure, when the calculated first normalized score is below the first threshold, it is described as the normalized first score comprising a low degree of interactions between ERC neural tissue with tau protein deposition and non-ERC neural tissue with Aβ protein deposition. When the calculated first normalized score exceeds the first threshold, on the other hand, it is described as the normalized first score comprising a high degree of interactions between ERC neural tissue with tau protein deposition and non-ERC neural tissue with Aβ protein deposition. When the calculated second normalized score is below the second threshold, it is described as the normalized second score comprising a low degree of local interactions between tau protein deposition and Aβ protein deposition within the ITG. When the calculated second normalized score exceeds the second threshold, on the other hand, it is described as the normalized second score comprising a high degree of local interactions between tau protein deposition and Aβ protein deposition within the ITG.

In some embodiments, a subject is identified by any of the disclosed methods as being likely to respond to an AD treatment, such as an Aβ-modulating agent, if the normalized first and second scores comprise a high degree of interactions between ERC neural tissue with tau protein deposition and non-ERC neural tissue with Aβ protein deposition. In some embodiments, a subject is identified by any of the disclosed methods as being likely to respond to an AD treatment, such as an Aβ-modulating agent, if the normalized first and second scores comprise a low degree of local interactions between tau protein deposition and Aβ protein deposition within the ITG. In some embodiments, a subject is identified by any of the disclosed methods as being likely to respond to an AD treatment, such as an Aβ-modulating agent, if the normalized first and second scores comprise a high degree of interactions between ERC neural tissue with tau protein deposition and non-ERC neural tissue with Aβ protein deposition and a low degree of local interactions between tau protein deposition and Aβ protein deposition within the ITG.

In some embodiments, a subject is identified by any of the disclosed methods as being likely to respond to an AD treatment, such as a combinational treatment with an Aβ-modulating agent and a tau modulating agent, if the normalized first and second scores comprise a high degree of interactions between ERC neural tissue with tau protein deposition and non-ERC neural tissue with Aβ protein deposition. In some embodiments, a subject is identified by any of the disclosed methods as being likely to respond to an AD treatment, such as a combinational treatment with an Aβ-modulating agent and a tau modulating agent, if the normalized first and second scores comprise a high degree of local interactions between tau protein deposition and Aβ protein deposition within the ITG. In some embodiments, a subject is identified by any of the disclosed methods as being likely to respond to an AD treatment, such as a combinational treatment with an Aβ-modulating agent and a tau modulating agent, if the normalized first and second scores comprise a high degree of interactions between ERC neural tissue with tau protein deposition and non-ERC neural tissue with Aβ protein deposition and a high degree of local interactions between tau protein deposition and Aβ protein deposition within the ITG.

In some embodiments, a subject is identified by any of the disclosed methods as being likely to benefit from an AD preventive treatment, such as an Aβ vaccine or tau vaccine, if the normalized first and second scores comprise a low degree of interactions between ERC neural tissue with tau protein deposition and non-ERC neural tissue with Aβ protein deposition. In some embodiments, a subject is identified by any of the disclosed methods as being likely to benefit from an AD preventive treatment, such as an Aβ vaccine or tau vaccine, if the normalized first and second scores comprise a low degree of local interactions between tau protein deposition and Aβ protein deposition within the ITG. In some embodiments, a subject is identified by any of the disclosed methods as being likely to benefit from an AD preventive treatment, such as an Aβ vaccine or tau vaccine, if the normalized first and second scores comprise a low degree of interactions between ERC neural tissue with tau protein deposition and non-ERC neural tissue with Aβ protein deposition and a low degree of local interactions between tau protein deposition and Aβ protein deposition within the ITG.

In some embodiments, a pathological prognosis and/or a clinical outcome of a healthy subject and/or subject diagnosed with a particular disorder (e.g. a neurodegenerative disorder) or population of healthy subjects or subjects suffering from or at risk of developing a neurodegenerative disorder (e.g., AD) is predicted if the normalized first and second scores of step (d) comprise a high degree of interactions between ERC neural tissue with tau protein deposition and non-ERC neural tissue with Aβ protein deposition and a low degree of local interactions between tau protein deposition and Aβ protein deposition within the ITG. In such embodiments, a clinical outcome that the subject or population of subjects are likely at an early stage of developing AD can be predicted and thus an AD treatment comprising an Aβ modulating agent such as an anti-Aβ antibody can be a more beneficial treatment choice. In some embodiments, a pathological prognosis and/or a clinical outcome of a healthy subject and/or subject diagnosed with a particular disorder (e.g. a neurodegenerative disorder) or population of healthy subjects or subjects suffering from or at risk of developing a neurodegenerative disorder (e.g., AD) is predicted if the normalized first and second scores of step (d) comprise a low degree of interactions between ERC neural tissue with tau protein deposition and non-ERC neural tissue with Aβ protein deposition and a low degree of local interactions between tau protein deposition and Aβ protein deposition within the ITG. In such embodiments, a clinical outcome that the subject or population of subjects are likely at low risk of developing AD can be predicted and thus an AD preventive regime such as Aβ vaccine can be more beneficial. In some embodiments, a pathological prognosis and/or a clinical outcome of a healthy subject and/or subject diagnosed with a particular disorder (e.g. a neurodegenerative disorder) or population of healthy subjects or subjects suffering from or at risk of developing a neurodegenerative disorder (e.g., AD) is predicted if the normalized first and second scores of step (d) comprise a high degree of interactions between ERC neural tissue with tau protein deposition and non-ERC neural tissue with Aβ protein deposition and a high degree of local interactions between tau protein deposition and Aβ protein deposition within the ITG. In such embodiments, a clinical outcome that the subject or population of subjects are likely at a more severe stage of AD and thus a combinational treatment targeting both Aβ and tau such as a joint Aβ modulating agent and tau modulating agent can be a better treatment choice.

In some embodiments, an AD therapy, such as administering an Aβ modulating agent, in a subject or population of subjects is selected or optimized if the normalized first and second scores of step (d) comprise a high degree of interactions between ERC neural tissue with tau protein deposition and non-ERC neural tissue with Aβ protein deposition and a low degree of local interactions between tau protein deposition and Aβ protein deposition within the ITG. In some embodiments, an AD therapy, such as administering an Aβ vaccine and/or tau vaccine, in a subject or population of subjects is selected or optimized if the normalized first and second scores of step (d) comprise a low degree of interactions between ERC neural tissue with tau protein deposition and non-ERC neural tissue with Aβ protein deposition and a low degree of local interactions between tau protein deposition and Aβ protein deposition within the ITG. In some embodiments, an AD therapy, such as administering a tau modifying agent, in a subject or population of subjects is selected or optimized if the normalized first and second scores of step (d) comprise a high degree of interactions between ERC neural tissue with tau protein deposition and non-ERC neural tissue with Aβ protein deposition and a high degree of local interactions between tau protein deposition and Aβ protein deposition within the ITG.

In some embodiments, the disclosure relates to a method of treating a subject diagnosed with or suspected or having AD comprising: (a) imaging a brain of the subject as disclosed elsewhere herein; (b) analyzing Aβ protein deposition in at least one region within the brain of the subject as disclosed elsewhere herein; (c) analyzing tau protein deposition in at least one region within the brain of the subject as disclosed elsewhere herein; and (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject using the algorithms disclosed elsewhere herein; (e) comparing the first normalized score to a first threshold and comparing a second normalized score to a second threshold; (f) classifying the subject as being likely to respond to an AD treatment based upon results of comparing of step (e) relative to the first and/or second threshold; wherein each of steps (e) and (f) are performed after step (d), and wherein the first threshold is calculated relative to a first control dataset and the second threshold is calculated relative to a second control; and (g) treating the subject with an AD treatment or AD therapy. In some embodiments, the AD treatment is administration of an Aβ modulating agent. In some embodiments, the Aβ modulating agent used in the disclosed method is a compound or agent that reduces Aβ secretion. In some embodiments, the Aβ modulating agent is a compound or agent that reduces Aβ deposition. In some embodiments, the Aβ modulating agent is a compound or agent that reduces Aβ production. In some embodiments, the Aβ modulating agent is a compound or agent that reduces Aβ secretion, deposition or production by more than 10%. In some embodiments, the Aβ modulating agent is a compound or agent that reduces Aβ secretion, deposition or production by more than 20%. In some embodiments, the Aβ modulating agent is a compound or agent that reduces Aβ secretion, deposition or production by more than 30%. In some embodiments, the Aβ modulating agent is a compound or agent that reduces Aβ secretion, deposition or production by more than 40%. In some embodiments, the Aβ modulating agent is a compound or agent that reduces Aβ secretion, deposition or production by more than 50%. In some embodiments, the Aβ modulating agent is a compound or agent that reduces Aβ secretion, deposition or production by more than 60%. In some embodiments, the Aβ modulating agent is a compound or agent that reduces Aβ secretion, deposition or production by more than 70%. In some embodiments, the Aβ modulating agent is a compound or agent that reduces Aβ secretion, deposition or production by more than 80%. In some embodiments, the Aβ modulating agent is a compound or agent that reduces Aβ secretion, deposition or production by more than 90%. In some embodiments, the Aβ modulating agent is a compound or agent chosen from aducanumab, AL-002, AL-003, amilomotide, umibecestat, bromocriptine mesylate, candesartan cilexetil, crenezumab, donanemab, elenbecestat, elenbecestat, lecanemab, gantenerumab, lanabecestat, lecanemab, levetiracetam ER, LDDN-9918, NPT-088, PU-AD, semorinemab, solanezumab, tarenflurbil, tilavonemab, trappsol cyclo, valacyclovir hydrochloride, zagotenemab, verubecestat and semagacestat. In some embodiments, the AD treatment is administration of an Aβ vaccine. A list of Aβ targeting therapy is provided in Table X below.

TABLE X

| List of Aβ targeting therapy. | | | | | | |
|---|---|---|---|---|---|---|
| Drug Name | Generic Name | Brand Name | Company Name | Route of Administration | Chemical Name | Chemical Formula |
| RV-01 | | | Intellect Neurosciences Inc | | | |
| RV-03 | | | Intellect Neurosciences Inc | | | |
| AD-01 | | | GlaxoSmithKline Plc | Subcutaneous | | |
| AD-02 | | | AFFiRiS AG | Subcutaneous | | |
| AD-03 | | | GlaxoSmithKline Plc | Subcutaneous | | |
| ANVS-401 | Posiphen | | Annovis Bio Inc | Oral | [(3aR,8bS)-3,4,8b-trimethyl-2,3a-dihydro-1H-pyrrolo[2,3-b]indol-7-yl] N-phenylcarbamate | C20H23N3O2 |
| XEL-001HG | | | Xel Pharmaceuticals Inc | Topical | 5,9-Methanocyclo-octa(b)pyridin-2(1H)-one, 5-amino-11-ethylidene-5,6,9,10-tetrahydro-7-methyl-, (5R,9R,11E)- | C15H18N2O |
| XEL-001HP | | | Xel Pharmaceuticals Inc | Transdermal | 5,9-Methanocyclo-octa(b)pyridin-2(1H)-one, 5-amino-11-ethylidene-5,6,9,10-tetrahydro-7-methyl-, (5R,9R,11E)- | C15H18N2O |

TABLE X-continued

| | | | | Route of | Chemical | Chemical |
|---|---|---|---|---|---|---|
| Drug Name | Generic Name | Brand Name | Company Name | Administration | Name | Formula |
| RG-6102 | gantenerumab | | F. Hoffmann-La Roche Ltd | Intravenous | Immunoglobulin G1, anti-(human 1-40-beta-amyloid/human 1-42-beta-amyloid) (human monoclonal gamma1-chain), disulfide with human monoclonal kappa-chain, dimer | C6496H10072N1740O2024S42 |
| gantenerumab | gantenerumab | | F. Hoffmann-La Roche Ltd Chugai Pharmaceutical Co Ltd | Subcutaneous | Immunoglobulin G1, anti-(human 1-40-beta-amyloid/human 1-42-beta-amyloid) (human monoclonal gamma1-chain), disulfide with human monoclonal kappa-chain, dimer | C6496H10072N1740O2024S42 |
| crenezumab | crenezumab | | Genentech USA Inc | Intravenous; Subcutaneous | Immunoglobulin G4, anti-(human 1-40-beta-amyloid/human 1-42-beta-amyloid) (human-mouse monoclonal MABT5102A heavy chain), disulfide with human-mouse monoclonal MABT5102A light chain, dimer | C6348H9796N1688O2010S44 |
| GAL-101 | | | Galimedix Therapeutics Ltd | Ophthalmic | N-(D-tryptophyl)-2-aminoisobutyric acid | C15H19N3O3 |
| ponezumab | ponezumab | | Pfizer Inc | Intravenous | Immunoglobulin G2, anti-(human beta-amyloid) (human-mouse monoclonalPF-04360365 clone 9TL heavy chain), disulfide with human-mouse monoclonal PF-04360365 clone 9TL light chain, dimer | C6552H10158N1730O2090S52 |
| amilomotide | amilomotide [INN] | | Novartis AG | Intramuscular; Subcutaneous | | |
| lecanemab | lecanemab | | Eisai Co Ltd | Intravenous | Immunoglobulin G1, anti-(human ß-amyloid protofibril) | C6544H10088N1744O2032S46 |

TABLE X-continued

| | | | | | | |
|---|---|---|---|---|---|---|
| | | | | List of Aβ targeting therapy. | | |
| Drug Name | Generic Name | Brand Name | Company Name | Route of Administration | Chemical Name | Chemical Formula |
| | | | | | (human-Mus musculus monoclonal BAN2401 heavy chain), disulfide with human-Mus musculus monoclonal BAN2401 light chain, dimer | |
| AAB-003 | | | Johnson & Johnson | Intravenous | Bapineuzumab (236-alanine,237-alanine,239-alanine) (humanized clone 3d6 gamma1-chain) | |
| aducanumab | aducanumab | | Biogen Inc | Intravenous | Immunoglobulin G1, anti-(human beta-amyloid) (human monoclonal BIIB037 heavy chain), disulfide with human monoclonal BIIB037 kappa-chain, dimer | C6472H10028N1740O2014S46 |
| UB-311 | | | United Neuroscience Ltd | Intramuscular | | |
| ARN-2966 | | | Aria Neurosciences Inc | | 2-(pyridin-2-ylmethylamino) phenol | C12H12N2O |
| cromolyn sodium | cromolyn sodium | | AZTherapies Inc | Inhalational; Oral | disodium;5-[3-(2-carboxylato-4-oxochromen-5-yl)oxy-2-hydroxypropoxy]-4-oxochromene-2-carboxylate | C23H14Na2O11 |
| donanemab | donanemab | | Eli Lilly and Co | Intravenous; Subcutaneous | Immunoglobulin G1, anti-(human pyroglutamyl Abeta (3-x) peptide) (human clone LY3002813 gamma1-chain), disulfide with human clone LY3002813 kappa-chain, dimer | C6452H10038N1708O2013S42 |
| Bisnorcymserine | | | Annovis Bio Inc | Oral | [(3aR,8bS)-8b-methyl-2,3,3a,4-tetrahydro-1H-pyrrolo[2,3-b]indol-7-yl] N-(4-propan-2-ylphenyl)carba-mate;(2R,3R)-2,3-dihydroxybutane-dioic acid | C25H31N3O8 |

TABLE X-continued

List of Aβ targeting therapy.

| Drug Name | Generic Name | Brand Name | Company Name | Route of Administration | Chemical Name | Chemical Formula |
|---|---|---|---|---|---|---|
| miridesap | miridesap | | GlaxoSmithKline Plc | Intravenous; Subcutaneous | (2R)-1-[6-[(2R)-2-carboxypyr-rolidin-1-yl]-6-oxohexanoyl]pyr-rolidine-2-carboxylic acid | C16—H24—N2—O6 |
| tramiprosate | tramiprosate | Cerebril Alzhemed c | BELLUS Health Inc | Oral | 3-aminopropane-1-sulfonic acid | C3H9NO3S |
| AN-1792 | | | Johnson & Johnson | Intramuscular | 3-[2-[2-[2-[2-(9H-fluoren-9-yloxycarbonyl-amino)ethoxy]eth-oxy]ethoxy]eth-oxy]propanoic acid | C25H31NO8 |
| SP-233 | | | Samaritan Pharmaceuticals, Inc. (Inactive) | | (20S,22R,25R)-Spirosta-5-ene-3beta-ol)hexanoate | C33—H52—O4 |
| T-817MA | | | FUJIFILM Toyama Chemical Co Ltd | Oral | 1-[3-[2-(1-benzothiophen-5-yl)ethoxy]pro-pyl]azetidin-3-ol; (Z)-but-2-enedioic acid | C20H25NO6S |
| BGC20-1178 | | | Senexis Limited (Inactive) | | 7,8-dihydro-5-methyl-8-(1-phenylethyl)-6H-pyrrolo [3,2-e] [1,2,4] triazolo [1,5-a] pyrimidine | C16H17N5 |
| bapineuzumab | bapineuzumab | | Johnson & Johnson | Intravenous | Immunoglobulin G1, anti-(human beta-amyloid) (human-mouse monoclonal heavy chain), disulfide with human-mouse monoclonal light chain, dimer | C6466H10018N1734O2026S44 |
| leuprolide acetate | leuprolide acetate | | Curaxis Pharmaceutical Corp (Inactive) | | acetic acid;(2S)-N-[(2S)-1-[[(2S)-1-[[(2S)-1-[[(2R)-1-[[(2S)-1-[[(2S)-5-(diaminomethyl ideneamino)-1-[(2S)-2-(ethylcarbam-oyl)pyrrolidin-1-yl]-1-oxopentan-2-yl]amino]-4-methyl-1-oxopentan-2-yl]amino]-4-methyl-1-oxopentan-2-yl]amino]-3-(4-hydroxyphenyl)-1-oxopropan-2-yl]amino]-3-hydroxy-1-oxopropan-2-yl]amino]-3-(1H-indol-3-yl)- | C61H88N16O14 |

TABLE X-continued

| | | | | | | |
|---|---|---|---|---|---|---|
| | | | | | List of Aβ targeting therapy. | |
| Drug Name | Generic Name | Brand Name | Company Name | Route of Administration | Chemical Name | Chemical Formula |
| | | | | | 1-oxopropan-2-yl]amino]-3-(1H-imidazol-5-yl)-1-oxopropan-2-yl]-5-oxopyrrolidine-2-carboxamide | |
| SHP-622 | | | Intellect Neurosciences Inc | Oral | 3-(1H-indol-3-yl)propanoic acid | C11H11NO2 |
| ELND-005 | | | OPKO Health Inc | Oral | Cyclohexane-1,2,3,4,5,6-hexol | C6H12O6 |
| solanezumab | solanezumab | | Eli Lilly and Co | Intravenous | Immunoglobulin G1, anti-(human beta-amyloid) (human-mouse monoclonal LY2062430 heavy chain), disulfide with human-mouse monoclonal LY2062430 light chain, dimer | C6408H9944N1716O1998S42 |
| latrepirdine dihydrochloride | latrepirdine dihydrochloride | Dimebon | Pfizer Inc | Oral | 2,8-dimethyl-5-[2-(6-methylpyridin-3-yl)ethyl]-3,4-dihydro-1H-pyrido[4,3-b]indole;dihydrochloride | C21H27Cl2N3 |
| cromolyn sodium + ibuprofen | cromolyn sodium + ibuprofen | | AZTherapies Inc | Inhalational; Oral | Cromolyn sodium: disodium;5-[3-(2-carboxylato-4-oxochromen-5-yl)oxy-2-hydroxypropoxy]-4-oxochromene-2-carboxylate Ibuprofen: 2-[4-(2-methylpropyl)phenyl]propanoic acid | Cromolyn sodium: C23H14Na2O11 Ibuprofen: C13H18O2 |
| (curcumin + paclitaxel) | paclitaxel | | Augustus BioTarget Inc | | curcumin:(1E,6E)-1,7-bis(4-hydroxy-3-methoxyphenyl)hepta-1,6-diene-3,5-dione; paclitaxel:(2a,5b,7b,10b,13a)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate | curcumin: C21H20O6; paclitaxel: C47H51NO14 |

TABLE X-continued

List of Aβ targeting therapy.

| Drug Name | Generic Name | Brand Name | Company Name | Route of Administration | Chemical Name | Chemical Formula |
|---|---|---|---|---|---|---|
| donanemab + LY-3202626 | donanemab + LY-3202626 | | Eli Lilly and Co | Intravenous; Oral | donanemab: Immunoglobulin G1, anti-(human pyroglutamyl Abeta (3-x) peptide) (human clone LY3002813 gamma1-chain), disulfide with human clone LY3002813 kappa-chain, dimer | donanemab: C6452H10038N1708O2013S42 |
| LY-2811376 + donanemab | LY-2811376 + donanemab | | Eli Lilly and Co | | LY-2811376: (4S)-4-(2,4-difluoro-5-pyrimidin-5-ylphenyl)-4-methyl-5,6-dihydro-1,3-thiazin-2-amine donanemab: Immunoglobulin G1, anti-(human pyroglutamyl Abeta (3-x) peptide) (human clone LY3002813 gamma1-chain), disulfide with human clone LY3002813 kappa-chain, dimer | LY-2811376: C15H14F2N4S donanemab: C6452H10038N1708O2013S42 |
| Vaccine to Target ADDL for Alzheimer's Disease | | | Acumen Pharmaceuticals Inc | | | |
| Vaccine to Target Amyloid Beta Peptide for Alzheimer's Disease | | | University of California San Diego | | | |
| 2AP-04 | | | 2A Pharma AB | | | |
| AV-1959D | | | Capo Therapeutics Inc | | | |
| AV-1959R | | | Capo Therapeutics Inc | | | |
| Vaccine to Target Amyloid Beta Peptide for Alzheimer's Disease | | | Ben-Gurion University of the Negev | | | |
| YM-3711 | | | Vitruvian Biomedical Inc | | | |
| ABvac-40 | | | Araclon Biotech SL | Subcutaneous | | |
| ABvac-42 | | | Araclon Biotech SL | | | |
| ACI-24 | | | AC Immune SA | Subcutaneous | | |
| AV-1960CP | | | Capo Therapeutics Inc | | | |
| Vaccine to Target Beta-Amyloid for Alzheimer's Disease | | | Tria Bioscience Corp | | | |

TABLE X-continued

List of Aβ targeting therapy.

| Drug Name | Generic Name | Brand Name | Company Name | Route of Administration | Chemical Name | Chemical Formula |
|---|---|---|---|---|---|---|
| YM-7555 | | | Vitruvian Biomedical Inc | | | |
| sodium oligomannate | | Oligomannate | Shanghai Green Valley Pharmaceutical Co Ltd | Oral | | |
| ALZ-801 | | | Alzheon Inc | Oral | | |
| AZP-2006 | | | AlzProtect SAS | Oral | N-(3-(4-(3-(diisobutyl-amino)propyl)pi-perazin-1-yl)propyl)-1H-benzo[d]imid-azol-2-amine disulphate salt | |
| Neurostem | | | MediPost Co Ltd | Intracerebral | | |
| KHK-6640 | | | Kyowa Kirin Co Ltd | Intravenous | | |
| LY-3372993 | | | Eli Lilly and Co | Intravenous | | |
| MEDI-1814 | | | AstraZeneca Plc | Intravenous; Subcutaneous | | |
| NPT-088 | | | Proclara Biosciences Inc | Intravenous | | |
| NPT-189 | | | Proclara Biosciences Inc | Intravenous | | |
| PRI-002 | | | Priavoid GmbH | Oral | | |
| RIV-1061 | | | Revivo Therapeutics Inc | | | |
| ANVS-405 | | | Annovis Bio Inc | Intravenous | | |
| DDNA-0101 | | | Dadang & BIO Co Ltd | | | |
| 15-M | | | Alzhyme Pty Ltd | | | |
| AA-7 | | | Cesa Alliance SA | | | |
| ACU-193 | | | Acumen Pharmaceuticals Inc | | | |
| AD-05 | | | AFFIRIS AG | Subcutaneous | | |
| AGT-160 | | | ArmaGen Inc | | | |
| ALZ-101 | | | Alzinova AB | | | |
| ALZ-1903 | | | Alzheon Inc | Oral | | |
| ALZ-201 | | | Alzinova AB | | | |
| Antibody to Inhibit Amyloid Beta for Alzheimer's Disease | | | ICB International Inc | | | |
| BAN-2502 | | | Eisai Co Ltd | | | |
| BEY-2153 | | | BeyondBio Inc | Oral | | |
| CB-401 | | | Cantabio Pharmaceuticals Inc | Oral | | |
| CBB-68 | | | Crossbeta Biosciences BV | Oral | | |
| Cell Therapy to Inhibit Amyloid beta for Alzheimer's Disease | | | Ben-Gurion University of the Negev | | | |
| Cellular Immunotherapy to Target Beta-Amyloid for Alzheimer's Disease | | | MegaNano BioTech Inc | | | |
| CLR-01 | | | University of California Los Angeles | | | |
| CP-2 | | | AfaSci Inc | | (1R,5aS,7S)-7-[(2R)-1-(6-aminopurin-3-yl)propan-2-yl]-3-methyl-1,5a,6,7,8,9-hexahydro-pyrano[4,3-b]chromen-1-ol | C21H25N5O3 |

TABLE X-continued

List of Aβ targeting therapy.

| Drug Name | Generic Name | Brand Name | Company Name | Route of Administration | Chemical Name | Chemical Formula |
|---|---|---|---|---|---|---|
| Drugs to Inhibit Amyloid Beta Protein and Tau for Alzheimer's Disease | | | Ovensa Inc | | | |
| EG-30 | | | Tel Aviv University | Ophthalmic | | |
| GAL-201 | | | Galimedix Therapeutics Ltd | Oral | | |
| Gene Therapy to Inhibit Amyloid Beta for Alzheimers's Disease | | | DegenRx BV | | | |
| Gene Therapy to Inhibit Amyloid Precursor Protein for Alzheimer's Disease | | | University of Nebraska Medical Center | | | |
| Gene Therapy to Inhibit Beta Amyloid for Alzheimer's Disease | | | Ewha Womans University | | | |
| KAL-ABP | | | Kalgene Pharmaceuticals Inc | | | |
| Monoclonal Antibodies to Inhibit APP and csgG for Alzheimer's Disease, Familial Danish Dementia and Bacterial Infections | | | Lankenau Institute for Medical Research | | | |
| Monoclonal Antibodies to Inhibit APP for Alzheimer's Disease | | | Prothena Corp Plc | | | |
| Monoclonal Antibodies to Inhibit Tau, Amyloid Beta and Alpha-Synuclein for Neurodegenerative Diseases | | | NYU Langone Health System | | | |
| Monoclonal Antibody to Inhibit Amyloid beta for Alzheimer's Disease | | | University of Gottingen | | | |
| Monoclonal Antibody to Inhibit Amyloid Beta for Alzheimer's Disease | | | LifeArc | | | |
| NAT | | | Tel Aviv University | | | |
| NovAD | | NovAD | NovMetaPharma Co Ltd | | | |
| NPT-4003 | | | Neuropore Therapies Inc | Oral | | |
| NPT-4401 | | | Neuropore Therapies Inc | Oral | | |
| OL-1 | | | Saint Louis University | | | |
| P-8 | | | Cenna Biosciences Inc | Nasal; Subcutaneous | | |
| PBDC-06 | | | Vivoryon Therapeutics AG | | | |
| Peptide to Inhibit Amyloid Beta | | | University of California San | | | |

TABLE X-continued

List of Aβ targeting therapy.

| Drug Name | Generic Name | Brand Name | Company Name | Route of Administration | Chemical Name | Chemical Formula |
|---|---|---|---|---|---|---|
| Peptide for Alzheimer's Disease | | | Diego | | | |
| Peptides to Inhibit Beta Amyloid for Alzheimer's Disease | | | Stony Brook University | | | |
| PMN-310 | | | ProMIS Neurosciences Inc | | | |
| RIOR-2TAT | | | Lancaster University | | | |
| RU-505 | | | Rockefeller University | | N-benzyl-2-tert-butyl-N-[2-(dimethyl-amino)ethyl]-7-(4-fluorophenyl)pyr-azolo[1,5-alpyrimidine-5-carboxamide | C28H32FN5O |
| Small Molecule 1 to Inhibit Amyloid Beta Peptide for Alzheimer's Disease | | | Tel Aviv University | | N-(3-chloro-1,4-dihydro-1,4-dioxo-2-naphthalenyl)-L-Tryptophan | |
| Small Molecule to Inhibit ABPP for Alzheimer's Disease | | | Tel Aviv University | | 1,4-naphthoquinon-2-yl-L-tryptophan | |
| Small Molecule to Inhibit Amyloid Precursor Protein for Alzheimer's Disease | | | Cenna Biosciences Inc | | | |
| Small Molecules to Inhibit Amyloid Beta and Tau Protein for Alzheimer's Disease and Tauopathies | | | Treventis Corp | | | |
| Small Molecules to Inhibit Amyloid Beta Peptide for Traumatic Brain Injury and Alzheimer's Disease | | | Madera BioSciences Inc | Oral | | |
| SPG-101 | | | Spinogenix Inc | | | |
| Synthetic Peptide to Inhibit Amyloid Beta for Alzheimer's Disease | | | Leibniz-Institut für Altersforschung Fritz-Lipmann-Institut eV | | | |
| Synthetic Peptide to Inhibit Amyloid Beta Peptide for Alzheimer's Disease | | | NYU Langone Health System | | | |
| Synthetic Peptides to Inhibit Amyloid Beta Protein for Alzheimer's Disease | | | University of Washington | | | |
| THPI-244 | | | Smart Biomolecules Inc | | | |
| TP-70 | | | AfaSci Inc | | | |
| Vaccine to Target Beta-APP42 for Alzheimer's Disease | | | University of Texas Southwestern Medical Center | Parenteral | | |
| AD-1502 | | | BioArctic AB | | | |
| AD-1503 | | | BioArctic AB | | | |
| AD-1801 | | | BioArctic AB | | | |

TABLE X-continued

List of Aβ targeting therapy.

| Drug Name | Generic Name | Brand Name | Company Name | Route of Administration | Chemical Name | Chemical Formula |
|---|---|---|---|---|---|---|
| Antibodies to Inhibit Amyloid Beta for Alzheimer's Disease | | | Denali Therapeutics Inc | Intravenous | | |
| C-1 | | | Rensselaer Polytechnic Institute | | | |
| Drug to Inhibit Amyloid Beta A4 Protein for Alzheimer's Disease | | | Amyloid Solution Inc | | | |
| Gene Therapy to Inhibit Amyloid Beta and Tau Protein for Alzheimer's Disease | | | Lacerta Therapeutics Inc | | | |
| Nanocurcumin | | | The Chinese University of Hong Kong | | | |
| Small Molecule to Inhibit Acetylcholinesterase, Amyloid Beta and MAO-B for Alzheimer's Disease | | | Sun Yat-sen University | | | |
| Small Molecule to Inhibit AChE, BuChE and Amyloid Beta A4 Protein for Alzheimer's Disease | | | Medical University of Lodz | | 6-chloro-N-[2-(2,3-dihydro-1H-cyclo-penta[b]quino-lin-9-ylamino)-hexyl]]-nicotinamide hydrochloride | |
| Small Molecule to Inhibit APP for Alzheimer's Disease | | | Antoxerene Inc | | | |
| Small Molecules to Inhibit Acetylcholinesterase and Amyloid Beta for Alzheimer's Disease | | | FUDAN University | | | |
| Small Molecules to Inhibit Amyloid Beta for Alzheimer's Disease | | | Wren Therapeutics Ltd | | | |
| Small Molecules to Inhibit Amyloid Beta Peptide for Alzheimer's Disease | | | Virginia Commonwealth University | | | |
| Small Molecules to Inhibit Amyloid Beta Protein for Alzheimer's Disease | | | Salk Institute for Biological Studies | | | |
| Small Molecules to Inhibit APP for Alzheimer's Disease | | | AC Immune SA | | | |
| SPG-30X Synthetic Peptide to Inhibit APP for Alzheimer's Disease | | | Spinogenix Inc Ulsan National Institute of Science and Technology | | | |
| Synthetic Peptides to Inhibit | | | Technical University of | | | |

TABLE X-continued

| | | | | Route of | Chemical | Chemical |
|---|---|---|---|---|---|---|
| List of Aβ targeting therapy. | | | | | | |
| Drug Name | Generic Name | Brand Name | Company Name | Administration | Name | Formula |
| ABPP and IAPP for Alzheimer's Disease and Type 2 Diabetes | | | Munich | | | |
| Synthetic Peptides to Inhibit Beta Amyloid for CNS and Metabolic Disorders | | | University of California Los Angeles | | | |
| TE-5315 | | | Immunwork Inc | | | |
| 4-E10 | | | Alterity Therapeutics Ltd | | | |
| 5-E3 | | | Aptevo Therapeutics Inc | | | |
| A-887755 | | | AbbVie Inc | | | |
| AAB-002 | | | Johnson & Johnson | Intravenous | | |
| ABP-102 | | | Abiogen Pharma SpA | | | |
| ACC-002 | | | Johnson & Johnson | Intramuscular | | |
| ACI-636 | | | AC Immune SA | | | |
| ACI-812 | | | AC Immune SA | | | |
| ACU-193 Back-up | | | Acumen Pharmaceuticals Inc | | | |
| ACU-5A5 | | | Acumen Pharmaceuticals Inc | | | |
| ACUCD-00161 | | | Merz Pharma GmbH & Co KgaA | | | |
| ALZT-Patch | | | AZTherapies Inc | Transdermal | | |
| ALZT-QoL | | | AZTherapies Inc | | | |
| ALZTOP-2 | | | AZTherapies Inc | | | |
| AmyTrap-2 | | | Recombinant Technologies LLC | | | |
| AmyTrap-3 | | | Recombinant Technologies LLC | | | |
| AmyTrap-4 | | | Recombinant Technologies LLC | | | |
| ANA-1 | | | Alzhyme Pty Ltd | | | |
| ANA-5 | | | Alzhyme Pty Ltd | | | |
| Antisense RNAi Oligonucleotides to Inhibit Amyloid Precursor Protein and Tau Protein for Alzheimer's Disease | | | University of Iowa | | | |
| ARN-2955 | | | Aria Neurosciences Inc | | | |
| ASN-12 | | | NeuroTransit, Inc. (Inactive) | | | |
| BAN-2203 | | | BioArctic AB | | | |
| BGC20-0406 | | | Senexis Limited (Inactive) | | N,N'-bis(3-hydroxyphenyl) pyridazine-3,6-diamine | C16H14N4O |
| BT-2211 | | | Bioasis Technologies Inc | | | |
| DBT-1339 | | | Medifron DBT Co Ltd | | | |
| DLX-212 | | | Kuur Therapeutics Ltd | | | |
| DP-74 | | Pepticlere | ProteoTech, Inc. (Inactive) | Nasal | | |
| DWP-09031 | | | Daewoong Pharmaceutical Co Ltd | Oral | | |

TABLE X-continued

List of Aβ targeting therapy.

| Drug Name | Generic Name | Brand Name | Company Name | Route of Administration | Chemical Name | Chemical Formula |
|---|---|---|---|---|---|---|
| EDNOL-1 | | | Edunn Biotechnology, Inc. (Inactive) | Intravenous; Nasal; Subcutaneous | | |
| GSK-933776 | | | GlaxoSmithKline Plc | Intramuscular; Intravenous; Subcutaneous | | |
| Haw AD-14 | | | Currax Holdings USA LLC | Oral | | |
| INN-01 | | | Intellect Neurosciences Inc | | | |
| IPS-04 series | | | InnoPharmaScreen Inc | | | |
| JPT-1 | | | Kordate Solutions Inc | | | |
| KU-046 | | | Kareus Therapeutics SA (Inactive) | Oral | | |
| memoquin | | | University of Bologna | | | |
| Monoclonal Antibodies to Inhibit Amyloid Beta for Alzheimer's Disease | | | Immunome Inc | Parenteral | | |
| Monoclonal Antibodies to Inhibit Amyloid Beta Peptide (A beta P or Abeta or Beta Amyloid) for Alzheimer Disease | | | Biogen Inc | | | |
| Monoclonal Antibodies to Inhibit Beta Amyloid Protein 42 for Alzheimer's Disease | | | Mayo Clinic | | | |
| Monoclonal Antibodies to Inhibit Beta Amyloid-40 for Alzheimer's Disease | | | Abzyme Therapeutics LLC | | | |
| Monoclonal Antibody to Inhibit Amyloid beta for Alzheimer's Disease | | | Autonomous University of Barcelona | | | |
| MRZ-8456 | | | Merz Pharma GmbH & Co KgaA | | | |
| MRZ-8676 | | | Merz Pharma GmbH & Co KgaA | Oral | 6,6-dimethyl-2-(2-phenylethynyl)-7,8-dihydroquinolin-5-one | C19H17NO |
| MRZ-9583 | | | Merz Pharma GmbH & Co KgaA | | | |
| NeuAZ-1 | | | Neurim Pharmaceuticals Ltd | | | |
| NHT-0012 | | | Neuro-Hitech, Inc. (Inactive) | | | |
| NP-61 | | | Noscira, S.A. (Inactive) | Oral | | |
| NPT-001 | | | Proclara Biosciences Inc | | | |
| NPT-002 | | | Proclara Biosciences Inc | | | |

TABLE X-continued

| | | | | | | |
|---|---|---|---|---|---|---|
| | | | | List of Aβ targeting therapy. | | |
| Drug Name | Generic Name | Brand Name | Company Name | Route of Administration | Chemical Name | Chemical Formula |
| NPT-007 | | | Proclara Biosciences Inc | | | |
| NPT-014 | | | Proclara Biosciences Inc | | | |
| NPT-289 | | | Proclara Biosciences Inc | | | |
| NS-640 | | | Axoltis Pharma SAS | | | |
| NT4X-167 | | | University of Gottingen | | | |
| PAM-3573 | | | Merz Pharma GmbH & Co KgaA | | | |
| PBT-4 Series | | | Alterity Therapeutics Ltd | | | |
| Peptide to Inhibit Amyloid Beta Peptide for Alzheimer's Disease | | | Merck KGaA | | | |
| PMN-300 | | | ProMIS Neurosciences Inc | | | |
| PMN-320 | | | ProMIS Neurosciences Inc | | | |
| PMN-330 | | | ProMIS Neurosciences Inc | | | |
| PMN-340 | | | ProMIS Neurosciences Inc | | | |
| PMN-350 | | | ProMIS Neurosciences Inc | | | |
| Polysaccharide to Inhibit Amyloid Beta for Alzheimer's Disease | | | ProteoTech, Inc. (Inactive) | | | |
| PPI-1019 | | | GlaxoSmithKline Plc | Intravenous | | |
| PTI-80 | | Exebryl-1 | ProteoTech, Inc. (Inactive) | Oral | | |
| PTI-80 Backup | | | ProteoTech, Inc. (Inactive) | | | |
| PX-106 | | | H. Lundbeck AS | | | |
| QRX-203 | | | ProQR Therapeutics NV | | | |
| SDGII-T200801 | | | Bioalvo SA (Inactive) | | | |
| SEN-1176 | | | Senexis Limited (Inactive) | Oral | | |
| SEN-1276 | | | Senexis Limited (Inactive) | Oral | | |
| SEN-1500 | | | Senexis Limited (Inactive) | Oral | | |
| SEN-1576 | | | Senexis Limited (Inactive) | Oral | | |
| SKPCB-70M | | | SK Chemicals Co Ltd | Oral | | |
| Small Molecule to Inhibit Amyloid Beta Peptide for Alzheimer's Disease | | | Autonomous University of Barcelona | | N-(4-chloro-2-nitrophenyl)-N'-phenylurea | |
| Small Molecule to Inhibit AmyloidBeta Peptide for Alzheimer's Disease | | | Autonomous University of Barcelona | | 2,5-dichloro-N-(4-piperidinophenyl)-3-thiophene-sulfonamide | |
| Small Molecules to Inhibit A-Beta 42 for Alzheimer's | | | University of Texas Southwestern | | | |

TABLE X-continued

| | | | | Route of | Chemical | Chemical |
| --- | --- | --- | --- | --- | --- | --- |
| Drug Name | Generic Name | Brand Name | Company Name | Administration | Name | Formula |
| Disease | | | Medical Center | | | |
| Small Molecules to Inhibit Abeta and NACP for Alzheimer's Disease and Parkinson's Disease | | | Neuropore Therapies Inc | | | |
| Small Molecules to Inhibit Abeta for Alzheimer's Disease | | | Alterity Therapeutics Ltd | | | |
| Small Molecules to Inhibit ADDL Receptor for Alzheimer's Disease | | | Merz Pharma GmbH & Co KgaA | | | |
| Small Molecules to Inhibit Amyloid Beta for Alzheimer's Disease | | | Max Delbruck Center for Molecular Medicine | | | |
| Small Molecules to Inhibit Amyloid Beta Peptide for Alzheimer's Disease | | | Ludwig-Maximilians-University Munich | | | |
| Small Molecules to Inhibit Amyloid Beta Protein for Alzheimer's Disease | | | University of Barcelona | | | |
| Small Molecules to Inhibit Beta-APP40 and Beta-APP42 for Alzheimer's Disease | | | Medisyn Technologies Inc (Inactive) | | | |
| Small Molecules to Inhibits APP for Alzheimer's Disease | | | ModGene Pharma LLC | | | |
| Synthetic Peptides to Inhibit Amyloid Beta Protein for Alzheimer's Disease | | | Louisiana State University | | | |
| TRV-101 | | | Treventis Corp | Oral | | |
| TRV-1140 | | | Treventis Corp | | | |
| TRV-1387 | | | Treventis Corp | Oral | | |
| TRV-217 | | | Treventis Corp | | | |
| V-950 | | | Merck & Co Inc | Intramuscular | | |
| Vaccine to Target Beta Amyloid for Alzheimer's Disease | | | ID Pharma Co Ltd | | | |
| VK-12 | | | Alterity Therapeutics Ltd | | | |
| ALS-499 | | | Advanced Life Sciences Holdings, Inc. (Inactive) | | | |
| ALZ-102 | | | Alzinova AB | | | |
| BI-1034020 | | | Ablynx NV | Intravenous; Subcutaneous | | |
| Drug For Alzheimer's Disease | | | BioChromix Pharma AB | | | |

TABLE X-continued

List of Aβ targeting therapy.

| Drug Name | Generic Name | Brand Name | Company Name | Route of Administration | Chemical Name | Chemical Formula |
|---|---|---|---|---|---|---|
| LuAF-20513 | | | H. Lundbeck AS Otsuka Holdings Co Ltd | Parenteral | | |
| Monoclonal Antibody to Inhibit Abeta for Alzheimer's Disease | | | Eli Lilly and Co | | | |
| SAR-228810 | | | Sanofi | Intravenous; Subcutaneous | | |

In some embodiments, the AD treatment comprises administration of a tau modulating agent. In some embodiments, the tau modulating agent used in the disclosed method is a compound or agent that reduces tau secretion. In some embodiments, the tau modulating agent is a compound or agent that reduces tau deposition. In some embodiments, the tau modulating agent is a compound or agent that reduces tau production. In some embodiments, the tau modulating agent is a compound or agent that reduces tau secretion, deposition or production by more than 10%. In some embodiments, the tau modulating agent is a compound or agent that reduces tau secretion, deposition or production by more than 20%. In some embodiments, the tau modulating agent is a compound or agent that reduces tau secretion, deposition or production by more than 30%. In some embodiments, the tau modulating agent is a compound or agent that reduces tau secretion, deposition or production by more than 40%. In some embodiments, the tau modulating agent is a compound or agent that reduces tau secretion, deposition or production by more than 50%. In some embodiments, the tau modulating agent is a compound or agent that reduces tau secretion, deposition or production by more than 60%. In some embodiments, the tau modulating agent is a compound or agent that reduces tau secretion, deposition or production by more than 70%. In some embodiments, the tau modulating agent is a compound or agent that reduces tau secretion, deposition or production by more than 80%. In some embodiments, the tau modulating agent is a compound or agent that reduces tau secretion, deposition or production by more than 90%. In some embodiments, the tau modulating agent is a compound or agent chosen from PP2A activators such as memantine and sodium selenite, GSK3β inhibitors such as tideglusib and lithium chloride, acetylation inhibitors such as salsalate, OGA inhibitors such as MK-8719, aggregation inhibitors such as LMTX and curcumin, microtubule stabilizers such as epithilone D, NAP and TPI 287, and PDE4 inhibitors such as BPN14770. In some embodiments, the AD treatment is administration of a tau vaccine. A list of tau targeting therapy is provided in Table Y below.

TABLE Y

List of tau targeting therapy.

| Drug Name | Generic Name | Brand Name | Company Name | Route of Administration | Chemical Name | Chemical Formula |
|---|---|---|---|---|---|---|
| RV-02 | | | Intellect Neurosciences Inc | | | |
| RV-03 | | | Intellect Neurosciences Inc | | | |
| ANVS-401 | | Posiphen | Annovis Bio Inc | Oral | [(3aR,8bS)-3,4,8b-trimethyl-2,3a-dihydro-1H-pyrrolo[2,3-b]indol-7-yl] N-phenylcarbamate | C20H23N3O2 |
| hydromethylthionine mesylate | hydromethyl-thionine mesylate | LMTX | TauRx Therapeutics Ltd | Oral | [7-(dimethyl-amino)pheno-thiazin-3-ylidene]-dimethylazanium chloride | C16H18N3SCl |
| gosuranemab | gosuranemab | | Biogen Inc | Intravenous | | C6434H9930N1706O2014S48 |
| BMS-241027 | | | Bristol-Myers Squibb Co | Intravenous | (4S,7R,8S,9S,13Z,16S)-4,8-dihydroxy-5,5,7,9,13-pentamethyl-16-[(E)-1-(2-methyl-1,3- | C27H41NO5S |

TABLE Y-continued

| | | | | | | |
|---|---|---|---|---|---|---|
| | | | | | List of tau targeting therapy. | |
| Drug Name | Generic Name | Brand Name | Company Name | Route of Administration | Chemical Name | Chemical Formula |
| | | | | | thiazol-4-yl)prop-1-en-2-yl]-1-oxacyclohexa-dec-13-ene-2,6-dione | |
| zagotenemab | zagotenemab | | Eli Lilly and Co | Intravenous; Subcutaneous | Immunoglobulin G4, anti-(Tau protein) (human monoclonal LY3303560 ?4-chain), disulfide with human monoclonal LY3303560 light chain, dime | C6448H9976N1712O2026S44 |
| tilavonemab | tilavonemab | | AbbVie Inc | Intravenous | Immunoglobulin G4, anti-(human tau protein) (human-Mus musculus monoclonal PR-1649264 y4-chain), disulfide with human-Mus musculus monoclonal PR-1649264 k-chain, dimer | C6480H9956N1720O2028S42. (nonglycosylated) |
| davunetide | davunetide | | Coronis NeuroSciences Ltd | Intravenous; Nasal; Subcutaneous | (2R)-2-amino-5-[[(2R)-1-[[(2R,3R)-2-[[(2R)-2-[[(2R)-2-[[(2R)-1-[(2R)-2-[(2R)-2,4-diamino4 (2S)-5-amino-2-[[(2S)-1-[(2S,3S)-2-[(2S)-2-[[(2S)-2-[[(2S)-1-[(2S)-2-[[(2S)-2,4-diamino-4-oxobutanoyl] amino]propanoyl]pyr-rolidine-2-carbonyl]amino]-3-methyl-butanoyl]amino]-3-hydroxy-propanoyl]amino]-3-methylpentanoyl]pyr-rolidine-2-carbonyl]amino]-5-oxopentanoic acid | C36H60N10O12 |
| semorinemab | semorinemab | | Genentech USA Inc Chugai Pharmaceutical Co Ltd | Intravenous; Parenteral | Immunoglobulin G4, anti-(human tau protein) (human-Mus musculus monoclonal RO7105705 | C6454H99 46N1710O 2026S42 |

TABLE Y-continued

| | | | | | | |
|---|---|---|---|---|---|---|
| | | | | | List of tau targeting therapy. | |

| Drug Name | Generic Name | Brand Name | Company Name | Route of Administration | Chemical Name | Chemical Formula |
|---|---|---|---|---|---|---|
| | | | | | gamma4-chain), disulfide with human-Mus musculus monoclonal RO7105705 kappa-chain, dimer | |
| TRx-0014 | Methyl-thioninium chloride [INN] | Rember | TauRx Therapeutics Ltd | Oral | [7-(dimethyl-amino)pheno-thiazin-3-ylidene]-dimethylazanium chloride | C16-H18-N3-S.CI |
| (curcumin + paclitaxel) | paclitaxel | | Augustus Bio Target Inc | | curcumin: (1E, 6E)-1,7-bis(4-hydroxy-3-methoxy-phenyl)hepta-1,6-diene-3,5-dione; paclitaxel: (2a,5b,7b,10b,13a)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate | curcumin:C21H20O6; paclitaxel: C47H51N O14 |
| AADvac-1 | | | Axon Neuroscience SE | Subcutaneous | | |
| AV-1980D | | | Capo Therapeutics Inc | | | |
| ACI-35 | | | AC Immune SA | Parenteral | | |
| ACI-35030 | | | AC Immune SA | | | |
| Vaccine to Target Tau for Alzheimer's Disease and Parkinson's Disease | | | University of Texas Medical Branch at Galveston | | | |
| AV-1991CP | | | Capo Therapeutics Inc | | | |
| AV-1980R | | | Capo Therapeutics Ino | | | |
| AV-1992CP | | | Capo Therapeutics Inc | | | |
| Vaccine to Target Tau for Alzheimer's Disease and Chronic Traumatic Encephalopathy | | | United Neuroscience Ltd | | | |
| Vaccine to Target Tau for Alzheimer's Disease | | | Tria Bioscience Corp | | | |
| YM-7555 | | | Vitruvian Biomedical Inc | | | |
| TRV-1387 | | | Treventis Corp | Oral | | |
| Antisense Oligonucleotide to Inhibit Tau Protein for Neurodegenerative Disorders | | | Washington University in St Louis | | | |
| CB-301 | | | Cantabio Pharmaceuticals Inc | Oral | | |

TABLE Y-continued

| | | | | | | |
|---|---|---|---|---|---|---|
| | | | | List of tau targeting therapy. | | |
| Drug Name | Generic Name | Brand Name | Company Name | Route of Administration | Chemical Name | Chemical Formula |
| T-01OX2 | | | Intellect Neurosciences Inc | | | |
| ACI-3024 Monoclonal Antibodies to Inhibit tau Protein for Alzhiemer's Disease and Progressive Supranuclear Palsy | | | Eli Lilly and Co UCB SA | Oral | | |
| PTI-80 Backup | | | Proteo Tech, Inc. (Inactive) | | | |
| DDNA-0101 | | | Dadang & BIO Co Ltd | | | |
| PNT-001 | | | Pinteon Therapeutics Inc | Intravenous | | |
| Small Molecule to Inhibit Tau Oligomer for Alzheimer's Disease and Frontotemporal Dementia | | | Oligomerix inc | | | |
| Antibody to Inhibit Tau Oligomer for Alzheimer's Disease | | | Oligomerix inc | | | |
| CLR-01 | | | University of California Los Angeles | | | |
| Monoclonal Antibody to Inhibit Tau for Central Nervous System Disorders | | | LA Cell Inc | | | |
| Drugs to Inhibit Amyloid Beta Protein and Tau for Alzheimer's Disease | | | Ovensa Inc | | | |
| Gene Therapy To Inhibit Tau for Dementia and Neurodegenerative Diseases | | | Voyager Therapeutics Inc | Intravenous | | |
| Drug to Inhibit Tau for Alzheimer's Disease | | | Medifron DBT Co Ltd | | | |
| Memrin | | Memrin | LSL Neurosciences LLC | | | |
| Small Molecule to Inhibit Tau Protein for Alzheimer's Disease and Tauopathies | | | ALS Biopharma LLC | | | |
| Monoclonal Antibodies to Inhibit Tau for CNS Disorders | | | New York University | | | |
| AADvac-2 | | | Axon Neuroscience SE Prothena Corp Plc | | | |
| Antibodies to Inhibit Tau Protein for Alzheimer's Disease and Tauopathies | | | | | | |
| LuAF-87908 Monoclonal Antibodies to Inhibit MAPT for Alzheimer's Disease | | | H. Lundbeck AS Covalent Bioscience Inc | Intravenous | | |
| Gene Therapy to Inhibit Amyloid Beta and Tau Protein for Alzheimer's Disease | | | Lacerta Therapeutics Inc | | | |
| PTI-80 | | Exebryl-1 | Proteo Tech, Inc. (Inactive) | Oral | | |
| BIIB-076 Bispecific | | | Biogen Inc Denali | Intravenous | | |

TABLE Y-continued

List of tau targeting therapy.

| Drug Name | Generic Name | Brand Name | Company Name | Route of Administration | Chemical Name | Chemical Formula |
|---|---|---|---|---|---|---|
| Monoclonal Antibodies to Inhibit MAPT for Alzheimer's Disease | | | Therapeutics Inc | | | |
| Small Molecule 1 to Inhibit Tau for Alzheimer's Disease | | | TauRx Therapeutics Ltd | | | |
| Small Molecule to Inhibit MAPT for Alzheimer's Disease | | | Fulcrum Therapeutics Inc | | | |
| Antisense RNAi Oligonucleotides to Inhibit Amyloid Precursor Protein and Tau Protein for Alzheimer's Disease | | | University of Iowa | | | |
| Antibodies to Inhibit Tau for Alzheimer's Disease and Tauopathies | | | Aprinoia Therapeutics Inc | | | |
| PTI-51CH3 | | TauPro | Proteo Tech, Inc. (Inactive) | | | |
| IONIS-MAPTRx | | | Biogen Inc | Intrathecal | | |
| TRV-101 | | | Treventis Corp | Oral | | |
| Small Molecule to Inhibit Tau for Alzheimer's Disease and Tauopathies | | | Aprinoia Therapeutics Inc | | | |
| ADELY-01 | | | ADEL Inc | | | |
| Small Molecule to Inhibit Microtubule Associated Protein Tau for Alzheimer's Disease and Progressive Supranuclear Palsy | | | Arvinas Inc | | | |
| ReS-10T | | | reMYND NV | | | |
| Small Molecules to Inhibit Tau for Alzheimer Disease and Tauopathies | | | University of Michigan | | | |
| NPT-289 | | | Proclara Biosciences Inc | | | |
| NPT-088 | | | Proclara Biosciences Inc | Intravenous | | |
| Monoclonal Antibodies to Inhibit Tau for Neurology | | | Prothena Corp Plc | | | |
| ANVS-405 | | | Annovis Bio Inc | Intravenous | | |
| Small Molecules to Inhibit Amyloid Beta and Tau Protein for Alzheimer's Disease and Tauopathies | | | Treventis Corp | | | |
| RIV-1061 | | | Revivo Therapeutics Inc | | | |
| ReS-19T | | | reMYND NV | | | |
| Ta-1505 | | | Merck & Co Inc | | | |
| E-2814 | | | Eisai Co Ltd | | | |
| Monoclonal Antibody to Inhibit Tau for Alzheimer's Disease | | | Johnson & Johnson | | | |
| Antibody to Inhibit Tau for Alzheimer's Disease | | | ICB International Inc | Intravenous | | |
| Small Molecules to Inhibit MAPT for Alzhiemer's Disease | | | ADRx Inc | | | |
| NPT-002 | | | Proclara Biosciences Inc | | | |
| SEL-141 | | | Ryvu Therapeutics SA | | | |
| SRN-003556 | | | KeyNeurotek Pharmaceuticals AG (Inactive) | Oral | | |

TABLE Y-continued

List of tau targeting therapy.

| Drug Name | Generic Name | Brand Name | Company Name | Route of Administration | Chemical Name | Chemical Formula |
|---|---|---|---|---|---|---|
| SDGI-T200801 | | | Bioalvo SA (Inactive) | | | |
| SDGII-T200801 | | | Bioalvo SA (Inactive) | | | |
| Monoclonal Antibody Drug Conjugate to Inhibit Tau for Alzheimer's Disease | | | Innosense LLC | Nasal | | |
| Monoclonal Antibodies to Inhibit Tau for Alzheimer's Disease | | | ProMIS Neurosciences Inc | | | |
| Small Molecule to Inhibit Tau for Alzheimer's Disease | | | Centre National de la Recherche Scientifique | | | |
| Small Molecules to Inhibit Tau for Alzheimer's Disease | | | University of Dundee | | | |
| AA-7 | | | Cesa Alliance SA | | | |
| ReS-3T | | | reMYND NV | | | |
| TRV-217 | | | Treventis Corp | | | |
| BEY-2153 | | | BeyondBio Inc | Oral | | |
| Bispecific Monoclonal Antibodies to Inhibit BACE1 and MAPT for Alzheimer's Disease | | | Denali Therapeutics Inc | | | |
| Antibody to Inhibit P-Tau for Alzheimer's Disease | | | ICB International Inc | | | |
| NHT-0012 | | | Neuro-Hitech, Inc. (Inactive) | | | |
| NPT-001 | | | Proclara Biosciences Inc | | | |
| Small Molecules to Inhibit Tau for Alzheimer's Disease and Tauopathies | | | Aprinoia Therapeutics Inc | | | |
| ST-501 | | | Biogen Inc | | | |
| NNI-3 | | | Neuronautics, Inc. (Inactive) | | | |
| NNI-5 | | | Neuronautics, Inc. (Inactive) | | | |
| Monoclonal Antibody for Central Nervous System | | | Beth Israel Deaconess Medical Center | | | |
| NPT-189 | | | Proclara Biosciences Inc | Intravenous | | |
| TRV-1140 | | | Treventis Corp | | | |
| Gene Therapy to Inhibit MAPT for Alzheimer's Disease and Tauopathies | | | Neurimmune Holding AG | | | |
| VYTAU-01 | | | Voyager Therapeutics Inc | | | |
| JNJ-3657 | | | Johnson & Johnson | Intravenous | | |
| Monoclonal Antibodies to Inhibit Tau, Amyloid Beta and Alpha-Synuclein for Neurodegenerative Diseases | | | NYU Langone Health System | | | |
| Small Molecule to Inhibit Tau for Alzheimer's Disease | | | TauRx Therapeutics Ltd | | | |
| BLV-0703 | | | Bioalvo SA (Inactive) | | | |
| IPN-002 | | | Bristol-Myers Squibb Co | Parenteral | | |

TABLE Y-continued

List of tau targeting therapy.

| Drug Name | Generic Name | Brand Name | Company Name | Route of Administration | Chemical Name | Chemical Formula |
|---|---|---|---|---|---|---|
| ReS-8T<br>Monoclonal<br>Antibodies to Inhibit<br>Tau Protein for<br>Neurodegenerative<br>Diseases | | | reMYND NV<br>Bristol-Myers<br>Squibb Co | | | |

In some embodiments, the disclosure relates to a method of analyzing Aβ protein and tau protein depositions in the brain of a subject, the method comprising: a) imaging the brain of the subject as disclosed elsewhere herein; b) analyzing Aβ protein deposition in at least one region within the brain of the subject as disclosed elsewhere herein; (c) analyzing tau protein deposition in at least one region within the brain of the subject as disclosed elsewhere herein; and (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject using the algorithms disclosed elsewhere herein; (e) comparing the first normalized score to a first threshold and comparing a second normalized score to a second threshold; wherein the first threshold is calculated relative to a first control dataset and the second threshold is calculated relative to a second control. Depending upon the comparing results of step (e) relative to the first and/or second threshold, the degree of severity of a neurodegenerative disorder (e.g., AD) in the subject can be predicted. In some embodiments, the images of the subject's brain are taken by PET scan. In some embodiments, the images of the subject's brain are taken by MRI scan. In some embodiments, the subject is a healthy subject. In some embodiments, the subject is at risk of developing a neurodegenerative disorder (e.g., AD). In some embodiments, the subject is suspected of having AD. In some embodiments, the subject is diagnosed of having AD. In some embodiments, the subject is predicted to have low risk of developing a neurodegenerative disorder (e.g., AD) if the normalized first and second scores of step (d) comprise a low degree of interactions between ERC neural tissue with tau protein deposition and non-ERC neural tissue with Aβ protein deposition and a low degree of local interactions between tau protein deposition and Aβ protein deposition within the ITG. In some embodiments, the subject is predicted to have developed an early stage neurodegenerative disorder (e.g., AD) if the normalized first and second scores of step (d) comprise a high degree of interactions between ERC neural tissue with tau protein deposition and non-ERC neural tissue with Aβ protein deposition and a low degree of local interactions between tau protein deposition and Aβ protein deposition within the ITG. In some embodiments, the subject is predicted to have developed a more severe degree of neurodegenerative disorder (e.g., AD) if the normalized first and second scores of step (d) comprise a high degree of interactions between ERC neural tissue with tau protein deposition and non-ERC neural tissue with Aβ protein deposition and a high degree of local interactions between tau protein deposition and Aβ protein deposition within the ITG.

In some embodiments, the disclosure relates to a method of analyzing brain images of a subject, the method comprising: a) imaging the brain of the subject as disclosed elsewhere herein; b) analyzing Aβ protein deposition in at least one region within the brain of the subject as disclosed elsewhere herein; (c) analyzing tau protein deposition in at least one region within the brain of the subject as disclosed elsewhere herein; and (d) calculating a first normalized score corresponding to interaction of Aβ protein deposition and tau protein deposition in a first region of the brain, and calculating a second normalized score corresponding to interaction of Aβ protein deposition and tau protein deposition in a second region of the brain of the subject using the algorithms disclosed elsewhere herein; (e) comparing the first normalized score to a first threshold and comparing a second normalized score to a second threshold; wherein the first threshold is calculated relative to a first control dataset and the second threshold is calculated relative to a second control. In some embodiments, the images of the subject's brain are taken by PET scan. In some embodiments, the images of the subject's brain are taken by MRI scan. In some embodiments, the subject is a healthy subject. In some embodiments, the subject is at risk of developing a neurodegenerative disorder (e.g., AD). In some embodiments, the subject is healthy or suspected of having AD. In some embodiments, the subject is diagnosed of having AD.

Systems

The above-described methods can be implemented in any of numerous ways. For example, the embodiments may be implemented using a computer program product (i.e. software), hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may include a memory, coupled to one or more processing units (also referred to herein simply as "processors"), one or more communication interfaces, one or more display units, and one or more user input devices. The memory may include any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. The disclosure also relates to a as a computer readable storage medium comprising executable instructions to perform any Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention disclosed herein. The computer readable medium or media can be transportable, such that the program or programs stored thereon can be loaded onto one or more different computers or other processors to implement various aspects of the present invention as discussed above. In some embodiments, the system comprises cloud-based software that executes one or all of the steps of each disclosed method instruction.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present disclosure need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, the disclosure relates to various embodiments in which one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

In some embodiments, the disclosure relates to a computer-implemented method of determining the responsiveness of a subject to an agent affecting AD, the method comprising: identifying a subject responsive to an Alzheimer's disease (AD) treatment comprising: (a) imaging a brain of the subject; (b) analyzing protein deposition of amyloid protein in at least one region within the brain of the subject; (c) analyzing protein deposition of tau protein in at least one region within the brain of the subject; (d) calculating a first normalized score corresponding to interaction of amyloid and tau deposition in a first region of the brain, and calculating a second normalized score corresponding to interaction of amyloid and tau deposition in a second region of the brain of the subject. In some embodiments, the method comprises analyzing and/or imaging the brain. In some embodiments, the method comprises analyzing an image of the brain to quantify the amount of tau protein and amyloid protein deposition in the brain of a subject. In some embodiments, the methods of the disclosure comprise a step of analyzing the quantity of the tau and amyloid deposition in the ITG region of the brain of a subject. In some embodiments, the disclosure relates to a system comprising a processor that performs a computer-implemented method of detecting protein deposition of tau and amyloid proteins in the brain of a subject. In some embodiments, the system comprises with a program product with instructions for a user device that accesses the internet, the method comprising: detecting amyloid and/or tau protein deposition in the image of a brain of a subject. In some embodiments, the methods and software products comprise methods of accessing a webpage; detecting and/or analyzing amyloid and/or tau protein deposition in the image of a brain of a subject displayed on the webpage. In some embodiments, the disclosure relates to a system comprising a processor that performs a computer-implemented method of amyloid and/or tau protein deposition in the image of a brain of a subject displayed on a user device that accesses the internet, the method comprising: detecting a user accessing a webpage;

detecting and/or quantifying an amount of tau protein deposition and amyloid protein deposition of an image of a brain on the webpage, and, calculating a first normalized score corresponding to interaction of amyloid and tau deposition in a first region of the brain, and calculating a second normalized score corresponding to interaction of amyloid and tau deposition in a second region of the brain of the subject. In some embodiments, the first region of the brain is the ITG. In some embodiments, the first and second regions of the brain are the ITG. In some embodiments, the first region of the brain is the ITG and the second region of the brain is a region of the brain other than the ITG. In some embodiments, the first region of the brain is ITG and the second region of the brain is the neocortex.

Computer-implemented embodiments of the disclosure relate to methods of determining a subject likely to respond to AD disease modifying agents comprising steps of. (e) comparing the first normalized score to a first threshold relative to a first control dataset of a sample and comparing a second normalized score to a second threshold relative to a control dataset of the sample; and (f) classifying the subject as being likely to respond to an AD treatment based upon results of comparing of step (e) relative to the first and/or second threshold; wherein each of steps (e) and (f) are performed after step (d).

In some embodiments, the disclosure relates to a system that comprises at least one processor, a program storage, such as memory, for storing program code executable on the processor, and one or more input/output devices and/or interfaces, such as data communication and/or peripheral devices and/or interfaces. In some embodiments, the user device and computer system or systems are communicably connected by a data communication network, such as a Local Area Network (LAN), the Internet, or the like, which may also be connected to a number of other client and/or server computer systems. The user device and client and/or server computer systems may further include appropriate operating system software.

In some embodiments, components and/or units of the devices described herein may be able to interact through one or more communication channels or mediums or links, for example, a shared access medium, a global communication network, the Internet, the World Wide Web, a wired network, a wireless network, a combination of one or more wired networks and/or one or more wireless networks, one or more communication networks, an a-synchronic or asynchronous wireless network, a synchronic wireless network, a managed wireless network, a non-managed wireless network, a burstable wireless network, a non-burstable wireless network, a scheduled wireless network, a non-scheduled wireless network, or the like.

Discussions herein utilizing terms such as, for example, "processing," "computing," "calculating," "determining," or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

Some embodiments may take the form of an entirely hardware embodiment, an entirely software embodiment, or an embodiment including both hardware and software elements. Some embodiments may be implemented in software, which includes but is not limited to firmware, resident software, microcode, or the like.

Furthermore, some embodiments may take the form of a computer program product accessible from a computer-usable or computer-readable medium providing program code for use by or in connection with a computer or any instruction execution system. For example, a computer-usable or computer-readable medium may be or may include any apparatus that can contain, store, communicate, propagate, or transport the program for use by or in connection with the instruction execution system, apparatus, or device.

In some embodiments, the medium may be or may include an electronic, magnetic, optical, electromagnetic, InfraRed (IR), or semiconductor system (or apparatus or device) or a propagation medium. Some demonstrative examples of a computer-readable medium may include a semiconductor or solid state memory, magnetic tape, a removable computer diskette, a Random Access Memory (RAM), a Read-Only Memory (ROM), a rigid magnetic disk, an optical disk, or the like. Some demonstrative examples of optical disks include Compact Disk-Read-Only Memory (CD-ROM), Compact Disk-Read/Write (CD-R/W), DVD, or the like.

In some embodiments, a data processing system suitable for storing and/or executing program code may include at least one processor coupled directly or indirectly to memory elements, for example, through a system bus. The memory elements may include, for example, local memory employed during actual execution of the program code, bulk storage, and cache memories which may provide temporary storage of at least some program code in order to reduce the number of times code must be retrieved from bulk storage during execution.

In some embodiments, input/output or I/O devices (including but not limited to keyboards, displays, pointing devices, etc.) may be coupled to the system either directly or through intervening I/O controllers. In some embodiments, network adapters may be coupled to the system to enable the data processing system to become coupled to other data processing systems or remote printers or storage devices, for example, through intervening private or public networks. In some embodiments, modems, cable modems and Ethernet cards are demonstrative examples of types of network adapters. Other suitable components may be used.

Some embodiments may be implemented by software, by hardware, or by any combination of software and/or hardware as may be suitable for specific applications or in accordance with specific design requirements. Some embodiments may include units and/or sub-units, which may be separate of each other or combined together, in whole or in part, and may be implemented using specific, multi-purpose or general processors or controllers. Some embodiments may include buffers, registers, stacks, storage units and/or memory units, for temporary or long-term storage of data or in order to facilitate the operation of particular implementations.

Some embodiments may be implemented, for example, using a machine-readable medium or article which may store an instruction or a set of instructions that, if executed by a machine, cause the machine to perform a method steps and/or operations described herein. Such machine may include, for example, any suitable processing platform, computing platform, computing device, processing device, electronic device, electronic system, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit; for example, memory, removable or non-removable media, erasable or non-erasable media, writeable or re-writeable media, digital or analog media, hard disk drive, floppy disk, Compact Disk Read Only Memory (CD-ROM), Compact Disk Recordable (CD-R), Compact Disk Re-Writeable (CD-RW), optical disk, magnetic media, various types of Digital Versatile Disks (DVDs), a tape, a cassette, or the like. The instructions may include any suitable type of code, for example, source code, compiled code, interpreted code, executable code, static code, dynamic code, or the like, and may be implemented using any suitable high-level, low-level, object-oriented, visual, compiled and/or interpreted programming language, e.g., C, C++, Java™, BASIC, Pascal, Fortran, Cobol, assembly language, machine code, or the like.

Many of the functional units described in this specification have been labeled as circuits, in order to more particularly emphasize their implementation independence. For example, a circuit may be implemented as a hardware circuit comprising custom very-large-scale integration (VLSI) circuits or gate arrays, off-the-shelf semiconductors such as logic chips, transistors, or other discrete components. A circuit may also be implemented in programmable hardware devices such as field programmable gate arrays, programmable array logic, programmable logic devices or the like.

In some embodiment, the circuits may also be implemented in machine-readable medium for execution by various types of processors. An identified circuit of executable code may, for instance, comprise one or more physical or logical blocks of computer instructions, which may, for instance, be organized as an object, procedure, or function. Nevertheless, the executables of an identified circuit need not be physically located together, but may comprise disparate instructions stored in different locations which, when joined logically together, comprise the circuit and achieve the stated purpose for the circuit. Indeed, a circuit of computer readable program code may be a single instruction, or many instructions, and may even be distributed over several different code segments, among different programs, and across several memory devices. Similarly, operational data may be identified and illustrated herein within circuits, and may be embodied in any suitable form and organized within any suitable type of data structure. The operational data may be collected as a single data set, or may be distributed over different locations including over different storage devices, and may exist, at least partially, merely as electronic signals on a system or network.

The computer readable medium (also referred to herein as machine-readable media or machine-readable content) may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing. As alluded to above, examples of the computer readable storage medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. As also alluded to above, computer readable program code embodied on a computer readable signal medium may be transmitted using any appropriate medium, including but not limited to wireless, wireline, optical fiber cable, Radio Frequency (RF), or the like, or any suitable combination of the foregoing. In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on a user's computer, partly on the user's computer, as a stand-alone computer-readable package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

Functions, operations, components and/or features described herein with reference to one or more embodiments, may be combined with, or may be utilized in combination with, one or more other functions, operations, components and/or features described herein with reference to one or more other embodiments, or vice versa.

Although the disclosure has been described with reference to exemplary embodiments, it is not limited thereto. Those skilled in the art will appreciate that numerous changes and modifications may be made to the preferred embodiments of the disclosure and that such changes and modifications may be made without departing from the true spirit of the disclosure. It is therefore intended that the appended claims be construed to cover all such equivalent variations as fall within the true spirit and scope of the disclosure.

All referenced journal articles, patents, and other publications are incorporated by reference herein in their entireties.

EXAMPLES

Example 1. Materials and Methods

Examples 2-5 were carried out with materials and methods including, but not limited to, the following.

Participants

We included participants from two non-overlapping datasets for this study: the discovery dataset and the validation dataset. The discovery dataset consisted of participants from the Alzheimer's Disease Neuroimaging Initiative (ADNI, http://adni.loni.usc.edu/) and includes patients with AD-type dementia, mild cognitive impairment (MCI), and cognitively normal age-matched controls. All participants underwent structural magnetic resonance imaging (MRI) scans and positron emission tomography (PET) using $^{18}$F-florbetapir (AV45) for Aβ and $^{18}$F-flortaucipir (AV1451) scans for tau. 187 cognitively normal (CN) subjects, 64 patients with early MCI (early MCI), 30 patients with late MCI (late MCI), and 11 patients with AD dementia were used for the discovery dataset. Detailed diagnostic criteria were previously reported (http://adni.loni.usc.edu/methods/).[4] Of the 292 subjects available, four CN subjects, one early MCI patient, and two AD-type dementia patients were excluded due to poor co-registration quality between MRI and PET scans. One early MCI patient and one CN subject were excluded due to poor pre-processing during Freesurfer-based image analysis. We also included 95 CN subjects from ADNI to construct the healthy structural connectome. These participants satisfied identical diagnostic criteria as the previous CN subjects but were chosen because they had undergone structural MRI scans and diffusion-weighted MRI (DWI) scans suitable for diffusion tractography. Of these 95 subjects, 49 were also included in the discovery dataset used for PET analysis.

The validation dataset included participants clinically diagnosed at Gangnam Severance Hospital, South Korea, from January 2015 to July 2016. All participants in the validation dataset underwent structural MRI, as well as $^{18}$F-florbetaben PET for Aβ and $^{18}$F-flortaucipir PET for tau. The participants included 96 CN subjects showing normal performance on neuropsychological tests and no abnormalities on brain MRI, as well as 84 patients with amnestic MCI (aMCI) and 71 with AD-type dementia fulfilling the National Institute on Aging-Alzheimer Association diagnostic criteria for "MCI due to AD with intermediate or high likelihood"[5] and "probable dementia with evidence of the AD pathophysiologic process"[6], respectively. Detailed diagnostic criteria for all three clinical groups have been described[7].

For longitudinal analyses, additional image data from the ADNI repository was downloaded in January 2021. All participants had baseline scans satisfying the same criteria used for the cross-sectional analyses and had undergone follow-up structural MRI and flortaucipir PET scans. Due to the limited samples available, all MCI subjects were included and early and late MCI subjects were considered together. With 19 newly added subjects after excluding 4 due to image co-registration errors, 72 CN subjects, 55 patients with MCI (amyloid-PET-positive: 32), and 8 patients with AD dementia were available for the ADNI discovery dataset. In the Korean validation dataset, 169 participants including 74 CN subjects, 59 patients with amnestic MCI (amyloid-PET-positive: 36), and 36 patients with dementia (amyloid-PET-positive: 28) had follow-up scans. After calculating mean annualized change in tau-PET W-scores across all ROIs, four subjects with extreme outlier values, defined as any values more than 3 times the interquartile range above the third quartile, were removed from the longitudinal analyses.

The demographic and clinical characteristics of the study population, the ADNI discovery dataset, the Korean validation dataset, and the Longitudinal dataset are summarized in Table 1 below.

TABLE 1

Demographic and clinical characteristics of the overall study population ("CN": cognitively normal; "early MCI": early mild cognitive impairment; "late MCI": late mild cognitive impairment; "MMSE": mini-mental state examination; "CDR SOB": clinical dementia rating sum-of-boxes). Data are presented as mean ± standard deviation for continuous variables and number (%) for nominal variables. Independent Kruskal-Wallis test for continuous variables and chi square test for nominal variables.

| | ADNI discovery dataset | | | | |
|---|---|---|---|---|---|
| Variables | CN (n = 182) | Early MCI (n = 62) | Late MCI (n = 30) | AD (n = 9) | Group comparison p-value (statistics) |
| Age (years) | 75.29 ± 7.77 | 75.79 ± 6.82 | 74.77 ± 7.56 | 69.56 ± 10.0 | 0.309 |
| Sex (female, n [%]) | 105 (57.7) | 24 (38.7) | 13 (43.3) | 3 (33.3) | 0.032 (8.835) |
| Education (years) | 16.63 ± 2.52 | 16.40 ± 2.74 | 16.67 ± 2.68 | 15.44 ± 2.24 | 0.496 |
| MMSE | 28.96 ± 1.32 | 27.43 ± 3.13 | 25.63 ± 5.56 | 21.44 ± 1.67 | <0.001 |
| CDR SOB | 0.16 ± 0.52 | 1.98 ± 2.47 | 2.97 ± 3.56 | 3.83 ± 1.62 | <0.001 |
| Amyloid positivity (%)* | 67 (36.8) | 28 (45.2) | 17 (56.7) | 9 (100.0) | <0.001 (17.194) |

| | Korean validation dataset | | | |
|---|---|---|---|---|
| Variables | CN (n = 96) | aMCI (n = 84) | AD (n = 71) | Group comparison p-value (statistics) |
| Age (years) | 66.31 ± 9.49 | 71.32 ± 9.12 | 74.37 ± 9.35 | <0.001 |
| Sex (female, n [%]) | 60 (66.7) | 51 (60.7) | 54 (76.1) | 0.093 (4.744) |
| Education (years) | 11.94 ± 4.54 | 11.46 ± 4.26 | 9.77 ± 5.72 | 0.047 |

TABLE 1-continued

Demographic and clinical characteristics of the overall study population ("CN": cognitively normal; "early MCI": early mild cognitive impairment; "late MCI": late mild cognitive impairment; "MMSE": mini-mental state examination; "CDR SOB": clinical dementia rating sum-of-boxes). Data are presented as mean ± standard deviation for continuous variables and number (%) for nominal variables. Independent Kruskal-Wallis test for continuous variables and chi square test for nominal variables.

| | | | | |
|---|---|---|---|---|
| MMSE | 28.19 ± 1.78 | 25.63 ± 2.80 | 19.08 ± 5.33 | <0.001 |
| CDR SOB | 0.00 ± 0.00 | 1.61 ± 1.01 | 5.01 ± 2.54 | <0.001 |
| Amyloid positivity (%)* | 9 (9.4) | 45 (53.6) | 56 (78.9) | <0.001 (84.947) |

| | Longitudinal dataset | | | |
|---|---|---|---|---|
| Variables | CN (n = 146) | MCI (n = 114) | AD (n = 44) | Group comparison p-value (statistics) |
| N (ADNI/Korean) | 72/74 | 55/59 | 8/36 | <0.001 (14.363) |
| Follow-up (years) | 1.84 ± 0.53 | 1.69 ± 0.49 | 1.86 ± 0.41 | 0.016 |
| Age (years) | 71.25 ± 9.70 | 72.82 ± 7.49 | 73.50 ± 9.34 | 0.143 |
| Sex (female, n [%]) | 88 (60.3) | 59 (51.8) | 30 (68.2) | 0.135 (4.008) |
| Education (years) | 14.22 ± 4.16 | 13.73 ± 4.46 | 10.27 ± 5.74 | <0.001 |
| MMSE | 28.59 ± 1.60 | 26.46 ± 3.27 | 20.52 ± 4.15 | <0.001 |
| CDR SOB | 0.12 ± 0.46 | 1.38 ± 1.31 | 4.39 ± 1.64 | <0.001 |
| Amyloid positivity (%)* | 40 (27.4) | 68 (59.6) | 36 (81.8) | <0.001 (51.199) |

*Note that only amyloid-PET-positive subjects were included in subsequent analyses.

Image Acquisition

For the discovery (ADNI) dataset, structural MRI and PET scans were downloaded on April 2019 from the ADNI repository. Structural MRIs were acquired in ADNI-2 and ADNI-3 phases using 3T MIRI scanners with 3D magneti-zation-prepared rapid gradient echo (MIP-RAGE) or inver-sion recovery-fast spoiled gradient recalled (TR-SPGR) sequences. Detailed protocols of MIRI scanner for T1-weighted imaging can be found online (http://adni.lo-ni.usc.edu/methods/documents/mri-protocols/). Florbetapir PET scans were acquired for 20 minutes (4×5 min frames) at 50-70 min post injection of 10 mCi tracers, and Flo-rtaucipir PET scans were acquired for 30 min (6×5 min frames) at 75-105 min post injection of 10 mCi tracers. We only used MIRI scans having the shortest interval between MIRI and Flortaucipir PET acquisition, all within six months (37±40 days) of each other. Florbetapir images were used if acquired within 1 year of Flortaucipir (23±38 days), in keeping with previous approaches[8,9] (see Table 2 below). DWI had the same acquisition date as the corresponding T1-weighted MRI. Multiple b=0 s/mm$^2$ images and 48 b=1000 s/mm$^2$ images were acquired for DWI with 2×2×2 mm$^3$ voxels in ADNI-3 phase (http://adni.loni.usc.edu/meth-ods/). In the validation (Korean) dataset, T1-weighted MRI was also obtained using a 3T MR scanner with 3D SPGR sequence. Each of the Florbetaben and Flortaucipir PET scans was acquired for 20 minutes on separate days at 90 min and 80 minutes after the injection of tracers, respec-tively. Detailed acquisition parameters have been described[7].

TABLE 2

Scan time interval between each pair of modalities.

| MRI - Flortaucipir PET | MRI - Florbetapir PET | Flortaucipir - Florbetapir PET |
|---|---|---|
| 39 ± 42 days (up to 176 days) | 32 ± 45 days (up to 356 days) | 22 ± 38 days (up to 365 days) |

PET Quantification

Each Aβ- and tau-PET image was preprocessed as fol-lows. The raw PET image was first co-registered between frames to reduce motion effects with conversion to DICOM format and processed by averaging five-minute frames. The generated images were then reoriented into a standard 160×160×96 voxel image grid with 1.5 mm cubic voxels and intensity normalized. Finally, smoothing was performed with a scanner-specific filter function to make a uniform isotropic resolution of 8 mm full width at half maximum[10] (http://adni.loni.usc.edu/). PET images were co-registered to the corresponding T1 image using FMRIB Software Library (FSL) Linear Registration Tool (FLIRT). For each hemi-sphere, we used the atlas parcellation comprising 105 cere-bral cortical and 18 subcortical brain regions defined by the Brainnetome atlas[11], which was reverse-normalized to each participant's structural MRI scan. Standardized uptake value ratio (SUVR) images were obtained using whole cerebellum as a reference region. The voxel values assigned to a previously identified region-of-interest (ROI) were averaged to obtain a regional SUVR value. The global retention ratio for Florbetapir images was computed based on Aβ-related regions including the frontal, anterior/posterior cingulate, lateral parietal, and lateral temporal regions[10]. Subjects were classified as amyloid-positive when the global Florbetapir retention ratio exceeded 1.11, consistent with previous approaches[12] (http://adni.loni.usc.edu/).

In addition, we employed gaussian mixture modeling for each ROI to address off-target Flortaucipir binding[13-15]. Following previous approaches[16], we assumed that a distri-bution of pathological signal would be skewed while those of off-target and non-specific signals would remain normally distributed across the 227 subject population. All Flo-rtaucipir SUVR values of each ROI were fitted through a one-component and a two-component gaussian mixture model, of which the results were compared five times using Bayesian information criterion (BIC). Consistently lower BIC in a one-component model than a two-component model indicates SUVR values of the region are roughly normally distributed, implying no evidence of pathological tau deposition. The regions fitted better with a one-compo-nent model were considered as not or not yet involved in tauopathy, so not included in the study (33 brain regions were regarded as off-target regions for the ADNI dataset and 46 for the Korean validation dataset (see Table 3 below)).

TABLE 3

| List of off-target regions ("Sup": superior; "Mid": middle; "Lat": lateral). | | | | |
|---|---|---|---|---|
| A. *Gaussian* mixture modeling | | | | B. *Hippocampus* and subcortical areas ADNI & Korean |
| ADNI discovery dataset | | Korean validation dataset | | dataset |
| Left | Right | Left | Right | Left & Right |
| Precentral 3 | Precentral 4 | Orbital 2 | Sup.frontal 7 | Amygdala 1 |
| Precentral 4 | Basal ganglia 1 | Orbital 6 | Mid.frontal 7 | Amygdala 2 |
| Paracentral 2 | Basal ganglia 2 | Paracentral 2 | Orbital 1 | Hippocampus 1 |
| Postcentral 4 | Basal ganglia 4 | Postcentral 2 | Orbital 2 | Hippocampus 2 |
| Lat.occipital 3 | Basal ganglia 5 | Cingulate 7 | Orbital 4 | Basal ganglia 1 |
| Hippocampus 2 | Basal ganglia 6 | Amygdala 1 | Precentral 4 | Basal ganglia 2 |
| Basal ganglia 1 | Thalamus 1 | Amygdala 2 | Paracentral 1 | Basal ganglia 3 |
| Basal ganglia 2 | Thalamus 2 | Hippocampus 1 | Paracentral 2 | Basal ganglia 4 |
| Basal ganglia 4 | Thalamus 3 | Basal ganglia 1 | Cingulate 2 | Basal ganglia 5 |
| Basal ganglia 5 | Thalamus 4 | Basal ganglia 3 | Cingulate 3 | Basal ganglia 6 |
| Basal ganglia 6 | Thalamus 5 | Basal ganglia 5 | Cingulate 7 | Thalamus 1 |
| Thalamus 1 | Thalamus 6 | Basal ganglia 6 | Amygdala 1 | Thalamus 2 |
| Thalamus 2 | Thalamus 7 | Thalamus 1 | Amygdala 2 | Thalamus 3 |
| Thalamus 3 | Thalamus 8 | Thalamus 2 | Hippocampus 1 | Thalamus 4 |
| Thalamus 4 | | Thalamus 3 | Hippocampus 2 | Thalamus 5 |
| Thalamus 5 | | Thalamus 4 | Basal ganglia 1 | Thalamus 6 |
| Thalamus 6 | | Thalamus 5 | Basal ganglia 3 | Thalamus 7 |
| Thalamus 7 | | Thalamus 6 | Basal ganglia 5 | Thalamus 8 |
| Thalamus 8 | | Thalamus 7 | Basal ganglia 7 | |
| | | Thalamus 8 | Thalamus 1 | |
| | | | Thalamus 2 | |
| | | | Thalamus 3 | |
| | | | Thalamus 4 | |
| | | | Thalamus 5 | |
| | | | Thalamus 6 | |
| | | | Thalamus 7 | |

We then constructed a W-score map[17-19] for each Flortaucipir PET image to represent individual pathological tau burden compared to the amyloid-PET-negative CN group[20]. W-scores are standardized values adjusted for covariates including age, sex, and years of education. For each ROI, a linear regression was performed between the covariates and the regional SUVR values in the control group. The W-score was computed as a difference between actual and predicted pathological burden (i.e. the residual) of each subject, divided by the standard deviation of residuals in the control group. In the individual W-score maps generated for Flortaucipir PET scans, greater values indicate greater Flortaucipir uptake, suggesting greater tau pathological burden.

Structural Network Construction

Structural networks were constructed using diffusion tensor imaging (DTI) techniques, based on eddy-current-corrected diffusion-weighted MR images (FSL, http://www.fmrib.ox.ac.uk/fsl/). Each structural network consisted of nodes (brain regions) and edges (connections between node pairs). For each hemisphere, the nodes comprised the 105 cerebral cortical and 18 subcortical brain regions defined by the Brainnetome atlas[11]. T1-weighted MR image volumes from the Brainnetome atlas were resampled to corresponding eddy-current-corrected diffusion-weighted MR image volumes using FreeSurfer to specify the nodes of each structural network. We derived the structural connectivity matrix at both individual and group levels. An individual-level network edge was deemed present if there was at least one streamline between a node pair, acquired by whole-brain deterministic tractography using the second order Runge-Kutta algorithm through the Diffusion toolkit[21]. Fiber tracking was initiated at the 8 random points of each seed voxel with a fractional anisotropy (FA)>0.3 and ended at the voxels with FA<0.2 or a tract turning angle of >45 degrees.

The strength of each edge was determined based on the FA values averaged across all connecting streamlines using the UCLA Multimodal Connectivity Package (https://github.com/jbrown81/umcp)[22]. FA values have been considered to represent the level of microstructural organization of white matter tracts[23], which has been associated with the functional efficacy of the connections[24,25]. The group-level network was computed by averaging individual network edges present in more than a third of all healthy (Aβ-CN) subjects. In the group-level network, 4.68% of edges were connected, and their range of mean FA values was 0.2215 [0.1766, 0.2842] (median [Q1, Q3]).

Determination of Pseudo-Longitudinal Order

Figure 7:
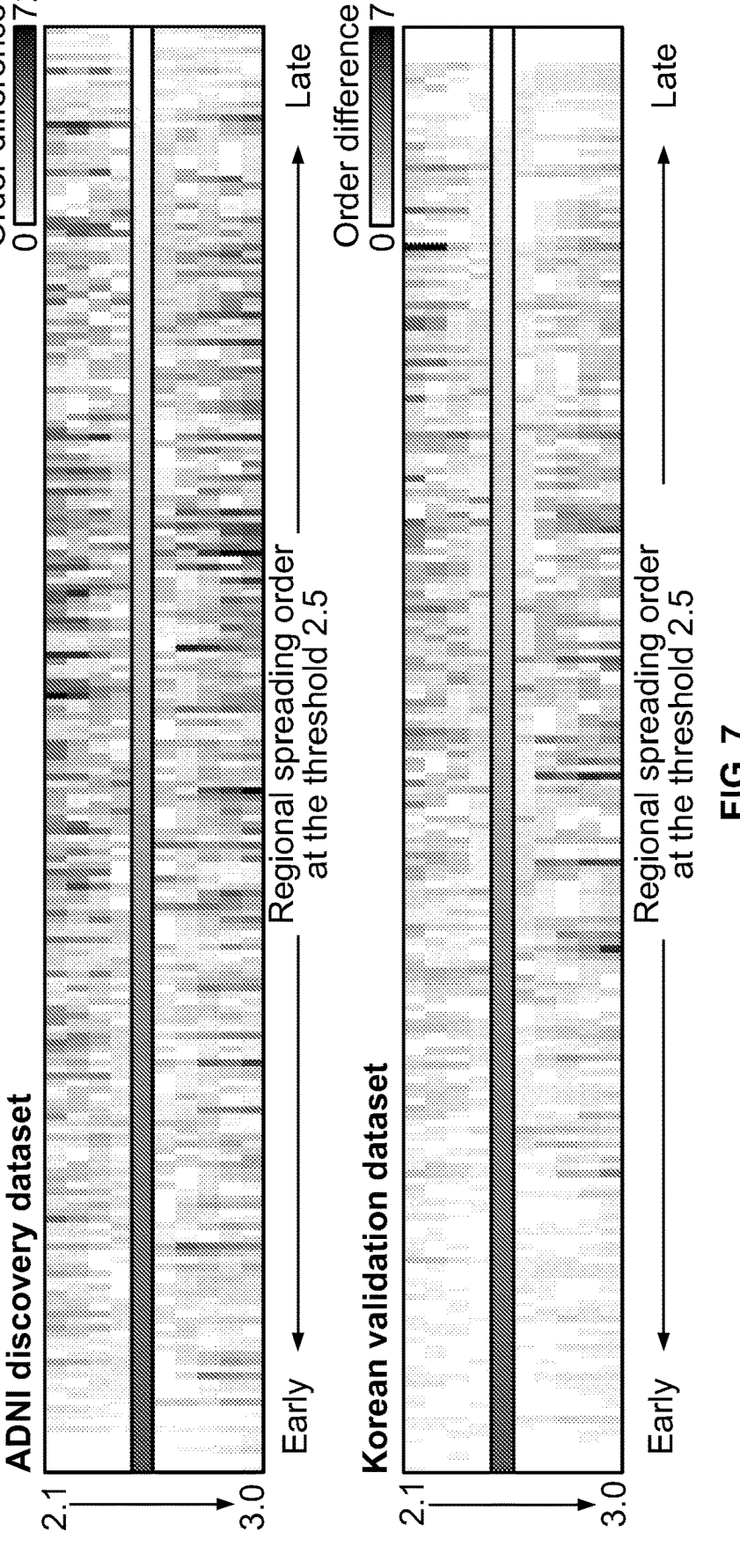
FIG. 7 depicts pseudo-longitudinal tau regional spreading order plotted against a range of tau W-score cutoffs. The regional spreading order was obtained using each W-score cutoff between 2.1 and 3.0 (inclusive) with an interval of 0.1. Regions of interests (ROIs) were aligned by their spreading order at our chosen threshold of 2.5, and differences in order were computed between this threshold and the others. A grayscale color bar in the center of each map represents the pseudo-order at tau W-score threshold of 2.5, with deeper hues representing earlier regions. The grayscale color bar indicates the absolute value of the change in order (if any) at the alternative threshold.

To study the non-linear acceleration of tau aggregation required the use of cross-sectional data to make longitudinal inferences. To this end, we first constructed a pseudo-longitudinal order by applying a frequency-based method to the tau-PET data of presymptomatic and prodromal AD (Aβ-positive CN and MCI, early or late) subjects. ROIs were ordered to define a regional tau spreading order by the frequencies with which the regional W-scores exceeded a given threshold across all subjects. We used a W-score threshold of 2.5, following previous research[26], but other thresholds were also considered to evaluate robustness (see FIG. 7). Subjects were sorted based on their number of ROIs having suprathreshold tau W-scores. To determine the period in which tau acceleration occurs, we used a smoothed line of the frequency graph based on the pseudo-longitudinal order. We deemed that the acceleration begins where the slope of the graph becomes larger than two and ends at the second inflection point, where the second derivative become zero.

Network Flow-Based Connectivity Derivation

We constructed a flow-based network based on maximum inter-nodal flow, using the whole-brain structural network to model the extent of tau propagation between each node pair. Every possible non-overlapping distinct path between any two nodes was extracted by employing a graph-theoretical maximum-flow calculation method using the binary normative brain network[27,28]. Each separate path contributed to the total inter-nodal flow by the amount of the mean FA value of all edges in the path divided by the average inter-nodal streamline length in mm. The partial contributions were then combined through all distinct paths, which became an edge weight between the source and sink nodes in the flow-based connectivity matrix. By adopting multiple distinct paths between two nodes, the flow-based network provides a method for predicting the physical amount of tau delivered from the source to sink node. This flow network was constructed at both the individual and group levels using the healthy structural connectome.

Propagation Hub Identification

The flow-based network described above was next used to identify propagation hubs, hypothesized to drive the acceleration phase of tau spreading. To this end, we searched a library of network flow-based connectivity maps, one seeded by each of the 246 brain regions-of-interest, and we estimated the goodness-of-fit (GOF) of each seed's map to the regions representing the tau acceleration phase. Specifically, binary inner and outer mask areas were defined within the tau acceleration phase regions across a range of thresholds (see FIG. 7). Having the same number of brain regions, the inner and outer masks were created to capture earlier and later tau spreading, and the inner mask was gradually expanded, producing 7 different sets of inner-outer mask pairs, to mimic tau propagation and to avoid potential influence of arbitrary thresholding. A GOF score was then calculated for each seed as the difference between the average flow-based connectivity, derived from healthy subjects, to regions falling within each inner-outer mask pairs, and a permutation-based one-sample t-test was performed using the GOF scores (see Example 6). The significance level was determined using p<0.05, Bonferroni-corrected for multiple tests. GOF scores and t-statistics were calculated for each seed region, across all 7 inner-outer mask pairs, and the propagation hubs were identified as the regions showing significant GOF scores for all 7 mask pairs.

Correlation Analysis Relating Healthy Network Flow-Based Connectivity to Tau Deposition Topography To assess the relationship between the network flow-based connectivity in health and the topographical pattern of tau deposition in prodromal AD, we performed correlation analyses between the group-level flow network derived from the identified ITG propagation hubs and the group-level tau-PET W-maps from ADNI subjects with early and late MCI. Correlations were evaluated in each hemisphere using the ipsilateral propagation hub. To place our findings in context of previous work from our group[29,30], we compared the network flow-based correlations to those derived using shortest path length and Euclidean distance from the propagation hubs. The matrix of shortest path length was computed using group-level FA-weighted structural connectivity, and the Euclidean distances between each pair of nodes were averaged through all healthy subjects. For the correlation analyses, statistical significance was set to p<0.05 and multiple comparisons were corrected using the Benjamini-Hochberg false discovery rate (FDR) method[31] across three different measures correlated with tau-PET topography and the two ITG propagation hubs. Furthermore, we calculated the distribution of z-transformed correlation coefficients using all brain regions as seeds to visualize how the ITG propagation hubs compared to other regions in terms of correlation with the topographical tau deposition pattern and to assess the statistical meaning of the correlation coefficient for the ITG propagation hubs compared to other regions in terms of correlation with the topographical tau deposition representing the acceleration>pre-acceleration phase pattern as defined above.

Analysis of Network-Based Aβ-Tau Interactions

We evaluated the relationship between Aβ and tau based on remote and local interactions. For computing remote interactions of each ROI, Aβ-PET SUVR values in each connected region, based on the structural connectome, were multiplied by the FA value of the connecting tract, inversely weighted by the streamline length, based on the notion that remote interactions will reflect the strength of the connection and the distance over which these effects must travel[32,33]. The connectivity-weighted Aβ-PET SUVRs for all connected regions were summed, and this remote Aβ influence value was then multiplied by the tau W-score of the ROI. In this way, a region's remote Aβ-tau interaction was determined by the strength and number of its connections to Aβ-PET-positive brain areas and by its local tau deposition. Similarly, local Aβ-tau interactions were obtained by multiplying the region's Aβ-PET SUVR by the region's local tau W-score. For the magnitude of Aβ deposition, the regional Aβ-PET SUVR value was used because of its narrow dynamic range; in this context, W-score normalization may skew or exaggerate small changes in Aβ deposition[34].

To estimate where the remote and local interactions take place earliest in AD progression, we applied the same frequency-based method used for constructing the pseudo-longitudinal tau spreading order. Brain regions were ordered using the frequencies with which their remote or local Aβ influence metric was positive and the tau W-score exceeded a given threshold. Both remote Aβ influence and local Aβ positivity were determined using regional cutoff values calculated by employing a previously reported method[35] that iteratively removes outliers within each region's data from the Aβ-negative CN group until no outlier arises and multiplies the maximum of remaining values by a small number as a buffer. We considered the values higher than 1.5× the interquartile range over the third quartile as outliers and identified a cutoff value as the 95th percentile value of the remaining data after removing outliers. In addition, we compared the interaction score of each region with the median interaction scores of all other regions. For this comparison, the continuous values of both interaction scores were used. Multiple comparisons were corrected using the FDR method[31] across all regions within each hemisphere. To verify robustness of the interaction pseudo-order, we also considered a range of tau thresholds (see FIG. 11).

Considering the proposed interactions between Aβ, tau, PrP[36,37], and Fyn[37,38], we examined the regional expression pattern of PRNP, the gene encoding PrP, and FYN, the gene encoding Fyn. To this end, we used the microarray gene expression dataset within the Allen Human Brain Atlas (AHBA)[39] following previous methods[40]. In the first step, we mapped probes on the microarray chip measuring the hybridization of cRNA in a tissue sample to corresponding genes using Re-annotator toolkit[41]. We then kept only probes exceeding the background in at least 50% of samples across six donors using intensity-based filtering[42,43]. Of the six donors, two had samples from both hemispheres and four had samples only from the left hemisphere. Probes that correlated weakly with RNA-seq data were then excluded among the probes measuring the same gene. Each tissue sample was assigned to the closest Brainnetome ROI based on the registration between the T1-weighted MR image of each donor and the ICBM152 T1 template in MNI space where the Brainnetome atlas[11] is defined. Finally, the expression values were standardized separately for each donor using scaled robust sigmoid normalization[44] after within-sample normalization across genes and averaged if more than one expression value existed for each ROI. We used mean expression levels of PRNP and FYN over all six donors in AHBA. To investigate the multi-level interaction scores, we calculated, for each brain region, the joint Aβ-PRNP expression level within its connected areas, weighted by the strength of those connections, and multiplied that Aβ-PRNP influence metric by the ROI's local tau W-score and FYN expression level (denoted Aβ-PRNP→tau-FYN). We also calculated local 4-molecule interaction scores in which the local Aβ-tau interaction score was multiplied by PRNP and FYN expression levels for each region. We then compared the lateral EC and ITG propagation hubs to the median scores of all other brain regions in terms of (remote) Aβ-PRNP→tau-FYN and (local) Aβ-PRNP-tau-FYN scores (See Example 6).

Longitudinal Analyses of Tau Acceleration

Figures 15A, 15B:
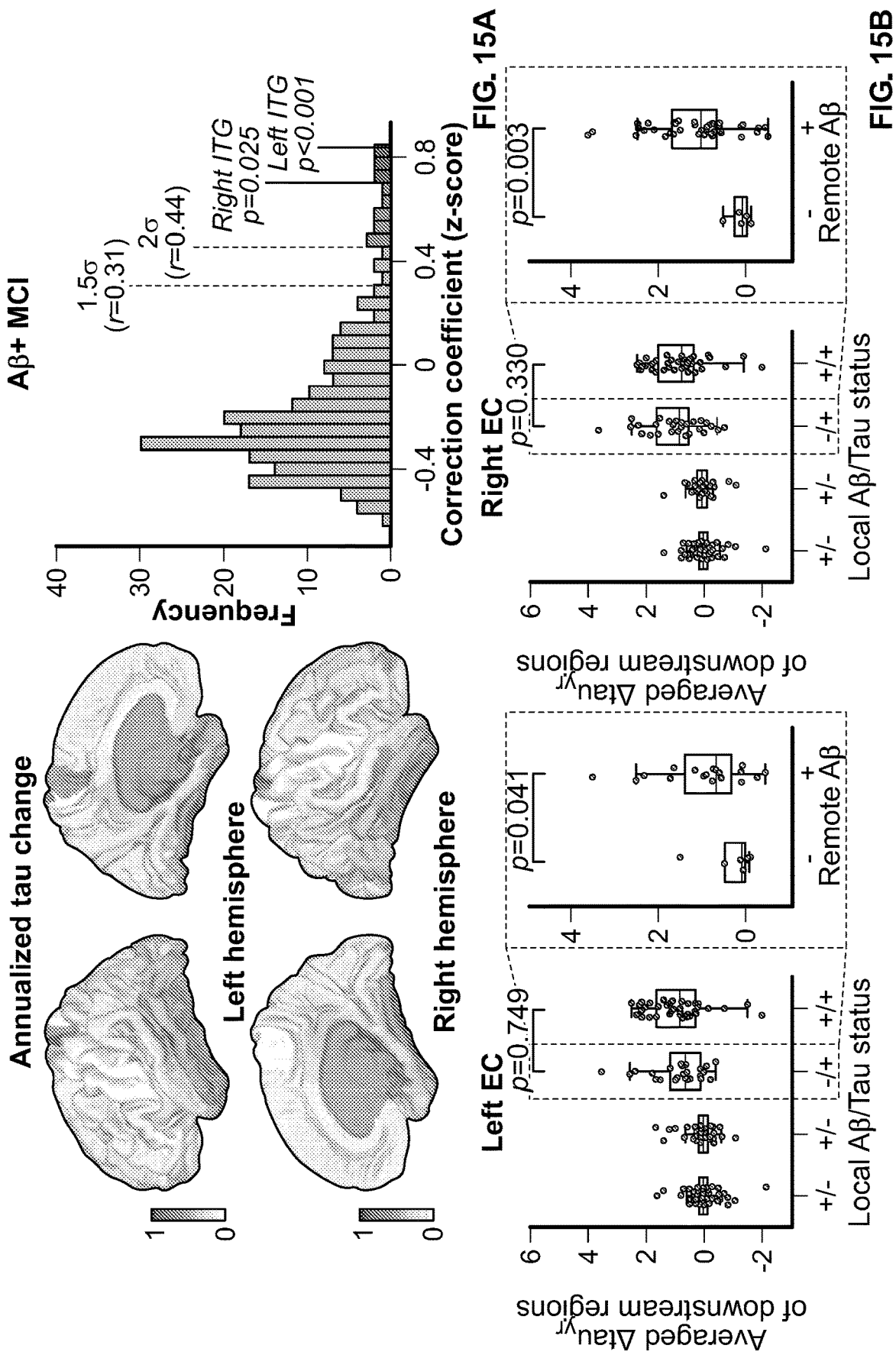
FIG. 15A-15C depicts results showing longitudinal sup-
port for the network-based Aβ-tau interaction model.
Figure 15C:
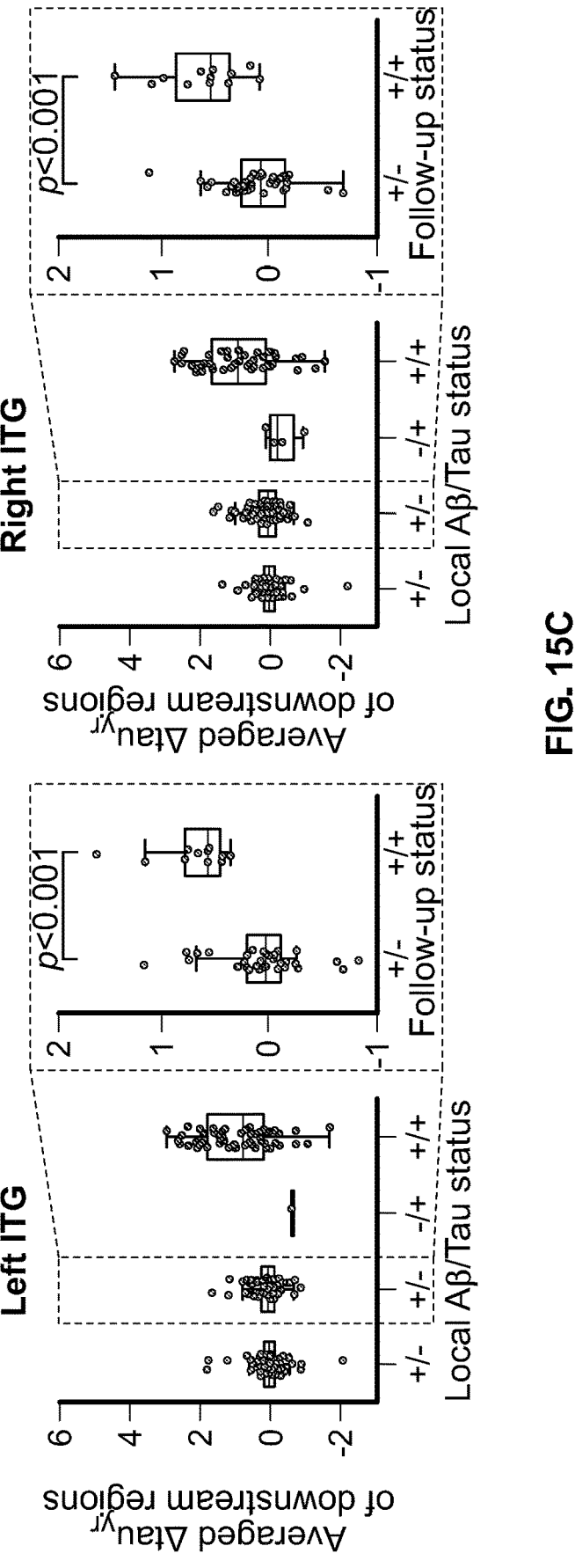

To strengthen the statistical power of the longitudinal analyses, we used regional tau W-scores of the ADNI and Korean datasets together. First, to determine whether the connectivity of the ITG stands out as a predictor of longitudinal tau accumulation, we performed correlation analyses "downstream" to the region-of-interest, by averaging the annualized change rates across tau W-scores among the 30 regions immediately following the region-of-interest within the dataset-specific regional tau spreading order. We first performed two-sample t-tests using the averaged annualized change rates to compare the effects of the EC being Aβ-positive vs. Aβ-negative in the presence of local tau-positivity. For the EC, subjects with negative local Aβ and positive tau were further divided into two subgroups according to the EC remote Aβ-tau interaction status: remote Aβ-negative/local tau-positive and remote Aβ-positive/local tau-positive (see FIG. 15B). The downstream tau accumulation rates of the two subgroups were compared to examine the effects of remote Aβ on tau within the EC, using a Mann-Whitney U test, appropriate here due to the nonparametric distribution of the tau accumulation rate in these subgroups. We next evaluated the effects of local interaction between Aβ and tau within the ITG (FIG. 15C). Subjects lacking local tau while having positive Aβ within the ITG were further divided into two sub-groups based on whether tau positivity emerged in the ITG at follow-up. The rationale for this subgrouping was that it would allow us to determine whether arrival of tau at the (already A-positive) ITG promoted greater downstream tau spreading. We then compared these subgroups using a Mann-Whitney U test. The number of downstream regions assessed in these analyses was first set to 30, but we also addressed effects over a range of this parameter from 20 to 50 (see Table 4 below).

TABLE 4

Test results of the prediction of downstream tau spreading based on Aβ–tau interaction model using alternative numbers of downstream regions ("EC": entorhinal cortex; "ITG": inferior temporal gyrus; "L": left; "R": right).

| Number of downstream regions | EC-based predictions (local Aβ+/tau+ vs. local Aβ−/tau+) | EC-based predictions (remote Aβ/local Aβ−/ tau+ vs. remote Aβ−/local Aβ−/ tau+) | ITG-based predictions (local Aβ/tau− □ tau+ vs. local Aβ/tau− □ tau− ) |
|---|---|---|---|
| 20 | t: 0.27, p: 0.786 (L)/ t: −0.90, p: 0.369 (R) | Z: 1.67, p: 0.047 (L)/ Z: 2.67, p: 0.004 (R) | Z: 4.28, p: <0.001 (L)/ Z: 4.16, p: <0.001 (R) |
| 30 (main results) | t: 0.32, p: 0.749 (L)/ t: −0.98, p: 0.330 (R) | Z: 1.73, p: 0.041 (L)/ Z: 2.73, p: 0.003 (R) | Z: 4.23, p: <0.001 (L)/ Z: 4.04, p: <0.001 (R) |
| 40 | t: 0.38, p: 0.708 (L)/ t: −0.90, p: 0.369 (R) | Z: 1.73, p: 0.041 (L)/ Z: 2.78, p: 0.003 (R) | Z: 4.17, p: <0.001 (L)/ Z: 3.75, p: <0.001 (R) |
| 50 | t: 0.53, p: 0.597 (L)/ t: −0.80, p: 0.429 (R) | Z: 1.73, p: 0.041 (L)/ Z: 2.84, p: 0.002 (R) | Z: 3.92, p: <0.001 (L)/ Z: 3.38, p: <0.001 (R) | between the regional flow-based networks, derived from healthy controls, and the group-level annualized change in tau-PET W-maps, derived from Aβ+ subjects with MCI (n=68). Off-target regions co-occurring in both datasets were removed from the correlation analyses but retained in network flow-based map construction, in keeping with the cross-sectional analyses. The correlation coefficients of all seed regions were transformed to z-scores, and the values of the ITG propagation hubs were presented on the distribution (see FIG. 15A).

Next, to assess the relationship between the two key Aβ-tau interactions and longitudinal tau accumulation, subjects were stratified by the status of local Aβ and tau for each ROI separately (including both left and right EC and ITG) as follows: (1) both Aβ and tau were negative (−/−), (2) Aβ was positive while tau was negative (+/−), (3) Aβ was negative while tau was positive (−/+), and (4) both were positive (+/+). Necessarily, for each region-of-interest, groups 1-4 had different subject compositions. For each subject, we determined the tau accumulation rate in regions Network-Based Therapeutic Window Construction To evaluate the implications of our model in terms of subject stratification for AD treatments, we derived quantitative thresholds illustrated in FIG. 5A-5B that correspond to: (1) remote Aβ-tau interaction within the lateral EC and (2) local Aβ-tau interaction within the ITG. The first threshold was computed by multiplying the regional cutoff of the EC remote Aβ influence metric by the tau W-score cutoff (2.5 in our study). Similarly, for the second threshold, the regional cutoff for the ITG local amyloid SUVR was multiplied by the tau W-score cutoff. For the purposes of an Aβ-lowering therapy, we added a 20% margin to both thresholds by lowering the first and raising the second, seeking to include subjects within the local border area. Using this approach, we classified each subject into one of three therapeutic groups: low risk (therapeutic group 1), suitable for Aβ-lowering therapy (therapeutic group 2), and low benefit (therapeutic group 3). We postulated that subjects who have enough EC remote Aβ-tau interaction but insufficient ITG Aβ-tau local interaction are most suitable for Aβ-lowering therapy (therapeutic group 2). Values for each metric were calculated in each hemisphere separately. Subjects were stratified to the low risk group (therapeutic group 1) if they had subthreshold values in both hemispheres for Threshold 1, whereas they were stratified to the low benefit group (therapeutic group 3) if both hemispheres had suprathreshold values for Threshold 2. If one hemisphere would yield assignment to therapeutic group 1 and the other to therapeutic group 3, then the subject was assigned to the low risk group, based on the notion that they might, upon re-testing, move into therapeutic group 2.

Using the above-referenced modeling and algorithm patients can be classified as being responders or non-responders to amyloid modulating treatment, tau-modulating treatment, both of such treatments or neither of treatments. As an alternative to the final step of characterization of patients based upon their responsiveness to treatment, however, the resulting data were also used to characterize patients according to changing levels of tau expression in the brain according to whether there was no tau, latent amounts of tau, spreading amounts of tau or propagating amounts of tau. This final step of characterization involved classifying patients according to their imaging results as well as final $W_{tau}$ calculation as in described below methods. This particular method is useful to determine, among other things, clinical outcome of a patient based upon severity of disease. In some embodiments, the classification of accerelated tau deposition identified below as spreading or propagating tau can be used to determine increasing severity of disease and increasing clinical progression of AD. Method follows:

Subject Stratification Based on Network-Based Aβ-Tau Interaction Model

Our findings suggested two important transitions during the natural history of AD, based on: (1) remote Aβ-tau interaction within the lateral EC and (2) local Aβ-tau interaction within the ITG. To examine subjects' status with respect to these transitions, we computed quantitative thresholds for each metric. The first threshold was computed by multiplying the regional cutoff of the EC remote Aβ influence metric by the tau W-score cutoff (2.5 in our study). Similarly, for the second threshold, the regional cutoff for the ITG local amyloid SUVR was multiplied by the tau W-score cutoff. Using this approach, we classified each subject into one of four groups: (1) least affected by the tau pathology ("tau-negative") in EC (44), (2) subthreshold EC remote Aβ-tau interaction despite the presence of EC tau ("latent tau" group), (3) suprathreshold EC remote Aβ-tau interaction but subthreshold ITG Aβ-tau local interaction ("spreading tau" group), and (4) suprathreshold ITG Aβ-tau local interaction ("propagating tau" group). Values for each metric were calculated in each hemisphere separately. Subjects were assigned to the latent tau group if they had subthreshold values in both hemispheres for Threshold 1, whereas they were stratified to the propagating tau group if they had suprathreshold values in both hemispheres for Threshold 2. If one hemisphere would yield assignment to the latent tau and the other to propagating tau group, then the subject was assigned to the latent tau group, based on the notion that they might, upon re-testing, move into the spreading tau group as defined.

Figure 8:
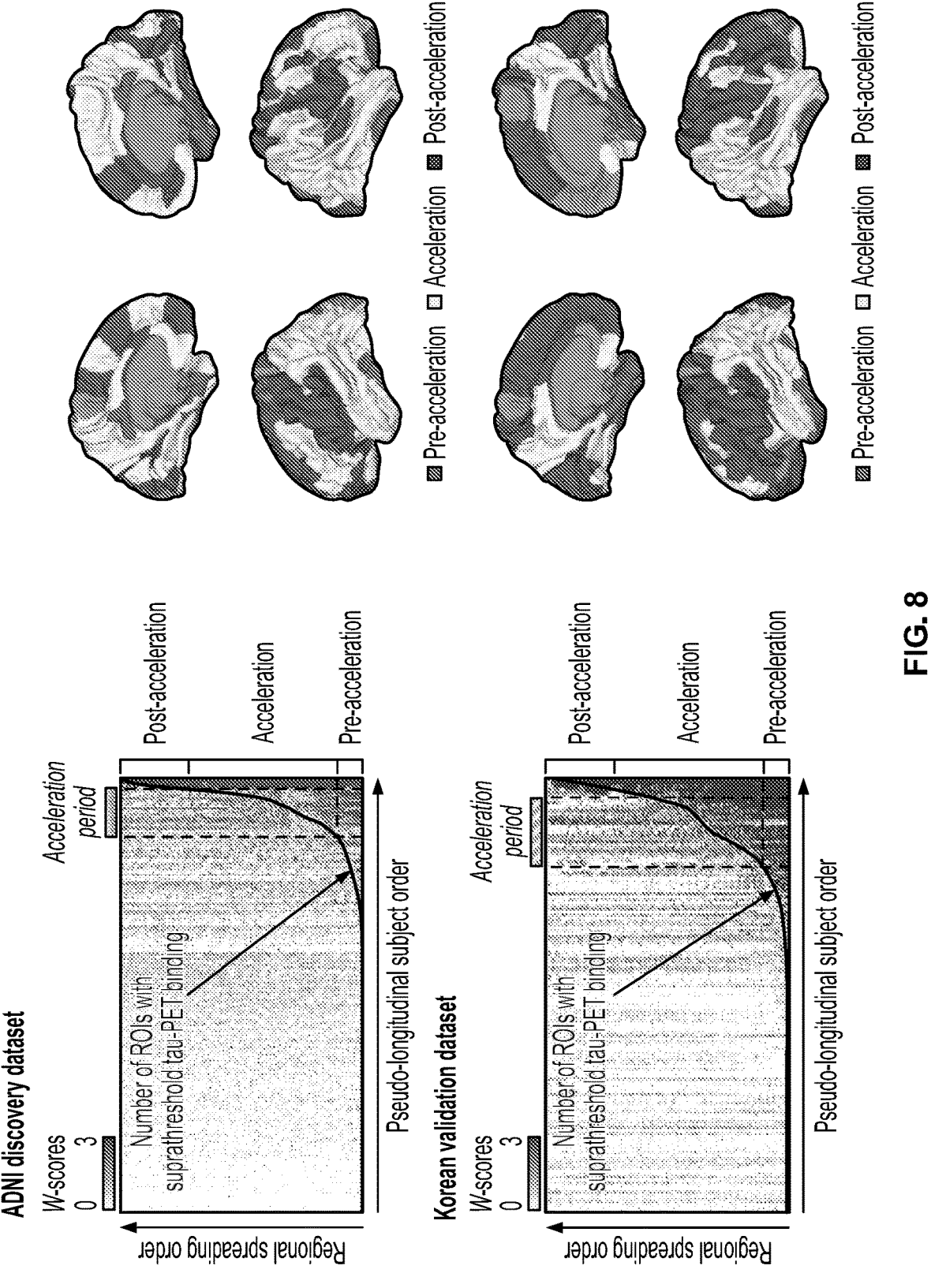
FIG. 8 depicts replication of tau regional spreading order and acceleration phase topography in the Korean validation dataset. ADNI data (top) are re-presented from FIG. 1C for comparison to the findings, obtained using an identical procedure, from the Korean validation dataset (bottom). The tau regional spreading order showed high correspondence (Spearman ρ=0.70, and there was strong overall topographical agreement between datasets in the regions representing the three inferred phases.

Example 2. Non-Linear Acceleration of Network-Based Tau Spreading Occurs in Early MCI Recent in vivo evidence supports the view that tau pathophysiology exhibits a non-linear acceleration during the natural history of AD (FIG. 1A)[2,45]. To capture this phenomenon, we studied individuals enrolled in a multicenter observational study, the AD Neuroimaging Initiative (ADNI), who underwent cross-sectional $^{18}$F-florbetapir-PET (henceforth "amyloid-PET") and $^{18}$F-flortaucipir-PET (henceforth "tau-PET") imaging (see Table 1). First, we mapped regions of tau-PET positivity in presymptomatic (Aβ+, cognitively normal, CN, n=67) and prodromal AD (Aβ+, early (n=28) and late (n=17) mild cognitive impairment, MCI, see Example 1). Tau-PET positivity in presymptomatic AD was mild, but the entorhinal cortex (EC; [A28/34, A35/36r]) stood out as a region with high mean tau-PET signal (FIG. 1B). This tau-PET mapping approach also revealed the expected sharp increase in brain-wide tau deposition in late prodromal AD. Second, we calculated the number of tau-positive brain regions for each subject within these groups (see Example 1). Based on the resulting frequency distribution for regional tau burden, we constructed a pseudo-longitudinal disease severity order, with the least severe subjects being those with the fewest tau-PET-positive regions. This approach identified the EC (A28/341, A35/36r) as the earliest region to become tau-positive, based on the frequency distribution. Overall, these approaches converged to broadly reproduce the canonical stages of tau neurofibrillary tangle formation inferred from neuropathological studies[3] (see Table 5 below). Most importantly, this dataset enabled us to identify an inferred "acceleration phase" of exponential spreading in the spatial extent of tau-PET positivity and, in turn, the regions that exhibit tau-PET positivity before, during, and after the tau acceleration phase (FIG. 1C). The tau regional spreading order was generally robust across a range of tau W-score thresholds (FIG. 7), and the key findings shown in FIG. 1 were replicated in an independent sample of older subjects from across the AD clinical spectrum (henceforth, "Korean validation dataset", see Example 1, FIG. 7 and FIG. 8). Importantly, the Korean validation dataset included a larger proportion of subjects with more advanced clinical AD (see Table 1), suggesting that the identified acceleration phase did not result simply from analyzing an ADNI sample skewed toward early stages of AD.

TABLE 5

Pseudo-longitudinal tau spreading order ("ROI": region of interest; "L": left; "R": right; "SFG": superior frontal gyrus; "MFG": middle frontal gyrus; "IFG": inferior frontal gyrus; "OrG": orbital gyrus; "PrG": precentral gyrus; "PCL": paracentral lobule; "STG": superior temporal gyrus; "MTG": middle temporal gyrus; "ITG": inferior temporal gyrus; "FuG": fusiform gyrus; "PhG": parahippocampal gyrus; "Psts": posterior superior temporal sulcus; "SPL": superior parietal lobule; "IPL": inferior parietal lobule; "Pcun": precuneus; "PoG": postcentral gyrus; "INS": insular gyrus; "CG": cingulate gyrus; "MVOcC": medioventral occipital cortex; "LOcC": lateral occipital cortex; "Amyg": amygdala; "Hipp": hippocampus; "BG": basal ganglia). ROIs are displayed with hemisphere, initial seed mask area where the parcel was derived (naming convention applied in the main text), and the parcel name from the Brainnetome atlas (in brackets). Data are presented as the percentage of subjects showing a W-score > 2.5 (%) with the median W-score in parentheses. Regions representing the pre-acceleration period are #1 to #23; regions representing the acceleration period are #24 to #146; and regions representing the post-amplification period are #147 to #213. Regions in bold font (#7 and #22) are the two leading propagation hubs.

| # | | ROI | % (W) |
|---|---|---|---|
| 1 | L | PhG 4 [A28/34] | 13.7 (0.3) |
| 2 | L | PhG 5 [TI] | 13.7 (0.1) |
| 3 | L | Amyg 1 [mAmyg] | 13.2 (0.3) |
| 4 | R | PhG 1 [A35/36r] | 12.3 (0.3) |
| 5 | L | PhG 1 [A35/36r] | 12.3 (0.2) |

TABLE 5-continued

Pseudo-longitudinal tau spreading order ("ROI": region of interest; "L": left; "R": right; "SFG": superior frontal gyrus; "MFG": middle frontal gyrus; "IFG": inferior frontal gyrus; "OrG": orbital gyrus; "PrG": precentral gyrus; "PCL": paracentral lobule; "STG": superior temporal gyrus; "MTG": middle temporal gyrus; "ITG": inferior temporal gyrus; "FuG": fusiform gyrus; "PhG": parahippocampal gyrus; "Psts": posterior superior temporal sulcus; "SPL": superior parietal lobule; "IPL": inferior parietal lobule; "Pcun": precuneus; "PoG": postcentral gyrus; "INS": insular gyrus; "CG": cingulate gyrus; "MVOcC": medioventral occipital cortex; "LOcC": lateral occipital cortex; "Amyg": amygdala; "Hipp": hippocampus; "BG": basal ganglia). ROIs are displayed with hemisphere, initial seed mask area where the parcel was derived (naming convention applied in the main text), and the parcel name from the Brainnetome atlas (in brackets). Data are presented as the percentage of subjects showing a W-score > 2.5 (%) with the median W-score in parentheses. Regions representing the pre-acceleration period are #1 to #23; regions representing the acceleration period are #24 to #146; and regions representing the post-amplification period are #147 to #213. Regions in bold font (#7 and #22) are the two leading propagation hubs.

| # | | ROI | % (W) |
|---|---|---|---|
| 6 | R | PhG 5 [TI] | 12.3 (0.1) |
| 7 | R | *ITG 4 [A20il]* | 11.0 (0.2) |
| 8 | R | PhG 3 [TL] | 11.0 (0.2) |
| 9 | R | FuG 1 [A20rv] | 10.6 (0.3) |
| 10 | R | PhG 4 [A28/34] | 10.6 (0.2) |
| 11 | R | PhG 2 [A35/36c] | 10.1 (0.4) |
| 12 | R | ITG 7 [A20cv] | 10.1 (0.2) |
| 13 | R | Amyg 1 [mAmyg] | 10.1 (0.2) |
| 14 | L | Hipp 1 [rHipp] | 9.7 (0.3) |
| 15 | R | LOcC 6 [lsOccG] | 9.7 (0.2) |
| 16 | R | FuG 2 [A37mv] | 9.7 (0.2) |
| 17 | R | STG 1 [A38m] | 9.7 (0.1) |
| 18 | L | CG 1 [A23d] | 9.3 (0.3) |
| 19 | R | CG 1 [A23d] | 9.3 (0.3) |
| 20 | L | PhG 3 [TL] | 9.3 (0.2) |
| 21 | L | ITG 6 [A20cl] | 9.3 (0.2) |
| 22 | L | *ITG 7 [A20cv]* | 9.3 (0.2) |
| 23 | R | ITG 1 [A20iv] | 9.3 (0.2) |
| 24 | R | ITG 2 [A37elv] | 9.3 (0.2) |
| 25 | R | FuG 3 [A37lv] | 9.3 (0.1) |
| 26 | R | IPL 3 [A40rd] | 8.8 (0.2) |
| 27 | L | FuG 1 [A20rv] | 8.8 (0.2) |
| 28 | R | ITG 6 [A20cl] | 8.8 (0.2) |
| 29 | R | ITG 3 [A20r] | 8.8 (0.2) |
| 30 | L | MTG 4 [aSTS] | 8.8 (0.2) |
| 31 | L | PhG 2 [A35/36c] | 8.8 (0.2) |
| 32 | R | MTG 2 [A21r] | 8.8 (0.2) |
| 33 | R | MTG 4 [aSTS] | 8.8 (0.2) |
| 34 | R | Psts 1 [rpSTS] | 8.8 (0.2) |
| 35 | L | LOcC 6 [lsOccG] | 8.8 (0.2) |
| 36 | R | PhG 6 [TH] | 8.8 (0.2) |
| 37 | R | STG 5 [A38l] | 8.8 (0.2) |
| 38 | L | IPL 5 [A39rv] | 8.8 (0.1) |
| 39 | R | Pcun 4 [A31] | 8.4 (0.2) |
| 40 | R | Hipp 1 [rHipp] | 8.4 (0.2) |
| 41 | L | IPL 2 [A39rd] | 8.4 (0.2) |
| 42 | R | CG 6 [A23c] | 8.4 (0.2) |
| 43 | L | Psts 1 [rpSTS] | 8.4 (0.2) |
| 44 | L | ITG 2 [A37elv] | 8.4 (0.1) |
| 45 | L | Psts 2 [cpSTS] | 8.4 (0.1) |
| 46 | L | FuG 3 [A37lv] | 8.4 (0.1) |
| 47 | R | ITG 5 [A37vl] | 8.4 (0.1) |
| 48 | L | ITG 4 [A20il] | 7.9 (0.3) |
| 49 | L | FuG 2 [A37mv] | 7.9 (0.2) |
| 50 | L | ITG 1 [A20iv] | 7.9 (0.1) |
| 51 | R | IPL 2 [A39rd] | 7.9 (0.1) |
| 52 | R | STG 6 [A22r] | 7.5 (0.3) |
| 53 | L | MTG 2 [A21r] | 7.5 (0.3) |
| 54 | L | SPL 3 [A5l] | 7.5 (0.3) |
| 55 | L | STG 6 [A22r] | 7.5 (0.3) |
| 56 | L | MTG 1 [A21c] | 7.5 (0.2) |
| 57 | L | Pcun 4 [A31] | 7.5 (0.2) |
| 58 | R | Amyg 2 [lAmyg] | 7.5 (0.2) |
| 59 | R | Pcun 1 [A7m] | 7.5 (0.2) |
| 60 | R | Pcun 2 [A5m] | 7.5 (0.2) |
| 61 | R | OrG 6 [A12/47l] | 7.5 (0.2) |
| 62 | L | Pcun 2 [A5m] | 7.5 (0.1) |
| 63 | R | LOcC 1 [mOccG] | 7.5 (0.1) |
| 64 | L | STG 4 [A22c] | 7.5 (0.1) |
| 65 | L | ITG 3 [A20r] | 7.5 (0.1) |
| 66 | R | IPL 5 [A39rv] | 7.5 (0.1) |
| 67 | L | Amyg 2 [lAmyg] | 7.0 (0.2) |
| 68 | R | MTG 1 [A21c] | 7.0 (0.2) |
| 69 | R | LOcC 2 [V5/MT+] | 7.0 (0.2) |
| 70 | L | STG 1 [A38m] | 7.0 (0.2) |
| 71 | R | MVOcC 4 [rLinG] | 7.0 (0.1) |
| 72 | L | MFG 4 [A9/46v] | 7.0 (0.1) |
| 73 | R | SPL 5 [A7ip] | 7.0 (0.1) |
| 74 | L | PhG 6 [TH] | 7.0 (0.1) |
| 75 | L | IPL 1 [A39c] | 7.0 (0.0) |
| 76 | R | CG 4 [A23v] | 6.6 (0.2) |
| 77 | R | IPL 4 [A40c] | 6.6 (0.2) |
| 78 | L | MTG 3 [A37dl] | 6.6 (0.2) |
| 79 | L | Pcun 3 [dmPOS] | 6.6 (0.2) |
| 80 | R | Psts 2 [cpSTS] | 6.6 (0.2) |
| 81 | L | IPL 4 [A40c] | 6.6 (0.1) |
| 82 | L | CG 5 [A24cd] | 6.6 (0.1) |
| 83 | R | MFG 4 [A9/46v] | 6.6 (0.1) |
| 84 | L | IPL 3 [A40rd] | 6.6 (0.1) |
| 85 | R | SPL 3 [A5l] | 6.6 (0.1) |
| 86 | L | SPL 5 [A7ip] | 6.6 (0) |
| 87 | R | IPL 1 [A39c] | 6.6 (0.0) |
| 88 | L | Pcun 1 [A7m] | 6.2 (0.2) |
| 89 | R | Pcun 3 [dmPOS] | 6.2 (0.2) |
| 90 | L | CG 4 [A23v] | 6.2 (0.2) |
| 91 | R | PCL 1 [A1/2/3ll] | 6.2 (0.2) |
| 92 | R | MFG 6 [A6vl] | 6.2 (0.2) |
| 93 | R | OrG 4 [A11m] | 6.2 (0.2) |
| 94 | R | Hipp 2 [cHipp] | 6.2 (0.2) |
| 95 | L | OrG 3 [A11l] | 6.2 (0.1) |
| 96 | L | LOcC 2 [V5/MT+] | 6.2 (0.1) |
| 97 | R | IFG 2 [IFS] | 6.2 (0.1) |
| 98 | R | MFG 7 [A10l] | 6.2 (0.1) |
| 99 | L | MFG 6 [A6vl] | 6.2 (0.1) |
| 100 | L | ITG 5 [A37vl] | 6.2 (0.1) |
| 101 | L | IFG 4 [A45r] | 6.2 (0.1) |
| 102 | L | MVOcC 4 [rLinG] | 6.2 (0.1) |
| 103 | L | LOcC 1 [mOccG] | 6.2 (0.0) |
| 104 | L | BG 3 [NAC] | 5.7 (0.2) |
| 105 | L | MFG 2 [IFJ] | 5.7 (0.2) |
| 106 | R | SPL 2 [A7c] | 5.7 (0.2) |
| 107 | R | OrG 5 [A13] | 5.7 (0.2) |
| 108 | L | MFG 3 [A46] | 5.7 (0.2) |
| 109 | R | SFG 1 [A8m] | 5.7 (0.2) |
| 110 | L | SPL 2 [A7c] | 5.7 (0.1) |
| 111 | R | OrG 2 [A12/47o] | 5.7 (0.1) |
| 112 | R | SFG 2 [A8dl] | 5.7 (0.1) |
| 113 | R | SPL 1 [A7r] | 5.7 (0.1) |
| 114 | R | MTG 3 [A37dl] | 5.7 (0.1) |
| 115 | L | LOCC 4 [iOccG] | 5.7 (0.1) |
| 116 | R | LOcC 4 [iOccG] | 5.7 (0.0) |
| 117 | R | INS 2 [vIa] | 5.3 (0.2) |
| 118 | R | PrG 2 [A6cdl] | 5.3 (0.2) |
| 119 | L | OrG 5 [A13] | 5.3 (0.2) |
| 120 | R | MFG 2 [IFJ] | 5.3 (0.2) |
| 121 | L | SFG 1 [A8m] | 5.3 (0.2) |

TABLE 5-continued

Pseudo-longitudinal tau spreading order ("ROI": region of interest;
"L": left; "R": right; "SFG": superior frontal gyrus; "MFG": middle
frontal gyrus; "IFG": inferior frontal gyrus; "OrG": orbital gyrus; "PrG":
precentral gyrus; "PCL": paracentral lobule; "STG": superior temporal
gyrus; "MTG": middle temporal gyrus; "ITG": inferior temporal gyrus;
"FuG": fusiform gyrus; "PhG": parahippocampal gyrus; "Psts": posterior
superior temporal sulcus; "SPL": superior parietal lobule; "IPL": inferior
parietal lobule; "Pcun": precuneus; "PoG": postcentral gyrus; "INS":
insular gyrus; "CG": cingulate gyrus; "MVOcC": medioventral occipital
cortex; "LOcC": lateral occipital cortex; "Amyg": amygdala; "Hipp":
hippocampus; "BG": basal ganglia). ROIs are displayed with hemisphere,
initial seed mask area where the parcel was derived (naming convention
applied in the main text), and the parcel name from the Brainnetome
atlas (in brackets). Data are presented as the percentage of subjects
showing a W-score > 2.5 (%) with the median W-score in parentheses.
Regions representing the pre-acceleration period are #1 to #23; regions
representing the acceleration period are #24 to #146; and regions
representing the post-amplification period are #147 to #213. Regions
in bold font (#7 and #22) are the two leading propagation hubs.

| # | | ROI | % (W) |
|---|---|---|---|
| 122 | L | INS 2 [vIa] | 5.3 (0.2) |
| 123 | R | PrG 6 [A6cvl] | 5.3 (0.2) |
| 124 | R | MFG 3 [A46] | 5.3 (0.2) |
| 125 | L | SFG 7 [A10m] | 5.3 (0.2) |
| 126 | R | SFG 7 [A10m] | 5.3 (0.2) |
| 127 | L | CG 6 [A23c] | 5.3 (0.2) |
| 128 | R | IFG 4 [A45r] | 5.3 (0.1) |
| 129 | R | MFG 1 [A9/46d] | 5.3 (0.1) |
| 130 | R | IPL 6 [A40rv] | 5.3 (0.1) |
| 131 | R | CG 5 [A24cd] | 5.3 (0.1) |
| 132 | L | IFG 2 [IFS] | 5.3 (0.1) |
| 133 | R | INS 3 [dIa] | 5.3 (0.1) |
| 134 | R | MVOcC 3 [cCunG] | 5.3 (0.1) |
| 135 | L | SPL 1 [A7r] | 5.3 (0.1) |
| 136 | L | MVOcC 2 [rCunG] | 5.3 (0.1) |
| 137 | R | PoG 3 [A2] | 5.3 (0.1) |
| 138 | R | PCL 2 [A4ll] | 5.3 (0.0) |
| 139 | R | SFG 5 [A6m] | 5.3 (0.0) |
| 140 | L | PCL 1 [A1/2/3ll] | 5.3 (0.0) |
| 141 | L | STG 5 [A38l] | 4.8 (0.2) |
| 142 | L | INS 4 [vId/vIg] | 4.8 (0.2) |
| 143 | L | MFG 5 [A8vl] | 4.8 (0.2) |
| 144 | R | STG 3 [TE1.0/TE1.2] | 4.8 (0.2) |
| 145 | L | CG 7 [A32sg] | 4.8 (0.2) |
| 146 | L | STG 2 [A41/42] | 4.8 (0.2) |
| 147 | R | OrG 3 [A11l] | 4.8 (0.1) |
| 148 | L | SFG 6 [A9m] | 4.8 (0.1) |
| 149 | R | MFG 5 [A8vl] | 4.8 (0.1) |
| 150 | L | MVOcC 1 [cLinG] | 4.8 (0.1) |
| 151 | L | CG 3 [A32p] | 4.8 (0.1) |
| 152 | L | PoG 3 [A2] | 4.8 (0.1) |
| 153 | L | MFG 1 [A9/46d] | 4.8 (0.1) |
| 154 | R | STG 2 [A41/42] | 4.8 (0.0) |
| 155 | R | SPL 4 [A7pc] | 4.8 (0.0) |
| 156 | L | IFG 3 [A45c] | 4.4 (0.2) |
| 157 | L | IPL 6 [A40rv] | 4.4 (0.2) |
| 158 | L | SFG 4 [A6dl] | 4.4 (0.2) |
| 159 | R | MVOcC 5 [vmPOS] | 4.4 (0.2) |
| 160 | R | IFG 1 [A44d] | 4.4 (0.2) |
| 161 | R | OrG 1 [A14m] | 4.4 (0.1) |
| 162 | R | SFG 3 [A9l] | 4.4 (0.1) |
| 163 | R | LOcC 5 [msOccG] | 4.4 (0.1) |
| 164 | L | OrG 2 [A12/47o] | 4.4 (0.1) |
| 165 | L | SFG 5 [A6m] | 4.4 (0.1) |
| 166 | R | INS 6 [dId] | 4.4 (0.1) |
| 167 | R | CG 7 [A32sg] | 4.4 (0.1) |
| 168 | L | MFG 7 [A10l] | 4.4 (0.0) |
| 169 | R | STG 4 [A22c] | 4.4 (0.0) |
| 170 | R | IFG 6 [A44v] | 4.0 (0.3) |
| 171 | R | SFG 4 [A6dl] | 4.0 (0.2) |
| 172 | L | SFG 2 [A8dl] | 4.0 (0.2) |
| 173 | L | OrG 1 [A14m] | 4.0 (0.2) |
| 174 | R | CG 3 [A32p] | 4.0 (0.2) |
| 175 | L | OrG 4 [A11m] | 4.0 (0.1) |
| 176 | R | SFG 6 [A9m] | 4.0 (0.1) |
| 177 | L | LOcC 5 [msOccG] | 4.0 (0.1) |
| 178 | R | BG 3 [NAC] | 4.0 (0.1) |
| 179 | R | IFG 3 [A45c] | 4.0 (0.1) |

TABLE 5-continued

Pseudo-longitudinal tau spreading order ("ROI": region of interest;
"L": left; "R": right; "SFG": superior frontal gyrus; "MFG": middle
frontal gyrus; "IFG": inferior frontal gyrus; "OrG": orbital gyrus; "PrG":
precentral gyrus; "PCL": paracentral lobule; "STG": superior temporal
gyrus; "MTG": middle temporal gyrus; "ITG": inferior temporal gyrus;
"FuG": fusiform gyrus; "PhG": parahippocampal gyrus; "Psts": posterior
superior temporal sulcus; "SPL": superior parietal lobule; "IPL": inferior
parietal lobule; "Pcun": precuneus; "PoG": postcentral gyrus; "INS":
insular gyrus; "CG": cingulate gyrus; "MVOcC": medioventral occipital
cortex; "LOcC": lateral occipital cortex; "Amyg": amygdala; "Hipp":
hippocampus; "BG": basal ganglia). ROIs are displayed with hemisphere,
initial seed mask area where the parcel was derived (naming convention
applied in the main text), and the parcel name from the Brainnetome
atlas (in brackets). Data are presented as the percentage of subjects
showing a W-score > 2.5 (%) with the median W-score in parentheses.
Regions representing the pre-acceleration period are #1 to #23; regions
representing the acceleration period are #24 to #146; and regions
representing the post-amplification period are #147 to #213. Regions
in bold font (#7 and #22) are the two leading propagation hubs.

| # | | ROI | % (W) |
|---|---|---|---|
| 180 | R | PrG 5 [A4tl] | 4.0 (0.1) |
| 181 | L | CG 2 [A24rv] | 4.0 (0.1) |
| 182 | L | MVOcC 5 [vmPOS] | 4.0 (0.1) |
| 183 | L | INS 3 [dIa] | 4.0 (0.1) |
| 184 | R | MVOcC 1 [cLinG] | 4.0 (0.1) |
| 185 | R | PoG 2 [A1/2/3tonIa] | 4.0 (0.0) |
| 186 | R | PoG 4 [A1/2/3tru] | 4.0 (0.0) |
| 187 | R | INS 1 [G] | 4.0 (0.0) |
| 188 | L | SPL 4 [A7pc] | 4.0 (0.0) |
| 189 | L | IFG 1 [A44d] | 3.5 (0.2) |
| 190 | L | INS 6 [dId] | 3.5 (0.2) |
| 191 | L | IFG 5 [A44op] | 3.5 (0.1) |
| 192 | L | OrG 6 [A12/47l] | 3.5 (0.1) |
| 193 | L | STG 3 [TE1.0/TE1.2] | 3.5 (0.1) |
| 194 | L | PoG 2 [A1/2/3tonIa] | 3.5 (0.1) |
| 195 | R | IFG 5 [A44op] | 3.5 (0.1) |
| 196 | L | PrG 1 [A4hf] | 3.5 (0.1) |
| 197 | R | PrG 1 [A4hf] | 3.5 (0.1) |
| 198 | R | INS 5 [dIg] | 3.5 (0.1) |
| 199 | R | INS 4 [vId/vIg] | 3.5 (0.1) |
| 200 | R | CG 2 [A24rv] | 3.5 (0.0) |
| 201 | R | PoG 1 [A1/2/3ulhf] | 3.5 (0.0) |
| 202 | L | PrG 6 [A6cvl] | 3.1 (0.2) |
| 203 | R | MVOcC 2 [rCunG] | 3.1 (0.1) |
| 204 | L | INS 1 [G] | 3.1 (0.1) |
| 205 | L | PrG 2 [A6cdl] | 3.1 (0.1) |
| 206 | L | INS 5 [dIg] | 3.1 (0.1) |
| 207 | L | SFG 3 [A9l] | 3.1 (0.1) |
| 208 | R | PrG 3 [A4ul] | 3.1 (0.0) |
| 209 | L | PoG 1 [A1/2/3ulhf] | 3.1 (0.0) |
| 210 | L | IFG 6 [A44v] | 2.6 (0.2) |
| 211 | L | MVOcC 3 [cCunG] | 2.6 (0.0) |
| 212 | R | LOcC 3 [OPC] | 2.6 (0.0) |
| 213 | L | PrG 5 [A4tl] | 2.2 (0.1) |

Human post-mortem[46,47] in vivo brain imaging[29,30,48], and model-based[49,50] studies have converged to suggest that tau spreads transneuronally within large-scale networks in AD and other tau-based disorders. We and others have used the normative functional and structural connectome to predict the spatial patterning and spread of atrophy[30,48,51], and early tau-PET studies suggest connectivity-related tau patterning in AD[16,52,53]. Here, we used diffusion tensor imaging to construct a normative "connectome", a matrix describing the group-level structural connectivity between each pair of brain regions, and we used this connectome to create a network flow-based model for simulating tau propagation along region-to-region macro-scale connections (FIG. 2A). This model enabled us to identify brain regions likely to promote widespread tau aggregation (henceforth, "propagation hubs") and to clarify how Aβ deposition relates to initial and accelerated tau spreading.

Example 3. Network-Based Tau Spreading is Accelerated at the ITG Areas

Figures 3A, 3B:
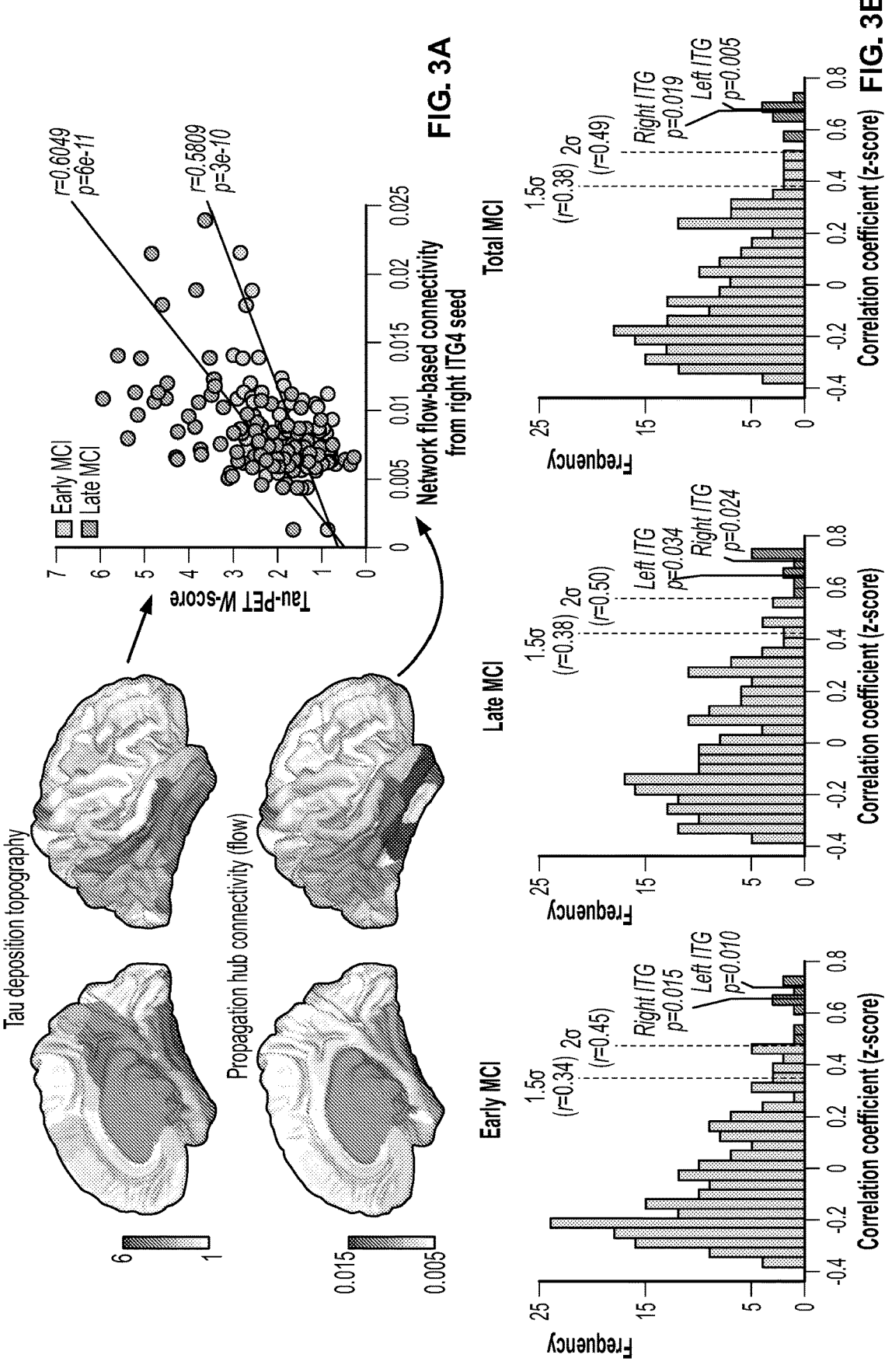
FIG. 3A-3B depict that inferior temporal gyrus connectivity mirrors tau acceleration phase topography.
Figure 9:
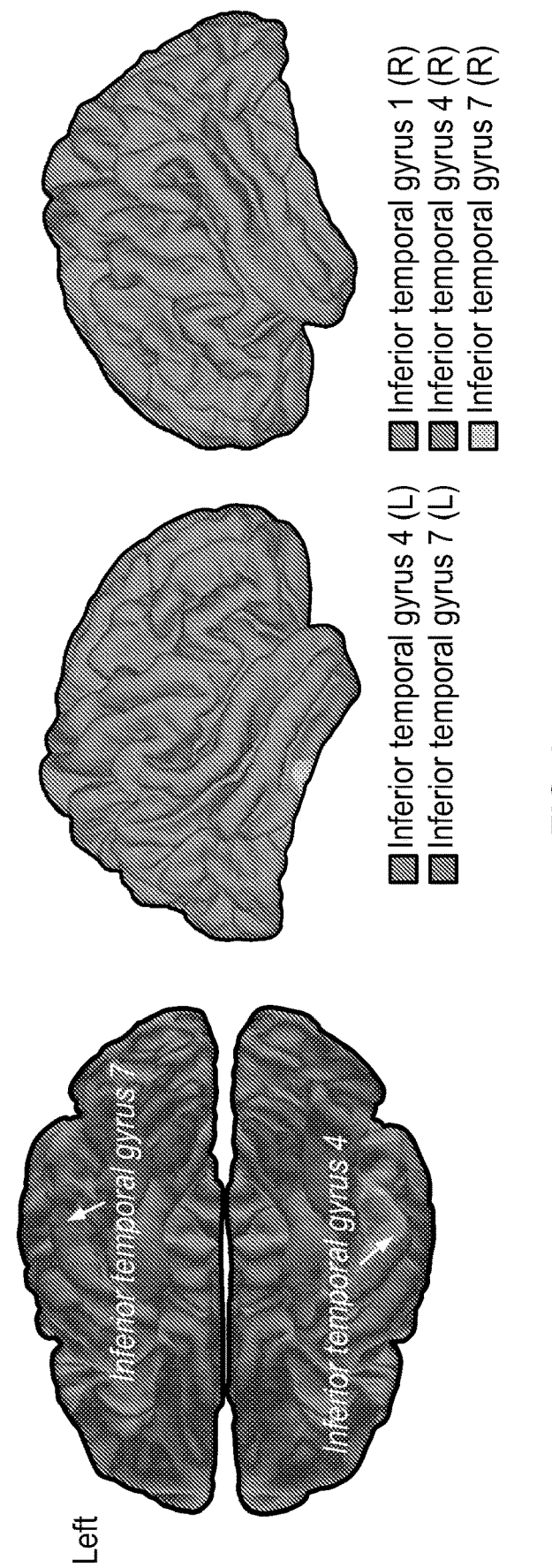
FIG. 9 depicts the identified tau propagation hubs using the Korean validation dataset. Five regions were identified as propagation hubs, including the ADNI-derived propagation hubs (the right ITG 4 and the left ITG 7), all within the ITG or adjacent temporal regions bilaterally.
Figure 10A:
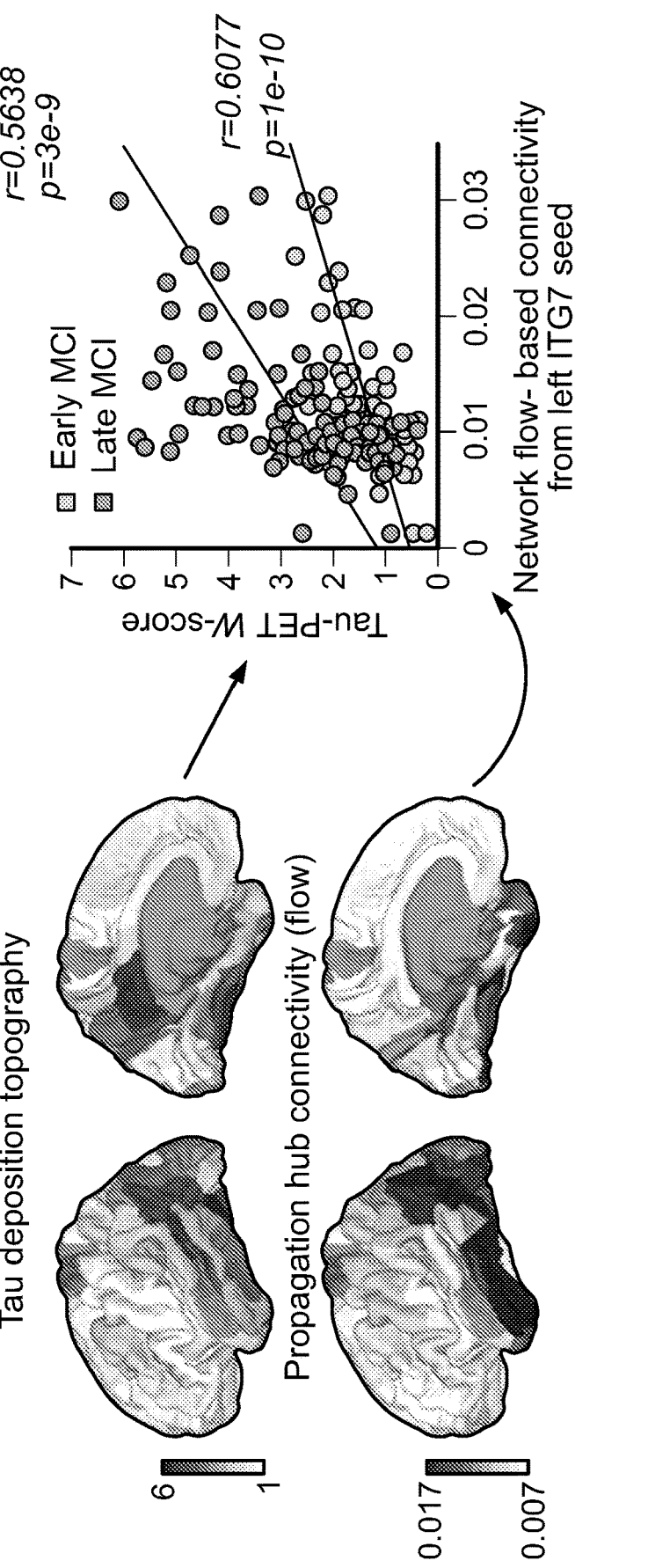
FIG. 10A-10C depicts additional findings, methodological validation, and replication of identified propagation hubs.
Figure 10B:
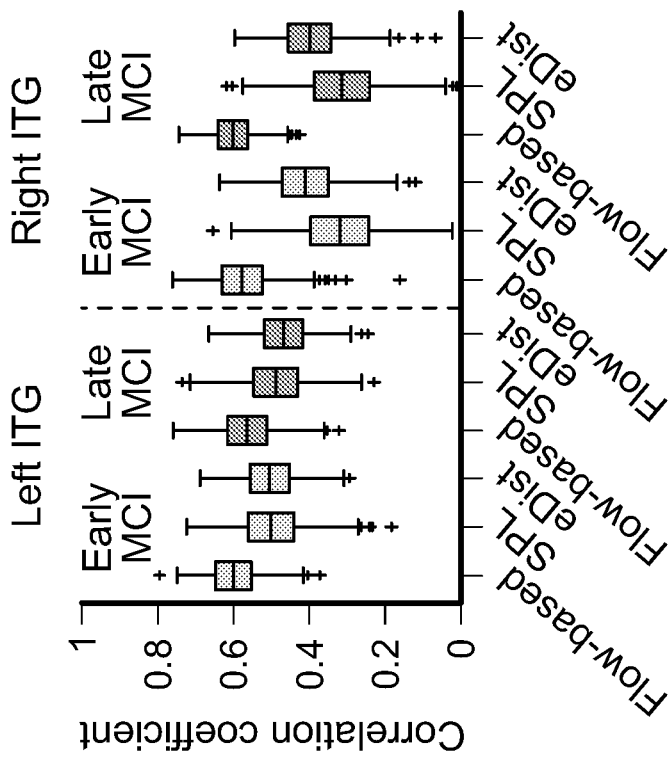
Figure 10C:
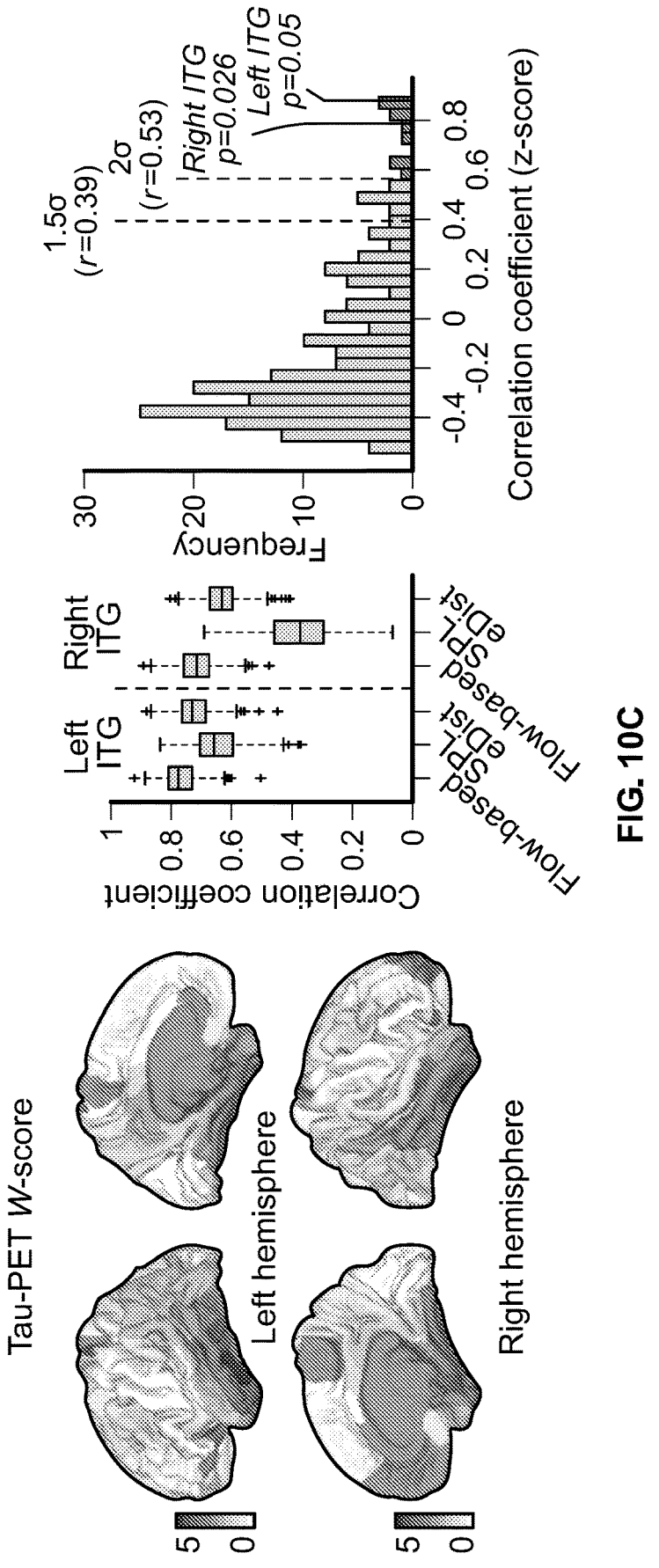

Applying the principles of graph theory, we modeled connectivity-mediated tau spreading based on maximum inter-nodal flow, which considers multiple distinct paths between any two nodes (FIG. 2A). We then searched the entire pool of regions, brain-wide, with the goal of identifying tau propagation hubs. Specifically, we searched a library of network flow-based connectivity maps, each based on a candidate brain region or "seed", assembled for the study using the normative structural connectome (FIG. 2B). We estimated the goodness-of-fit (GOF) of each seed's map to the regions representing the tau acceleration phase. We captured the topography of the tau acceleration phase by generating seven pairs of binary inner and outer masks across a range of spatial extents. Masks were gradually expanded to mimic tau propagation (FIG. 13) and to avoid potential influence of arbitrary mask definition. Finally, we identified propagation hubs, using a stringent set of criteria, as those nodes with significant GOF scores (permutation-based one-sample t-test, Bonferroni corrected $p<0.05$) across all seven inner/outer mask pairs (see Example 1). Using this brain-wide search strategy, the left and right inferior temporal gyri (ITG) emerged, independently, as propagation hubs (FIG. 2C), and this finding was stable after varying the total number of inner/outer mask pairs used to represent the acceleration phase (see Table 6 below). As expected based on our approach, the network flow-based connectivity maps seeded by these ITG propagation hubs were strongly correlated with the topography of tau deposition in early and late MCI (FIG. 3A, FIG. 10A), and those correlations were stronger than seen for other brain regions (based on null hypothesis distributions, FIG. 3B). Compared to other network-based propagation models assessed in our previous work[29,30], the network flow-based model produced the highest correlations between the ITG propagation hub connectivity pattern and the observed tau deposition topography in both early and late MCI (see FIG. 10B), justifying our use of the network flow-based model for propagation hub identification. Applying the same propagation hub identification procedure to the Korean validation dataset, we again identified the two ADNI-derived ITG areas, and the connectivity of these regions correlated strongly with the pattern of tau deposition in the Korean MCI subjects (FIG. 10C). We also identified ten additional putative propagation hubs, nearly all within the ITG or adjacent basal temporal regions bilaterally (see FIG. 9). Because tau-PET image analysis methods continue to evolve, we also reproduced these key findings after varying several methodological steps that remain unsettled in the field (see Table 7 and Table 8 below).

TABLE 6

Propagation hubs identified using alternative numbers of inner/out mask pairs to represent the acceleration phase regions.

| Number of mask pairs | Incremental size | Identified propagation hubs |
|---|---|---|
| 7 (main results) | 10 | ITG7 (L), ITG4 (R) |
| 5 | 15 | ITG7 (L), ITG7 (R), ITG1 (L), ITG4 (R) |
| 4 | 20 | ITG7 (R), ITG4 (R), ITG7 (L), ITG1 (R), ITG2 (R) |
| 3 | 30 | ITG7 (L), ITG7 (R), ITG1 (L), ITG4 (R), ITG1 (R), ITG2 (R) |

TABLE 7

Results comparison after using an alternative tau-PET reference region ("ROI": region of interest; "L": left; "R": right; "ITG": inferior temporal gyrus; "FuG": fusiform gyrus; "MTG": middle temporal gyrus; "EC": entorhinal cortex; "eMCI": early mild cognitive impairment; "lMCI": late mild cognitive impairment; "CN": cognitively normal; "AD": Alzheimer's disease; "−": Aβ-negative; "+": Aβ-positive). P-values were corrected for multiple comparison using the false discovery rate method[54].

| | Main results | Reproduced results |
|---|---|---|
| Reference region | Whole cerebellum | Inferior grey cerebellum |
| Off-target regions | 33 ROIs from Gaussian mixture modeling | 29 ROIs from Gaussian mixture modeling (All involved in the equivalent main results) |
| Connectome | | Identical |
| Initial mask size | 30 (# of mask pairs: 7) | 40 (# of mask pairs: 7) |
| Identified propagation hubs | ITG7 (L), ITG4 (R) | ITG7 (L), ITG1 (L), ITG4 (L), FuG3 (L), ITG2 (L), ITG6 (L), MTG3 (L), ITG7 (R), ITG5(L), ITG1 (R), ITG4 (R), ITG3 (L) (ordered by mean t-statistics) |
| Correlation between ITG propagation hub flow-based connectivity and tau W-map | [eMCI] 0.61 (L), 0.58 (R) [lMCI] 0.56 (L), 0.60 (R) [eMCI + lMCI] 0.61 (L), 0.61 (R) | [eMCI] 0.58 (L), 0.53 (R) [lMCI] 0.55 (L), 0.59 (R) [eMCI + lMCI] 0.59 (L), 0.58 (R) |

TABLE 7-continued

Results comparison after using an alternative tau-PET reference region ("ROI": region of interest;
"L": left; "R": right; "ITG": inferior temporal gyrus; "FuG": fusiform gyrus;
"MTG": middle temporal gyrus; "EC": entorhinal cortex; "eMCI": early mild cognitive
impairment; "lMCI": late mild cognitive impairment; "CN": cognitively normal; "AD": Alzheimer's
disease; "−": Aβ-negative; "+": Aβ-positive). P-values were corrected for multiple
comparison using the false discovery rate method[54].

| | Main results | Reproduced results |
|---|---|---|
| Remote interaction [EC] | [Aβ-tau]<br>t: 3.63, p: 0.001 (L) /<br>t: 2.61, p: 0.017 (R)<br>[Aβ-PRNP→tau-FYN]<br>t: 5.23, p: <0.001 (L) /<br>t: 4.72, p: <0.001 (R) | [Aβ-tau]<br>t: 4.22, p: <0.001 (L) /<br>t: 3.21, p: 0.003 (R)<br>[Aβ-PRNP→tau-FYN]<br>t: 5.22, p: <0.001 (L) /<br>t: 4.83, p: <0.001 (R) |
| Local interaction [ITG propagation hubs] | [Aβ-tau]<br>t: 3.77, p: <0.001 (L) /<br>t: 4.28, p: <0.001 (R)<br>[Aβ-PRNP-tau-FYN]<br>t: 4.03, p: <0.001 (L) /<br>t: 4.42, p: <0.001 (R) | [Aβ-tau]<br>t: 3.77, p: <0.001 (L) /<br>t: 4.29, p: <0.001 (R)<br>[Aβ-PRNP-tau-FYN]<br>t: 4.03, p: <0.001 (L) /<br>t: 4.30, p: <0.001 (R) |

| | | CN− | CN+ | eMCI+ | lMCI+ | AD+ | | CN− | CN+ | eMCI+ | lCMI+ | AD+ |
|---|---|---|---|---|---|---|---|---|---|---|---|---|
| Therapeutic | 1 | 111 | 59 | 13 | 6 | 2 | 1 | 110 | 57 | 14 | 7 | 2 |
| group | 2 | 4 | 8 | 7 | 4 | 0 | 2 | 4 | 10 | 6 | 4 | 1 |
| assignments | 3 | 0 | 0 | 8 | 7 | 7 | 3 | 1 | 0 | 8 | 6 | 6 |

TABLE 8

Summary of reproduced results using alternative approach to off-target tau-PET binding
("ROI": region of interest; "L": left; "R": right; "ITG":
inferior temporal gyrus; "Psts": posterior superior temporal sulcus; "MTG": middle
temporal gyrus; "IPL": inferior parietal lobule; "FuG": fusiform gyrus;
"MVOcC": medioventral occipital cortex; "EC": entorhinal cortex; "eMCI": early
mild cognitive impairment; "lMCI": late mild cognitive impairment; "aMCI": amnestic
mild cognitive impairment). P-values were corrected for multiple comparison using the false
discovery rate method[54].

| Reference region | Main results | Reproduced results<br>Identical |
|---|---|---|
| Off-target regions | 33 ROIs from Gaussian mixture modeling<br>(Table 3A) | Hippocampus and subcortical areas<br>(Table 3B) |
| Connectome | | Identical |
| Initial mask size | 30 (# of mask pairs: 7) | 40 (# of mask pairs: 7) |
| Identified propagation hubs | ITG7 (L), ITG4 (R) | ITG7 (L), Psts2 (L), MTG3 (L), ITG4<br>(L), ITG1 (L), ITG6 (L), ITG4 (R),<br>IPL4 (L), ITG7 (R), Psts1 (L)<br>(ordered by mean t-statistics) |
| Correlation between ITG propagation hub flow-based connectivity and tau W-map | [eMCI] 0.61 (L), 0.58 (R)<br>[lMCI] 0.56 (L), 0.60 (R)<br>[eMCI + lMCI] 0.61 (L), 0.61 (R) | [eMCI] 0.60 (L), 0.61 (R)<br>[lMCI] 0.56 (L), 0.62 (R)<br>[eMCI + lMCI] 0.60 (L), 0.63 (R) |
| Remote interaction [EC] | [Aβ-tau]<br>t: 3.63, p: 0.001 (L)/t: 2.61, p: 0.017<br>(R)<br>[Aβ-PRNP→tau-FYN]<br>t: 5.23, p: <0.001 (L)/t: 4.72,<br>p: <0.001 (R) | [Aβ-tau]<br>t: 3.75, p: 0.001 (L)/t: 2.50, p: 0.020<br>(R)<br>[Aβ-PRNP→tau-FYN]<br>t: 5.25, p: <0.001 (L)/t: 4.71,<br>p: <0.001 (R) |
| Local interaction [ITG propagation hubs] | [Aβ-PRNP-tau-FYN]<br>t: 3.77, p: <0.001 (L)/t: 4.28,<br>p: <0.001 (R)<br>[4-way]<br>t: 4.03, p: < 0.001 (L)/t: 4.42,<br>p: <0.001 (R) | [Aβ-PRNP-tau-FYN]<br>t: 3.79, p: < 0.001 (L)/t: 4.29,<br>p: <0.001 (R)<br>[4-way]<br>t: 4.09, p: < 0.001 (L)/t: 4.43,<br>p: <0.001 (R) |
| Therapeutic group assignments | | Identical |

Figures 4A, 4B:
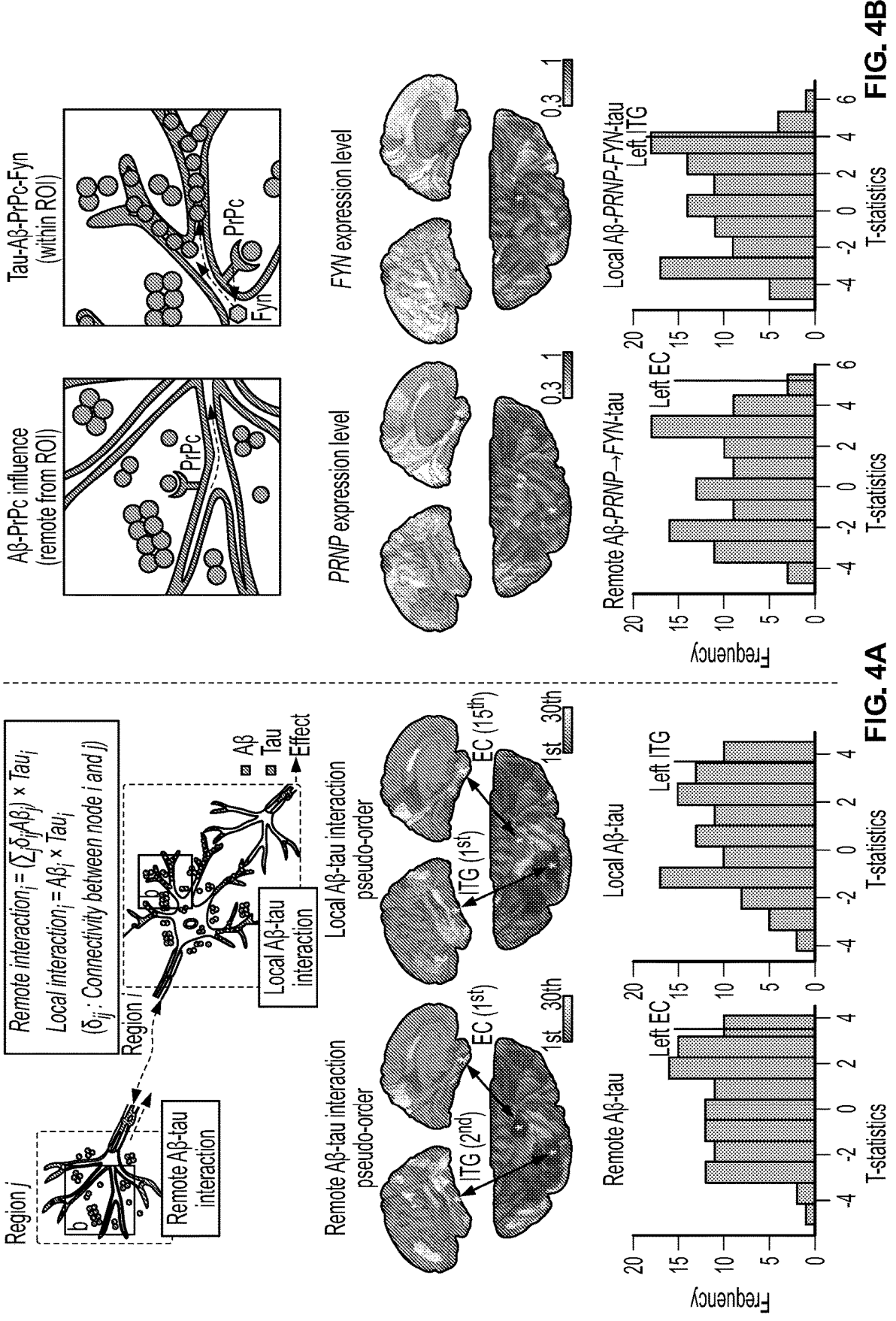
FIG. 4A-4B depict a network-based Aβ-tau interaction model.

Example 4. Remote and Local Amyloid-β-Tau Interactions Drive Onset and Acceleration in Tau Spreading AD has been conceptualized as an Aβ-triggered tauopathy[55], but to date it has been difficult to reconcile this concept with the topographical discordance between early Aβ and tau deposition in humans. Having identified the bilateral ITG regions as tau propagation hubs, we sought to determine whether and how cerebral Aβ-deposition might induce and accelerate tau spreading. To this end, we developed a network-based protein-protein interaction model to estimate two types of Aβ-tau interaction: remote and local (FIG. 4A). Remote interactions were conceived as arising from each tau-positive region's connectivity to Aβ-positive regions. More specifically, we imagined that tau-positive regions contain tau-positive neurons, whose axons travel to and form synapses with neurons residing in Aβ-positive regions. Specific Aβ species may, in turn, prove toxic to those synapses or may otherwise influence axons arriving from or departing to remotely connected, tau-positive neurons, thereby triggering a long-range interaction with the tau-positive region. Local interaction, on the other hand, was conceived as the direct comingling of parenchymal Aβ and aggregating neuritic tau within a given brain region[56].

Figure 11:
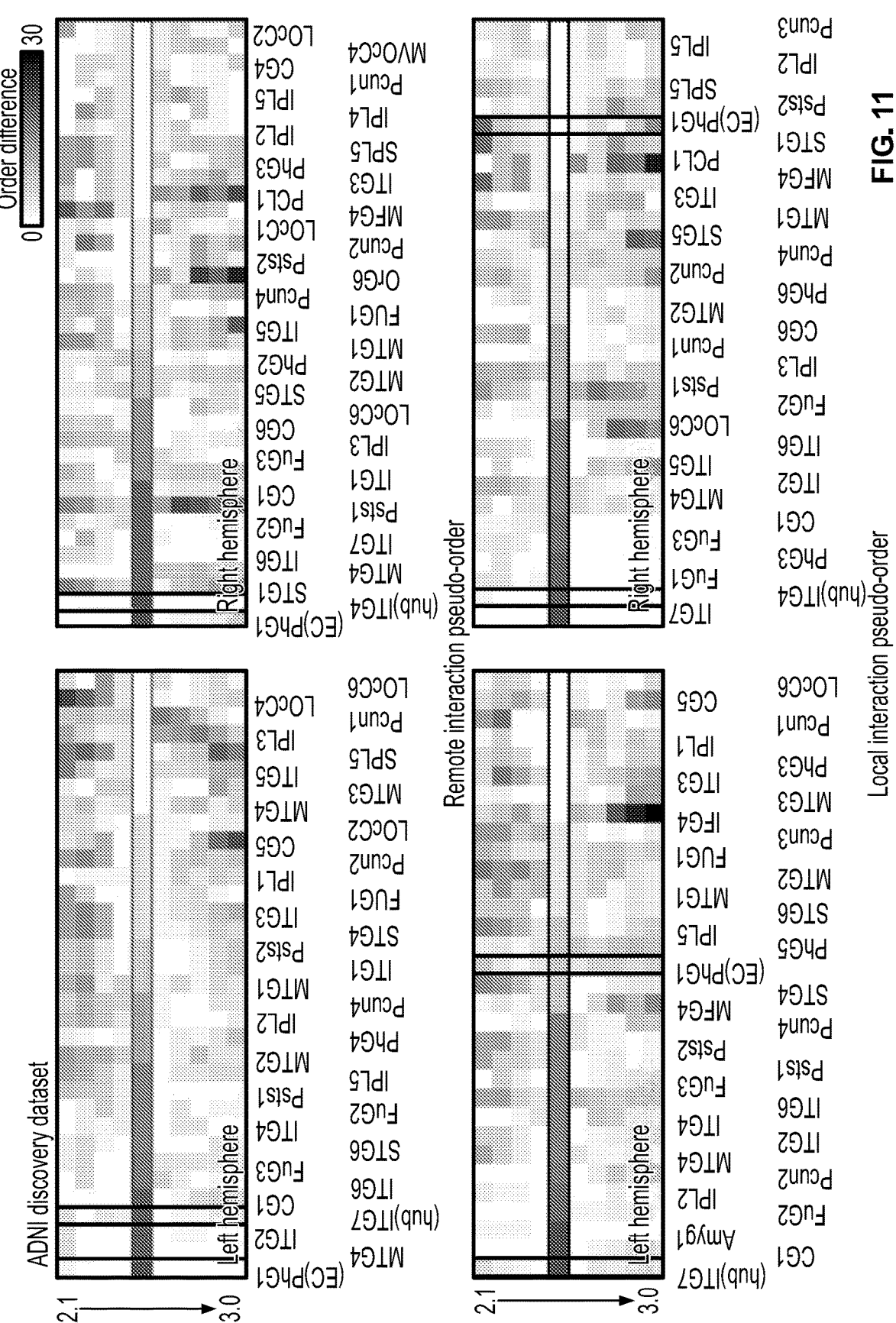
FIG. 11 depicts remote and local interaction pseudo-order
plotted against a range of tau W-score cutoffs. The pseudo-order for each hemisphere was obtained using the standard
regional Aβ SUVR cutoff and each tau W-score cutoff
between 2.1 and 3.0 (inclusive) with an interval of 0.1.
Regions of interests (ROIs) in the top 30 were aligned by
their pseudo-order at the chosen tau W-score threshold of
2.5, and differences in order were computed between this
threshold and the others. A red-yellow color bar in the center
of each map represents the pseudo-order at tau W-score
threshold of 2.5, with deeper hues representing earlier
regions. The grayscale color bar indicates the absolute value
of the change in order (if any) at the alternative threshold.
EC, entorhinal cortex; PhG, parahippocampal gyrus; MTG,
middle temporal gyrus; ITG, inferior temporal gyrus; FuG,
fusiform gyrus; STG, superior temporal gyrus; Psts, poste-
rior superior temporal sulcus; IPL, inferior parietal lobule;
LOcC, lateral occipital cortex; Hipp, hippocampus; Pcun,
precuneus; CG, cingulate gyrus; MFG, middle frontal gyrus;
OrG, orbital gyrus; PCL, paracentral lobule; Amyg,
amygdala
Figure 11:
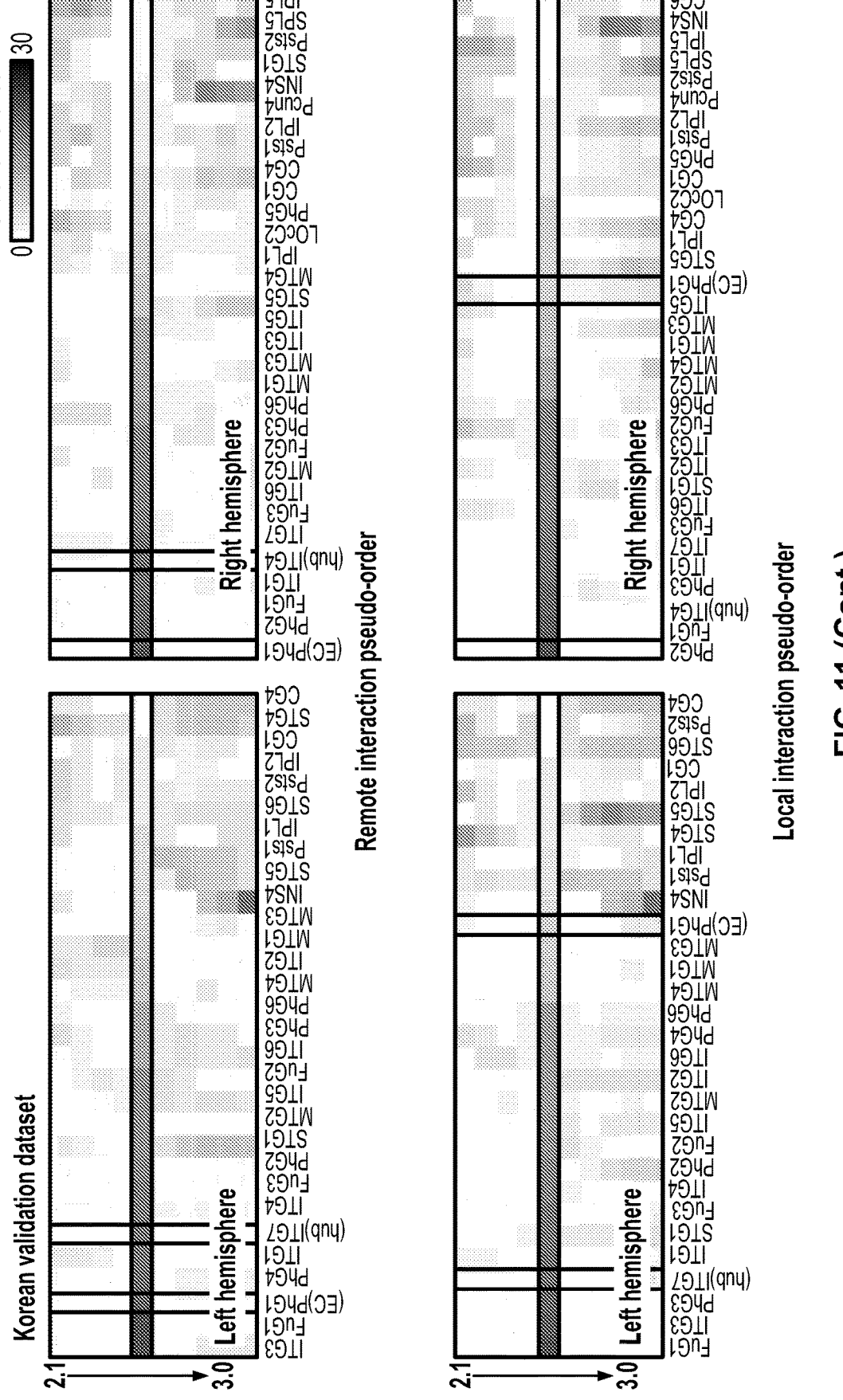
Figure 12A:
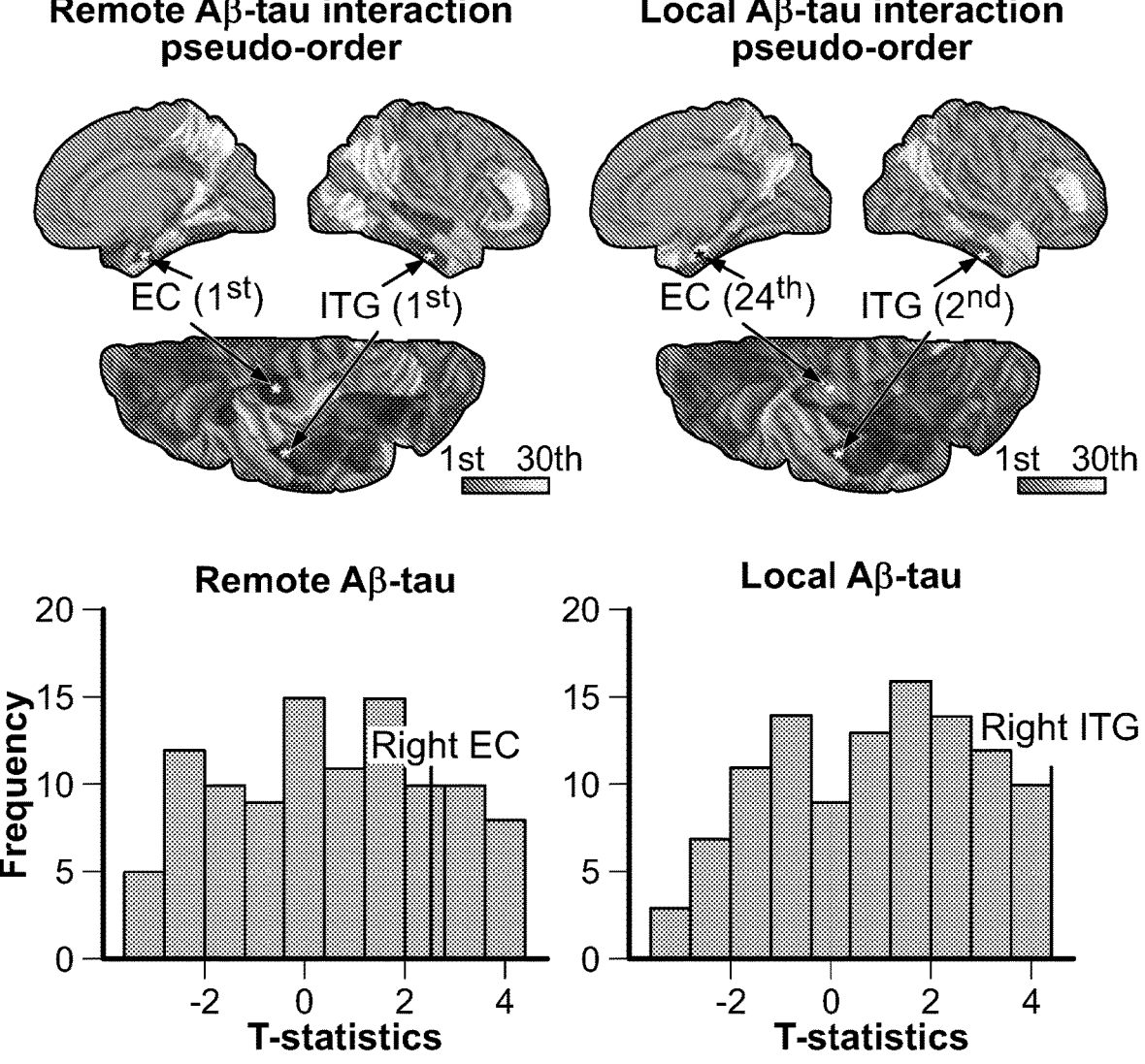
FIG. 12A-12C depicts extension and replication of protein-protein interaction model findings.
Figure 12B:
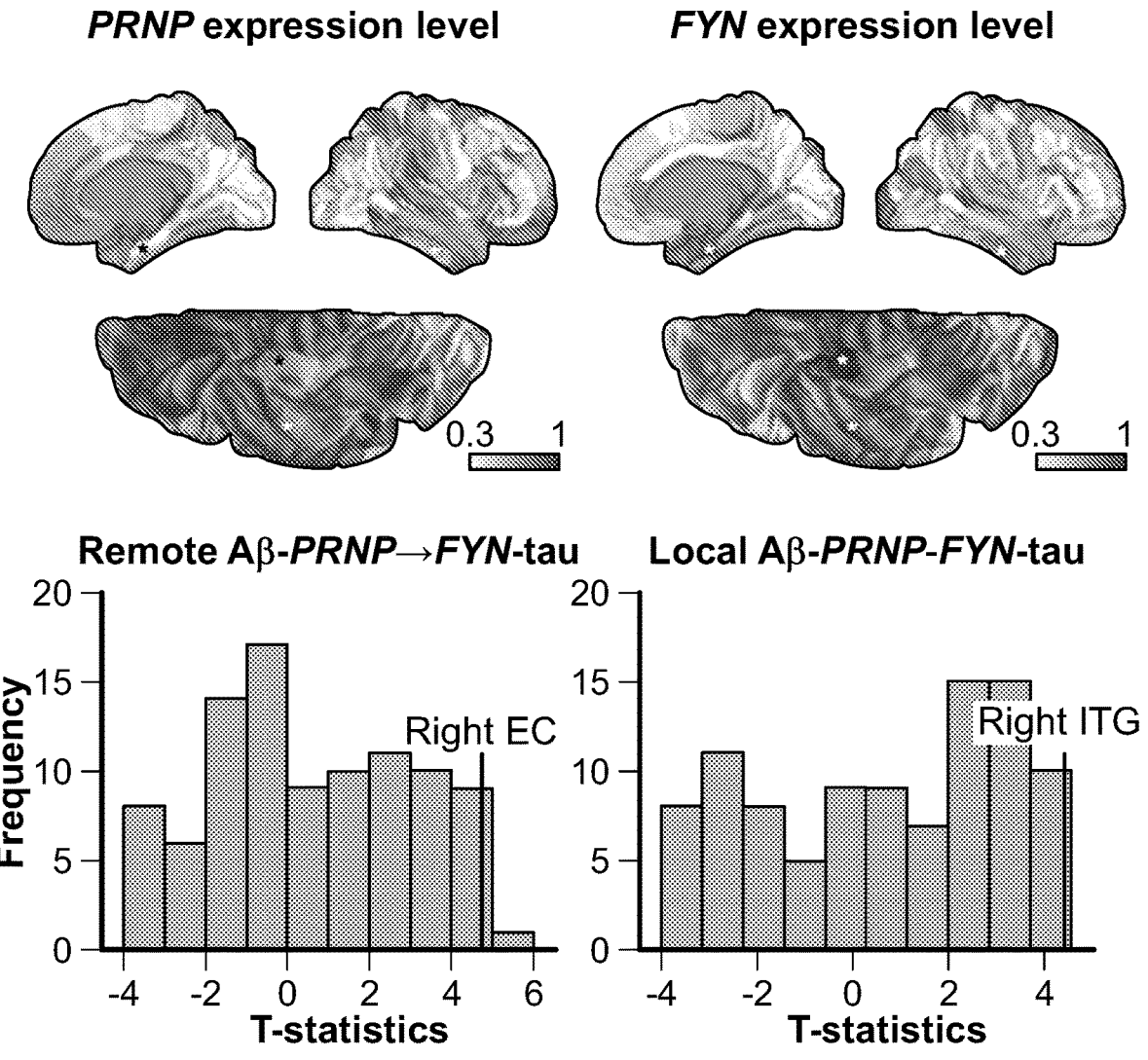
Figure 12C:
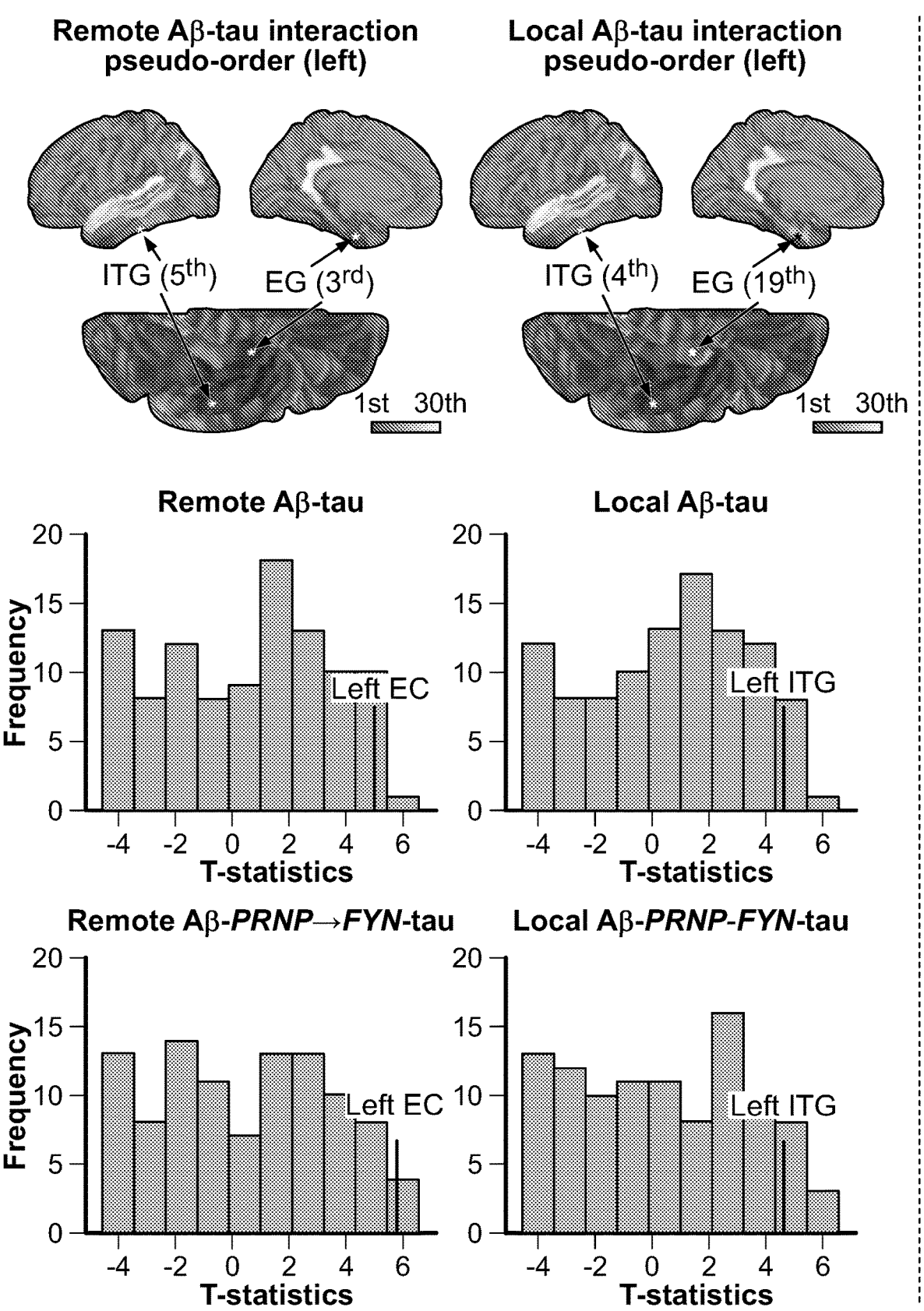

Calculation of remote Aβ-tau interactions required three steps. First, we calculated each region-of-interest's weighted connectivity strength, derived from the healthy structural connectome, to all other regions. Second, we multiplied each connectivity strength by the magnitude of Aβ-deposition within the connected region and summed these products to calculate a connectivity-weighted remote Aβ influence metric. Finally, the remote Aβ influence metric was multiplied by the magnitude of tau deposition within the region-of-interest (FIG. 4A). To rank regions according to their remote Aβ-tau interactions, we again applied the frequency distribution method, assuming that regions with the earliest remote Aβ-tau interactions would show suprathreshold scores in the largest proportion of patients. Using this approach, we found that the lateral entorhinal cortex (EC; [A35/36r]) ranked first among 213 brain regions (FIG. 4A). Based on absolute levels, the lateral EC showed significantly greater remote Aβ-tau interaction than the median of all other brain regions (t: 3.63/2.61, FDR-corrected p-value: 0.001/0.017, left/right EC). This finding was stable across a range of tau W-score thresholds (FIG. 11) and alternative tau-PET analysis methods (Table 7 and Table 8) and was broadly replicated in the Korean validation dataset, in which the lateral EC had the highest median remote Aβ-tau interaction rank of any brain region (EC left: $3^{rd}$, EC right: $1^{st}$, median $2^{nd}$; FIG. 11 and FIG. 12).

To calculate local Aβ-tau interactions, we multiplied each region's local Aβ deposition (amyloid-PET SUVR value) by its tau-PET W-score. Although the procedures for calculating local Aβ-tau interactions and those for identifying propagation hubs were completely independent, the left and right ITG propagation hubs emerged as the highest-ranking regions, brain-wide, for local Aβ-tau interaction (FIG. 4A). Local Aβ-tau interaction scores for the left and right ITG were significantly greater than the median of all other regions (t: 3.77/4.28, FDR-corrected p-value: <0.0001/ <0.001, left/right ITG). This finding was stable across a range of tau W-score thresholds (FIG. 11) and alternative tau-PET analysis methods (Table 7 and Table 8). The finding was also broadly reproduced in the Korean validation dataset (FIG. 11 and FIG. 12), in which the ITG hubs for each hemisphere ranked in the top 4 for local Aβ-tau interaction within that hemisphere (ITG7, right: $4^{th}$; ITG4, left: $3^{rd}$), with the few higher ranking regions being adjacent basal temporal areas.

Several molecules and pathways have been proposed to cultivate local Aβ-tau interactions or increase the toxicity of those interactions. Recent evidence from mouse models and human post-mortem brain tissue implicates the cellular prion protein (PrPc, encoded by PRNP) and the Src tyrosine kinase Fyn (encoded by FYN) in this process[37,38]. More specifically, some have proposed that oligomeric Aβ binds to PrPc, a membrane-anchored glycoprotein, which initiates a signaling cascade that activates Fyn. Fyn, in turn, promotes tau post-translational modifications that increase tau misfolding and aggregation. We therefore asked whether, and to what degree, PRNP and FYN are expressed within brain regions showing heightened Aβ-tau interactions. To address this question, we used the Allen Human Brain Atlas microarray dataset, from which we derived mRNA expression levels for PRNP and FYN, co-registered these data to the neuroanatomical atlas used throughout this study, and mapped the PRNP and FYN expression levels on the cortical surface (FIG. 4B). Interestingly, although the ITG showed high expression of both genes, the lateral EC, where the earliest tau deposition and remote Aβ-tau interactions occur, showed low PRNP expression despite having the second highest average FYN expression level brain-wide (see FIG. 4B). This spatial incongruity raises the possibility that Aβ exerts its remote effects on EC tau by interacting with PrPc expressed in distal EC axons as they (reciprocally) project back to Aβ-positive neocortical areas, in which local PRNP expression is moderate to high. To gain support for this concept, we asked whether the lateral EC is distinguished by having not only early tau deposition and high baseline FYN expression but also strong connectivity to regions where Aβ and PrPc can interact. We calculated, for each region-of-interest, the joint Aβ-PRNP expression level within the region's connected areas, weighted by the strength of those connections, and multiplied that Aβ-PRNP influence metric by the region-of-interest's local tau W-score and FYN expression level (denoted Aβ-PRNP→tau-FYN). The lateral EC areas showed greater Aβ-PRNP→tau-FYN interaction scores than the median score of all other brain regions (t: 5.23/4.72, FDR-corrected p-value: <0.0001/<0.0001, left/ right EC; FIG. 4B). Next, turning to the identified ITG propagation hubs, we asked whether these hubs stand out as regions where pathological Aβ and tau interact locally with PRNP and FYN. We therefore calculated 4-molecule interaction scores in which the local Aβ-tau interaction score was multiplied by PRNP and FYN expression levels for each region. The ITG propagation hubs showed greater interaction scores than the median 4-molecule interaction scores of all the other brain regions (t: 4.03/4.42, FDR-corrected p-value: <0.0001/<0.001, left/right ITG). These findings suggest that the ITG, in addition to having a connectional profile poised to disseminate tau during the tau acceleration phase, is home to a fertile molecular landscape for local Aβ-tau-PrP-Fyn interactions that promote tau misfolding and may further enhance tau seeding and spreading behavior. These findings were strongly replicated in the Korean validation dataset (FIG. 12C) and across alternative tau-PET analysis methods (Table 7 and Table 8).

Example 5. Longitudinal Tau Aggregation Trajectories Support the Aβ-Tau Interaction Model In the preceding analyses, we used cross-sectional data to make longitudinal inferences about the natural history of AD. This strategy enabled us to derive a tau regional spreading order based on a sufficient sample size; nonetheless, the pseudo-longitudinal approach cannot directly test the within-subjects temporal predictions made by our model. To address this limitation, we collected all subjects in the ADNI (n=135) and Korean (n=169) cohorts who had undergone at least one follow-up structural MRI and tau-PET scan (Table 1). Because the two longitudinal samples were relatively small, we combined them into a single ADNI/Korean longitudinal MCI cohort after regularizing the two datasets separately using the W-score approach (see Example 1). Using this combined cohort, we first determined the regional tau accumulation rate, defined as the annualized change in the tau-PET W-score. As expected, tau accumulation in subjects with $A\beta$+ MCI (n=68) is most prominent in basal temporal areas and, to a lesser extent, fronto-parietal heteromodal association cortices (FIG. 15A). Next, we returned to our library of normative network flow-based maps, one derived from each brain region, to determine the spatial correlation between each region's connectivity pattern and the longitudinal tau accumulation seen in $A\beta$+ MCI. Remarkably, mirroring the cross-sectional findings, the ITG regions again stood out as the regions whose connectivity best matched the longitudinal tau accumulation pattern (FIG. 15A).

Next, to test the longitudinal predictions arising from the $A\beta$-tau interaction components of our model, we established quantitative thresholds for $A\beta$- and tau-PET positivity within each region brain-wide (see Example 1). We then used these thresholds to group subjects, irrespective of their clinical label, based on their baseline $A\beta$ and tau status in the bilateral EC and ITG regions-of-interest previously identified through the cross-sectional remote and local $A\beta$-tau interaction analyses. We quantified tau spreading into downstream regions by averaging the annualized tau accumulation rates within the 30 regions downstream of the regions-of-interest, based on the established tau spreading order (FIG. 1C and Table 5). For the EC, we predicted that downstream tau spreading would be greatest when the EC is tau-positive at baseline, with little influence by the local co-presence of Ap. Critically, however, our model predicts that regions downstream to the EC will show greater tau accumulation insofar as the EC is subjected to remote $A\beta$-tau interaction. Each of these EC-based predictions was supported by our longitudinal data (FIG. 15B; t: 0.32/–0.98, p-value: 0.749/0.330, left/right EC, for influence of local $A\beta$; Mann-Whitney U test Z: 1.73/2.73, one-tailed p-value: 0.041/0.003, left/right EC; for influence of remote $A\beta$, FIG. 15B inset). Regarding the ITG propagation hubs, our model predicts accelerated tau spreading when $A\beta$ and tau interact locally within the ITG. Here, we found that regions downstream to the ITG accumulated more tau in subjects who transitioned from having only $A\beta$ in the ITG to having both $A\beta$ and tau (FIG. 15C inset; Mann-Whitney U test Z: 4.23/4.04, p-value: <0.001/<0.001, left/right ITG, for the influence of emerging $A\beta$-tau co-positivity). Emergent $A\beta$-tau co-positivity in the ITG was invariably the result of an $A\beta$-positive ITG that became tau-positive at follow-up. The longitudinal EC and ITG findings reported here were stable across a range of downstream region numbers (Table 4).

Figures 6A, 6B, 6C, 6D:
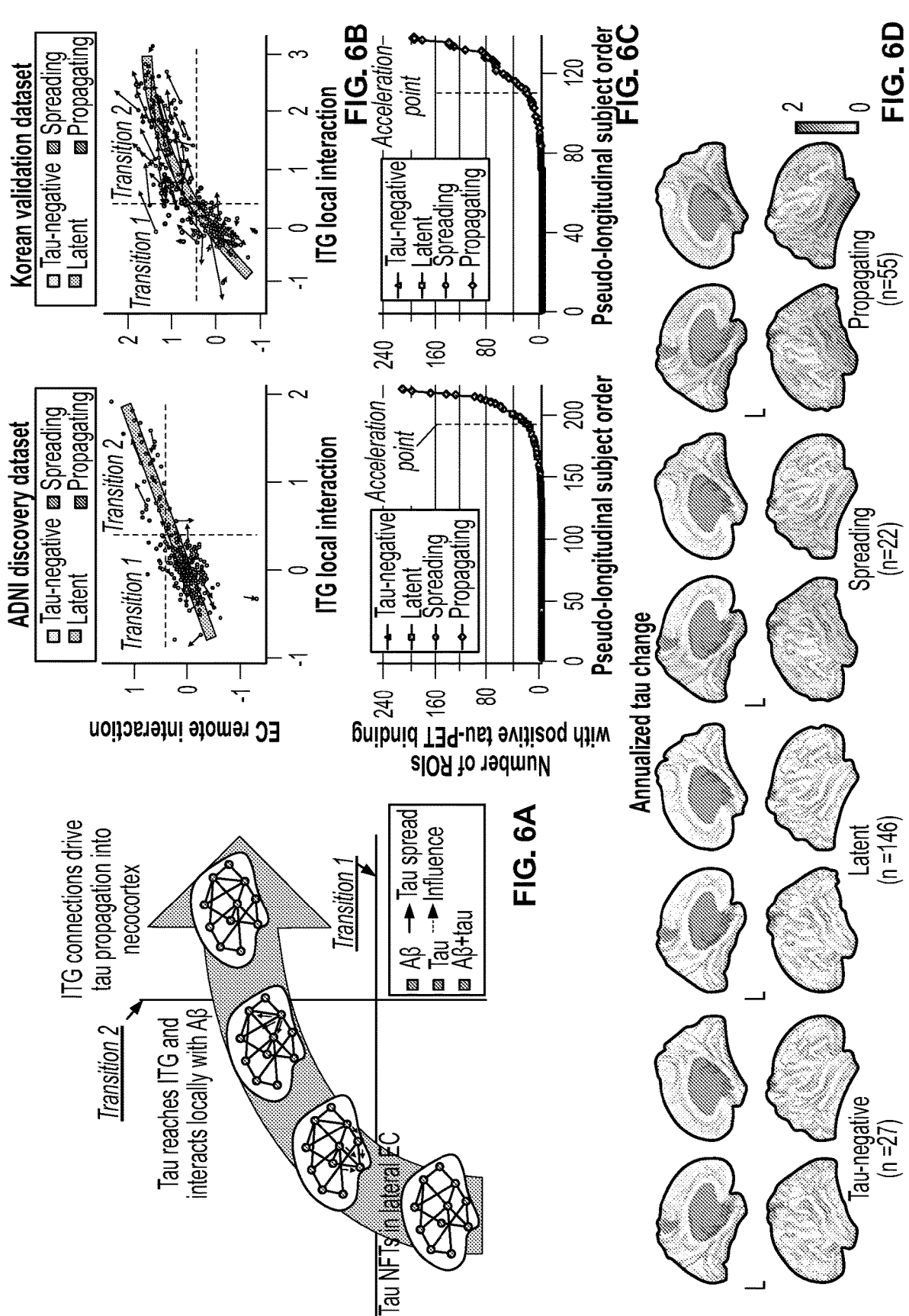
FIG. 6A-6D depict results showing that two Aβ-tau interactions define a fundamental arc of AD molecular-anatomical progression.

Example 6. Two Pivotal $A\beta$-Tau Interactions in the Natural History of AD The findings outlined above suggest two pivotal moments in the molecular-anatomical pathogenesis of AD. The first occurs when neocortical $A\beta$ emerges within multiple neocortical regions connected to the entorhinal cortices. This remote, connectionally mediated interaction between neocortical $A\beta$ and entorhinal cortex tau may induce tau to further misfold and spread out of the entorhinal areas and into nearby, connected regions in the hippocampus, amygdala, and basal temporal cortices. The second pivotal moment occurs when tau neurofibrillary changes reach the ITG, where tau locally interacts with pre-existing $A\beta$ to catalyze widespread tau propagation into other $A\beta$-positive and ITG-connected neocortical regions whose degeneration ultimately gives rise to dementia[53]. If these pivotal moments occur in sequence, as we hypothesize, then metrics capturing these two phenomena should obey a nonlinear relationship in which the EC remote $A\beta$-tau interaction rises first, before giving way to a rise in local $A\beta$-tau interaction within the ITG. Plotting these metrics across our discovery and validation cohorts strongly supported this prediction, demonstrating a fundamental arc of disease severity across individuals (FIG. 6A-B). Quadratic regression models based on the mean (left/right) values fit both datasets well (ADNI: $R^2$=0.71, Korean: $R^2$=0.70),[1] significantly better than did linear functions (ADNI: $R^2$=0.70/F (testing for the difference between quadratic and linear fit)=7.54, p=0.007; Korean: $R^2$=0.57/F=80.20, p=3e-16).

Figure 13:
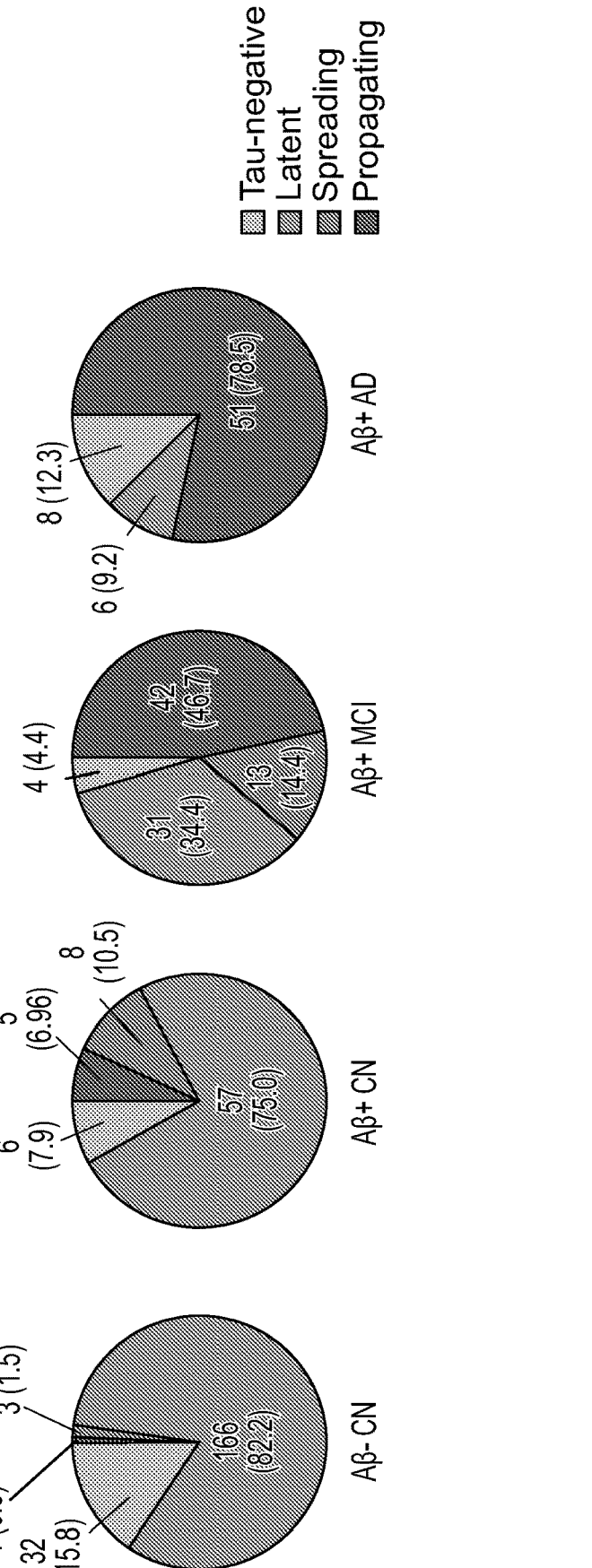
FIG. 13 depicts subject stratification assignments. Within
each biomarker-anchored clinical label, subjects from the
combined ADNI/Korean cross-sectional data were stratified
into four groups based on the method derived from the
Aβ-tau interaction model.

Based on the two pivotal $A\beta$-tau interactions, subjects could be stratified into one of four groups: (1) "tau-negative" in EC, (2) insufficient EC remote $A\beta$-tau interaction to promote tau spreading ("latent tau"), (3) sufficient EC remote $A\beta$-tau interaction but minimal ITG local $A\beta$-tau interaction ("spreading tau"), and (4) sufficient ITG local $A\beta$-tau interaction ("propagating tau") (FIG. 13 and Table 9 below). FIG. 6C shows subject stratification assignments overlaid on the pseudo-longitudinal subject order derived from the tau frequency distribution approach. Using this stratification method, subjects assigned to the "spreading tau" group fall just before or shortly after the start of the tau acceleration phase, whereas those designated "propagating tau" are nearly all found within the acceleration phase. As expected, longitudinal subjects within the "spreading" and, in particular, "propagating" tau groups showed dramatically greater whole-brain annualized tau accumulation (FIG. 6D). Expert recommendations for the use of the amyloid-lowering drug, aducanumab, emphasize the importance of positive AD biomarkers and a clinical label of MCI or mild dementia. Therefore, it is important to note that the model-driven subject stratification method presented here overlays inconsistently on the biomarker-anchored clinical groupings conventionally used in AD clinical trials (FIG. 13 and Table 9). For example, subjects in the "spreading tau" group, whom we hypothesize will benefit most from amyloid-lowering therapy, represented only 14.4% of the overall $A\beta$+ MCI group.

TABLE 9

Example use case: subject stratification. Data are represented as a number (%), based on tau status of the cross-sectional data

| Group | $A\beta$– CN (n = 202) | $A\beta$+ CN (n = 76) | $A\beta$+ MCI (n = 90) | $A\beta$+ AD (n = 65) |
|---|---|---|---|---|
| Tau-negative | 32 (15.8) | 6 (7.9) | 4 (4.4) | 0 (0.0) |
| Latent tau | 166 (82.2) | 57 (75.0) | 31 (34.4) | 8 (12.3) |
| Spreading tau | 3 (1.5) | 8 (10.5) | 13 (14.4) | 6 (9.2) |
| Propagating tau | 1 (0.5) | 5 (6.6) | 42 (46.7) | 51 (78.5) |

These findings resolve a long-standing question about the pathogenesis and progression of AD by placing early Aβ and tau interactions within a connectivity-based molecular-anatomical framework. This framework suggests that the natural history of AD traverses a critical period that begins once Aβ emerges within EC-connected neocortical regions, continues as tau spreads from the EC into connected mesial temporal and limbic regions, and ends when Aβ and tau interact within the ITG propagation hubs, whose connections and molecular makeup facilitate widespread neocortical tau propagation. This critical period may correspond to a therapeutic window for Aβ-lowering therapies, help to explain the repeated failure of Aβ-lowering clinical trials, and suggest a method for patient-tailored AD therapy.

Example 7. A Network-Based Therapeutic Window

Figures 5A, 5B:
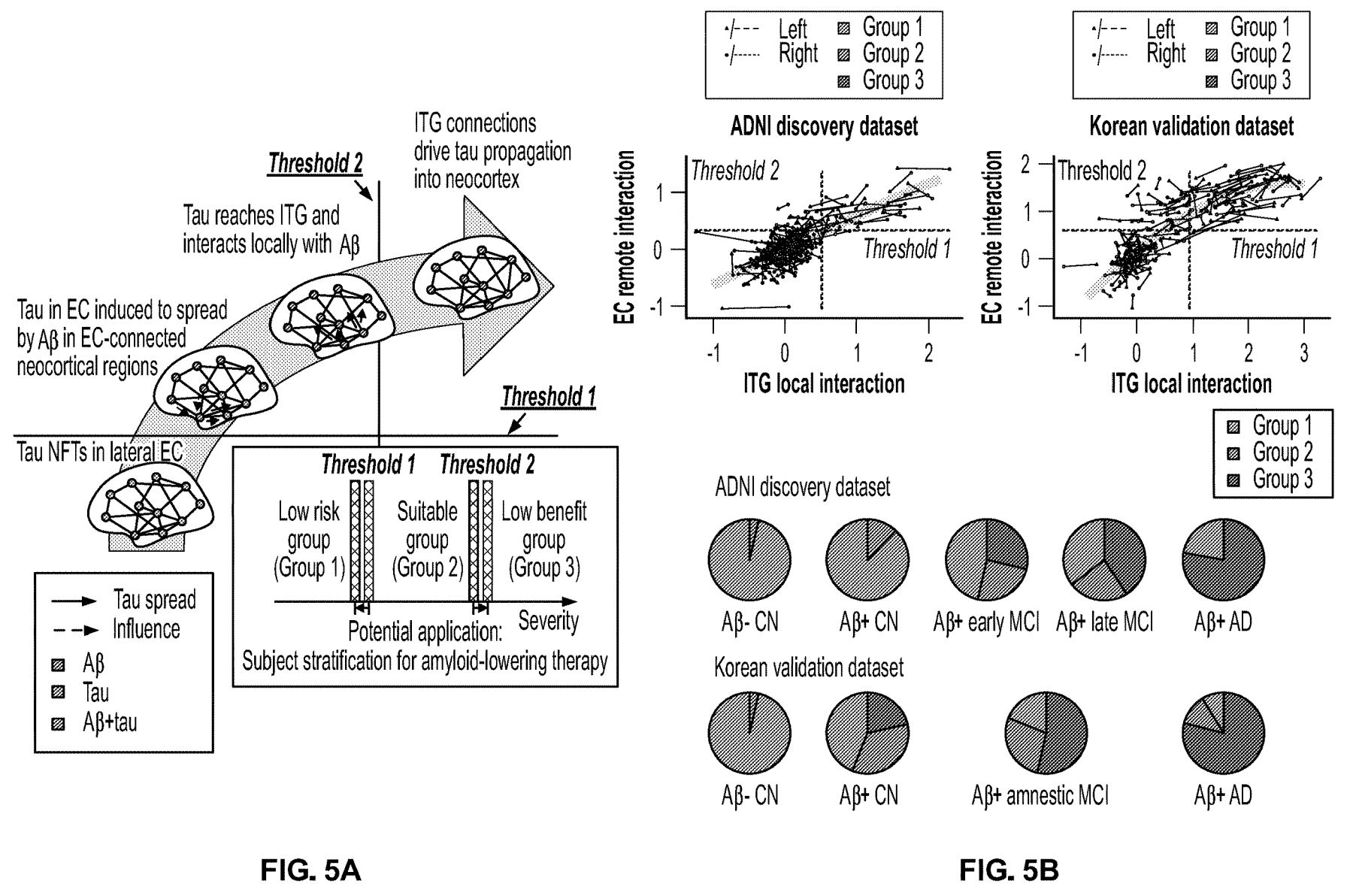

The findings outlined above suggest two pivotal moments in the molecular-anatomical pathogenesis of AD. The first occurs when neocortical Aβ emerges within multiple neocortical regions connected to the entorhinal cortices. This remote, connectionally mediated interaction between neocortical Aβ and entorhinal cortex tau may induce tau to further misfold and spread out of the entorhinal areas and into nearby, connected regions in the hippocampus, amygdala, and basal temporal cortices. The second pivotal moment occurs when tau neurofibrillary changes reach the ITG, where tau locally interacts with pre-existing Aβ to catalyze widespread tau propagation into other Aβ-positive and ITG-connected neocortical regions whose degeneration ultimately gives rise to dementia[53]. If these pivotal moments occur in sequence, as we hypothesize, then metrics capturing these two phenomena should obey a nonlinear relationship in which the EC remote Aβ-tau interaction rises first, before giving way to a rise in local Aβ-tau interaction within the ITG. Plotting these metrics across our discovery and validation cohorts strongly supported this prediction, demonstrating a fundamental arc of disease severity across individuals (FIG. 5A-B). Quadratic regression models based on the mean (left/right) values fit both datasets well (ADNI: $R^2$=0.71, Korean: $R^2$=0.70),[57] significantly better than did linear functions (ADNI: $R^2$=0.70/F (testing for the difference between quadratic and linear fit)=7.54, p=0.007; Korean: $R^2$=0.57/F=80.20, p=3e-16).

Figure 16:
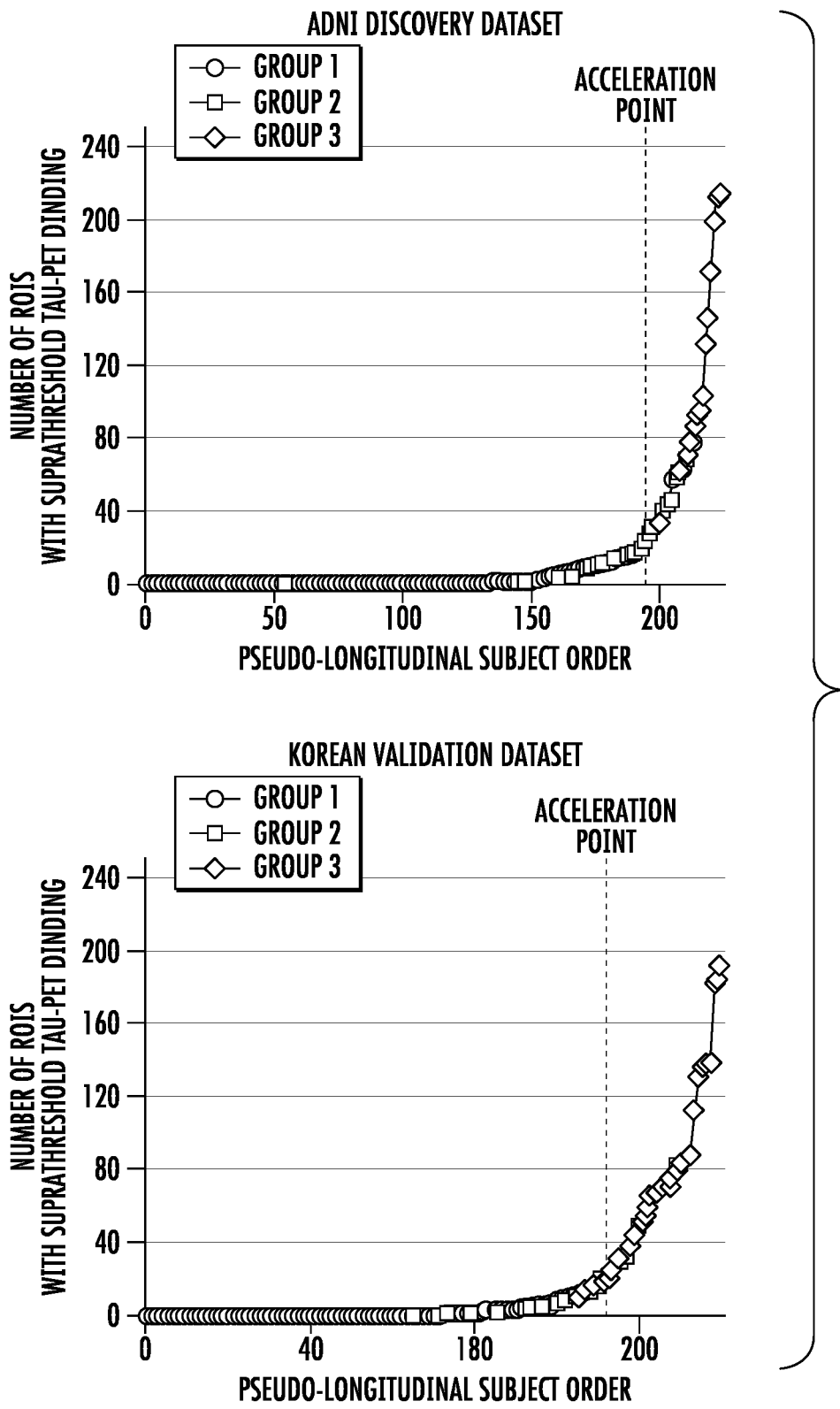
FIG. 16 depicts replication of tau regional spreading order
and acceleration phase topography in the Korean validation
dataset. ADNI data (left) are presented for comparison to the
findings, obtained using an identical procedure, from the
Korean validation dataset (right). The tau regional spreading
order showed high correspondence (Spearman ρ=0.70, and
there was strong overall topographical agreement between
datasets in the regions representing the three inferred phases.

Aβ-lowering strategies, such as anti-Aβ antibodies, are a widely pursued but as yet unsuccessful therapeutic strategy for AD. Moreover, patients treated with active Aβ immunization have shown evidence of continued tau spreading despite widespread Aβ plaque removal[58]. If the framework outlined above is correct, and if tau spreading becomes Aβ-independent once tau reaches the ITG propagation hubs, then Aβ-lowering therapies may require administration at or before the time tau reaches these ITG hubs. To operationalize this notion into a patient stratification method, we established quantitative thresholds for EC remote and ITG local Aβ-tau interactions (FIG. 5A, see Example 1) and used these thresholds to estimate each patient's suitability for an Aβ-lowering therapy. The rationale was that Aβ-lowering may prove most fruitful for patients who (1) have sufficient EC remote Aβ-tau interaction to induce tau spreading yet (2) have not developed enough ITG local Aβ-tau interaction to catalyze widespread neocortical tau propagation. Having systematically defined these thresholds, we added a uniform margin to each, lowering the low threshold and raising the high threshold to err toward including borderline individuals (FIG. 5A, see Example 1). Evaluating this approach across the entire AD clinical spectrum in both cohorts, we found that only around one quarter of patients with mild cognitive impairment (ADNI: 24.4%, Korean: 26.7%) and few patients with AD dementia (ADNI: 0.0%, Korean: 12.5%) fall within the therapeutic window for Aβ-lowering suggested by this model (FIG. 5B, see Table 10 below). These results were stable when generated using alternative tau-PET analysis methods (Table 6). Subjects falling within the therapeutic window (Group 2, FIG. 5) were positioned shortly before or occasionally just after the beginning of the tau acceleration phase identified from the pseudo-longitudinal subject order (see FIG. 16). Our model explicitly predicts that these subjects will show less severe tau-PET worsening, and therefore less clinical worsening, over time in the context of successful Aβ-lowering. This prediction can now be tested using data from previous, ongoing, and future Aβ-lowering clinical trials for which amyloid- and tau-PET data are available. Other AD therapeutic strategies may be well-suited to different points along the arc of AD progression. For example, Aβ prevention approaches, such as an anti-Aβ vaccine, may be best suited for individuals who have yet to develop remote Aβ-tau interactions in the EC (Group 1, FIG. 5), whereas Aβ-tau combination therapy may be required once local ITG Aβ-tau interaction has occurred and tau has begun to propagate beyond the ITG (Group 3, FIG. 5).

TABLE 10

| Example use case: subject stratification for amyloid-lowering clinical trials. | | | | | |
| --- | --- | --- | --- | --- | --- |
| ADNI discovery dataset | | | | | |
| Group | Aβ− CN (n = 115) | Aβ+ CN (n = 67) | Aβ+ early MCI (n = 28) | Aβ+ late MCI (n = 17) | Aβ+ AD (n = 9) |
| 1 | 111 (96.5) | 59 (88.1) | 13 (46.4) | 6 (35.3) | 2 (22.2) |
| 2 | 4 (3.5) | 8 (11.9) | 7 (25.0) | 4 (23.5) | 0 (0.0) |
| 3 | 0 (0.0) | 0 (0.0) | 8 (28.6) | 7 (41.2) | 7 (77.8) |
| Korean validation dataset | | | | | |
| Group | Aβ− CN (n = 87) | Aβ+ CN (n = 9) | Aβ+ amnestic MCI (n = 45) | | Aβ+ AD (n = 56) |
| 1 | 84 (96.6) | 4 (44.4) | 9 (20.0) | | 5 (8.9) |
| 2 | 3 (3.4) | 3 (33.3) | 12 (26.7) | | 7 (12.5) |
| 3 | 0 (0.0) | 2 (22.2) | 24 (53.3) | | 44 (78.6) |

Example 6. Supplementary Methods

Calculation of Goodness-of-Fit Scores

Figure 14:
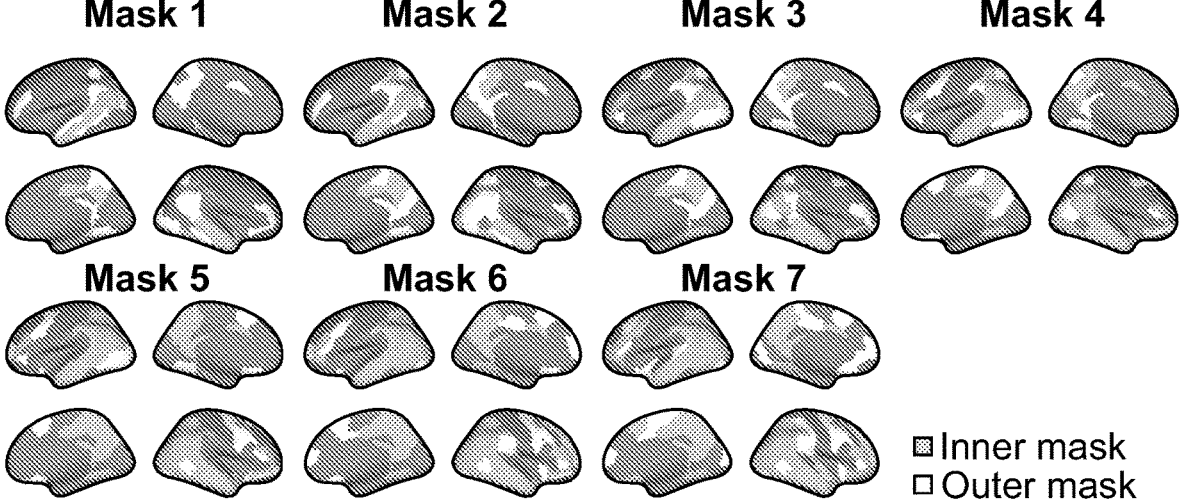
FIG. 14 depicts maps of seven inner-outer mask pairs
representing the tau acceleration phase. These mask pairs
were used to derive GOF scores for the network flow-based
connectivity maps derived from each seed region-of-inter-
est.

To identify the propagation hubs, we estimated the goodness-of-fit (GOF) of each region's network flow-based connectivity map to the progression of tau through the regions representing tau acceleration phase. We defined two binary masks, inner and outer, to indicate regions where tau may spread earlier and later, respectively. Assuming that the propagation hubs template the topography of acceleration phase tau spreading, the inner and outer mask regions were constrained to tau acceleration phase regions, arranged using the pseudo-longitudinal regional tau spreading order (see Example 1). At first, we assigned the first thirty brain regions to the inner mask and the next thirty regions to the outer mask. With a network flow-based connectivity map derived from each seed region using the healthy structural connectome, a GOF score was computed by subtracting an average connectivity to the outer mask area from an average connectivity to the inner mask area. For each seed region, the GOF scores were evaluated to identify regions with significant GOF scores using permutation-based one-sample t-test. We also applied other inner-outer mask pairs to mimic tau propagation and to avoid potential influence of arbitrary mask definition. We produced seven different mask sets increasing the size of the inner mask gradually by ten regions (or five regions for the validation dataset, which exhibited fewer acceleration phase regions) (see FIG. 14). For example, the second mask set had the first forty regions as the inner mask and the next thirty regions as the outer mask.

Statistical Analyses of Regional Interaction Score

We evaluated the statistical significance of interaction scores for each region. Four interaction types were examined: between $A\beta$ and tau (2-way; remote or local $A\beta$ influence) and between $A\beta$, PRNP, FYN, and tau (4-way; remote or local $A\beta$-PRNP influence). To address regional variations of $A\beta$-PET SUVRs without exaggeration of the effect, we first computed relative values of $A\beta$ or $A\beta$-PRNP influence using the respective thresholds derived from previous iterative outlier removal method[35]. The 95th percentile influence values were defined as cutoffs after removing outliers iteratively in $A\beta$-negative CN subjects. It was an identical criterion used for determination of remote/local $A\beta$-tau cutoffs for the interaction pseudo-order. The relative $A\beta$-related influence values were multiplied by each ROI's local tau W-score or local tau W-score×FYN expression level to obtain regional interaction scores. Each regional interaction score was compared to the median score of all regions within the respective hemisphere using permutation-based one-sample t-tests across all subjects. Multiple comparison corrections were conducted using the false discovery rate method[54] across each hemisphere's regions, and the significance level was set to $p<0.05$. According to our hypotheses and main results (see FIG. 4A), we assumed that the remote $A\beta$-tau interactions occur most rapidly in the entorhinal cortex and have a critical role to tau spreading from there, while local interactions occur early and crucially within the inferior temporal gyrus. Therefore, we examined the location of the entorhinal cortex on the distribution of t-statistics for remote 2-way or 4-way interaction scores and the inferior temporal gyrus on the distribution of t-statistics for local interaction scores (see FIG. 4 and FIG. 10).

REFERENCES

1 Leclerc, B., #xee & Abulrob, A. Perspectives in Molecular Imaging Using Staging Biomarkers and Immunotherapies in Alzheimer& #x2019;s Disease % J The Scientific World Journal. 2013, 16, doi:10.1155/2013/589308 (2013).

2 Jack, C. R. et al. Hypothetical model of dynamic biomarkers of the Alzheimer's pathological cascade. *The Lancet Neurology* 9, 119-128, doi:https://doi.org/10.1016/S1474-4422(09)70299-6 (2010).

3 Braak, H. & Braak, E. Neuropathological staging of Alzheimer-related changes. *Acta Neuropathologica* 82, 239-259 (1991).

4 Petersen, R. C. et al. Alzheimer& #039;s Disease Neuroimaging Initiative (ADNI). *Neurology* 74, 201, doi: 10.1212/WNL.0b013e3181cb3e25 (2010).

5 Albert, M. S. et al. The diagnosis of mild cognitive impairment due to Alzheimer's disease: Recommendations from the National Institute on Aging-Alzheimer's Association workgroups on diagnostic guidelines for Alzheimer's disease. *Alzheimer's & Dementia* 7, 270-279, doi:https://doi.org/10.1016/j.jalz.2011.03.008 (2011).

6 McKhann, G. M. et al. The diagnosis of dementia due to Alzheimer's disease: Recommendations from the National Institute on Aging-Alzheimer's Association workgroups on diagnostic guidelines for Alzheimer's disease. *Alzheimer's & Dementia* 7, 263-269, doi:https://doi.org/10.1016/j.jalz.2011.03.005 (2011).

7 Cho, H. et al. Progressive Tau Accumulation in Alzheimer Disease: 2-Year Follow-up Study. *J Nucl Med* 60, 1611-1621 (2019).

8 Das, S. R. et al. Longitudinal and cross-sectional structural magnetic resonance imaging correlates of AV-1451 uptake. *Neurobiology of Aging* 66, 49-58, doi:https://doi.org/10.1016/j.neurobiolaging.2018.01.024 (2018).

9 Maass, A. et al. Comparison of multiple tau-PET measures as biomarkers in aging and Alzheimer's disease. *NeuroImage* 157, 448-463, doi:https://doi.org/10.1016/j.neuroimage.2017.05.058 (2017).

10 Jagust, W. J. et al. The Alzheimer's Disease Neuroimaging Initiative 2 PET Core: 2015. *Alzheimers Dement* 11, 757-771, doi:10.1016/j.jalz.2015.05.001 (2015).

11 Fan, L. et al. The Human Brainnetome Atlas: A New Brain Atlas Based on Connectional Architecture. *Cerebral Cortex* 26, 3508-3526, doi:10.1093/cercor/bhw157 (2016).

12 Joshi, A. D. et al. Performance Characteristics of Amyloid PET with Florbetapir F 18 in Patients with Alzheimer's Disease and Cognitively Normal Subjects. 53, 378-384, doi:10.2967/jnumed.111.090340 (2012).

13 Choi, J. Y. et al. Off-Target 18F-AV-1451 Binding in the Basal Ganglia Correlates with Age-Related Iron Accumulation. *J Nucl Med* 59, 117-120 (2018).

14 Lemoine, L., Leuzy, A., Chiotis, K., Rodriguez-Vieitez, E. & Nordberg, A. Tau positron emission tomography imaging in tauopathies: The added hurdle of off-target binding. *Alzheimer's & Dementia: Diagnosis, Assessment & Disease Monitoring* 10, 232-236, doi:https://doi.org/10.1016/j.dadm.2018.01.007 (2018).

15 Lockhart, S. N. et al. Elevated <sup>18</sup>F-AV-1451 PET tracer uptake detected in incidental imaging findings. *Neurology* 88, 1095, doi:10.1212/WNL.0000000000003724 (2017).

16 Vogel, J. W. et al. Spread of pathological tau proteins through communicating neurons in human Alzheimer's disease. *Nat Commun* 11, 2612, doi:10.1038/s41467-020-15701-2 (2020).

17 Jack, C. R. et al. Medial temporal atrophy on MRI in normal aging and very mild Alzheimer's disease. *Neurology* 49, 786-794 (1997).

18 La Joie, R. et al. Region-specific hierarchy between atrophy, hypometabolism, and β-amyloid (Aβ) load in Alzheimer's disease dementia. *J Neurosci* 32, 16265-16273 (2012).

19 Ossenkoppele, R. et al. The behavioural/dysexecutive variant of Alzheimer's disease: clinical, neuroimaging and pathological features. *Brain* 138, 2732-2749 (2015).

20 Tsai, R. M. et al. 18F-flortaucipir (AV-1451) tau PET in frontotemporal dementia syndromes. *Alzheimers Res Ther* 11, 13, doi:10.1186/s13195-019-0470-7 (2019).

21 Wang, R., Benner, T., Sorensen, A. G. & Wedeen, V. J. in *Proc Intl Soc Mag Reson Med.* (Berlin).

22 van den Heuvel, M. P. & Sporns, O. Rich-Club Organization of the Human Connectome. *The Journal of Neuroscience* 31, 15775, doi:10.1523/JNEUROSCI.3539-11.2011 (2011).

23 Beaulieu, C. The basis of anisotropic water diffusion in the nervous system—a technical review. *NMR in Biomedicine* 15, 435-455, doi:10.1002/nbm.782 (2002).

24 Ewing-Cobbs, L., Hasan, K. M., Prasad, M. R., Kramer, L. & Bachevalier, J. Corpus callosum diffusion anisotropy correlates with neuropsychological outcomes in twins disconcordant for traumatic brain injury. *AJNR. American journal of neuroradiology* 27, 879-881 (2006).

25 Gold, B. T., Powell, D. K., Xuan, L., Jiang, Y. & Hardy, P. A. Speed of lexical decision correlates with diffusion anisotropy in left parietal and frontal white matter: evidence from diffusion tensor imaging. *Neuropsychologia* 45, 2439-2446, doi:10.1016/j.neuropsychologia.2007.04.011 (2007).

26 Cho, H. et al. In vivo cortical spreading pattern of tau and amyloid in the Alzheimer disease spectrum. *Annals of Neurology* 80, 247-258, doi:10.1002/ana.24711 (2016).

27 Wook Yoo, S. et al. A Network Flow-based Analysis of Cognitive Reserve in Normal Ageing and Alzheimer's Disease. *Scientific Reports* 5, 10057, doi:10.1038/srep10057 (2015).

28 Wilson, R. J. *Introduction to graph theory*. (Pearson Education India, 1979).

29 Brown, J. A. et al. Patient-Tailored, Connectivity-Based Forecasts of Spreading Brain Atrophy. *Neuron* 104, 856-868e855, doi:10.1016/j.neuron.2019.08.037 (2019).

30 Zhou, J., Gennatas, E. D., Kramer, J. H., Miller, B. L. & Seeley, W. W. Predicting regional neurodegeneration from the healthy brain functional connectome. *Neuron* 73, 1216-1227, doi:S0896-6273(12)00227-9 [pii]10.1016/j.neuron.2012.03.004 (2012).

31 Benjamini, Y. & Hochberg, Y. Controlling the False Discovery Rate: A Practical and Powerful Approach to Multiple Testing. *Journal of the Royal Statistical Society. Series B (Methodological)* 57, 289-300 (1995).

32 Iturria-Medina, Y., Sotero, R. C., Toussaint, P. J., Evans, A. C. & Alzheimer's Disease Neuroimaging, I. Epidemic spreading model to characterize misfolded proteins propagation in aging and associated neurodegenerative disorders. *PLoS computational biology* 10, e1003956-e1003956, doi:10.1371/journal.pcbi.1003956 (2014).

33 Waters, J. The concentration of soluble extracellular amyloid-p protein in acute brain slices from CRND8 mice. *PLoS one* 5, e15709-e15709, doi:10.1371/journal.pone.0015709 (2010).

34 Grothe, M. J. et al. In vivo staging of regional amyloid deposition. *Neurology* 89, 2031, doi:10.1212/WNL.0000000000004643 (2017).

35 Aizenstein, H. J. et al. Frequent Amyloid Deposition Without Significant Cognitive Impairment Among the Elderly. *Archives of Neurology* 65, 1509-1517, doi:10.1001/archneur.65.11.1509 (2008).

36 Corbett, G. T. et al. PrP is a central player in toxicity mediated by soluble aggregates of neurodegeneration-causing proteins. *Acta Neuropathologica*, doi:10.1007/s00401-019-02114-9 (2019).

37 Gomes, L. A. et al. Aβ-induced acceleration of Alzheimer-related r-pathology spreading and its association with prion protein. *Acta Neuropathologica* 138, 913-941, doi:10.1007/s00401-019-02053-5 (2019).

38 Brody, A. H. & Strittmatter, S. M. Synaptotoxic Signaling by Amyloid Beta Oligomers in Alzheimer's Disease Through Prion Protein and mGluR5. *Adv Pharmacol* 82, 293-323, doi:10.1016/bs.apha.2017.09.007 (2018).

39 Hawrylycz, M. J. et al. An anatomically comprehensive atlas of the adult human brain transcriptome. *Nature* 489, 391-399, doi:10.1038/nature11405 (2012).

40 Arnatkeviciute, A., Fulcher, B. D. & Fornito, A. A practical guide to linking brain-wide gene expression and neuroimaging data. *NeuroImage* 189, 353-367, doi:https://doi.org/10.1016/j.neuroimage.2019.01.011 (2019).

41 Arloth, J., Bader, D. M., Roh, S. & Altmann, A. Re-Annotator: Annotation Pipeline for Microarray Probe Sequences. *PloS one* 10, e0139516-e0139516, doi:10.1371/journal.pone.0139516 (2015).

42 Burt, J. B. et al. Hierarchy of transcriptomic specialization across human cortex captured by structural neuroimaging topography. *Nature Neuroscience* 21, 1251-1259, doi:10.1038/s41593-018-0195-0 (2018).

43 Hawrylycz, M. et al. Canonical genetic signatures of the adult human brain. *Nature Neuroscience* 18, 1832-1844, doi:10.1038/nn.4171 (2015).

44 Fulcher, B. D., Little, M. A. & Jones, N. S. Highly comparative time-series analysis: the empirical structure of time series and their methods. 10, 20130048, doi:doi:10.1098/rsif.2013.0048 (2013).

45 McDade, E. et al. Longitudinal cognitive and biomarker changes in dominantly inherited Alzheimer disease. *Neurology* 91, e1295-e1306, doi:10.1212/WNL.0000000000006277 (2018).

46 Braak, H. & Del Tredici, K. Alzheimer's pathogenesis: is there neuron-to-neuron propagation? *Acta Neuropathologica* 121, 589-595, doi:10.1007/s00401-011-0825-z (2011).

47 Kim, E. J. et al. Evidence of corticofugal tau spreading in patients with frontotemporal dementia. *Acta Neuropathol*, doi:10.1007/s00401-019-02075-z (2019).

48 Raj, A. et al. Network Diffusion Model of Progression Predicts Longitudinal Patterns of Atrophy and Metabolism in Alzheimer's Disease. *Cell reports*, doi:10.1016/j.celrep.2014.12.034 (2015).

49 Liu, L. et al. Trans-synaptic spread of tau pathology in vivo. *PLoS One* 7, e31302, doi:10.1371/journal.pone.0031302 (2012).

50 Clavaguera, F. et al. Brain homogenates from human tauopathies induce tau inclusions in mouse brain. *Proc Natl Acad Sci USA* 110, 9535-9540, doi:10.1073/pnas.1301175110 (2013).

51 Raj, A., Kuceyeski, A. & Weiner, M. A network diffusion model of disease progression in dementia. *Neuron* 73, 1204-1215, doi:S0896-6273(12)00135-3 [pii]10.1016/j.neuron.2011.12.040 (2012).

52 Ossenkoppele, R. et al. Tau covariance patterns in Alzheimer's disease patients match intrinsic connectivity networks in the healthy brain. *NeuroImage. Clinical* 23, 101848, doi:10.1016/j.nicl.2019.101848 (2019).

53 Sepulcre, J. et al. Neurogenetic contributions to amyloid beta and tau spreading in the human cortex. *Nat Med* 24, 1910-1918, doi:10.1038/s41591-018-0206-4 (2018).

54 Benjamini, Y. & Hochberg, Y. Controlling the False Discovery Rate: A Practical and Powerful Approach to Multiple Testing. *Journal of the Royal Statistical Society: Series B (Methodological)* 57, 289-300, doi:10.1111/j.2517-6161.1995.tb02031.x (1995).

55 Musiek, E. S. & Holtzman, D. M. Origins of Alzheimer's disease: reconciling cerebrospinal fluid biomarker and neuropathology data regarding the temporal sequence of amyloid-beta and tau involvement. *Current Opinion in Neurology* 25, 715-720, doi:10.1097/WCO.0b013e32835a30f4 (2012).

56 He, Z. et al. Amyloid-beta plaques enhance Alzheimer's brain tau-seeded pathologies by facilitating neuritic plaque tau aggregation. *Nat Med* 24, 29-38, doi:10.1038/nm.4443 (2018).

57 Indrayan, A. & Malhotra, R. K. *Medical biostatistics.* (CRC Press, 2017).

58 Nicoll, J. A. R. et al. Persistent neuropathological effects 14 years following amyloid-beta immunization in Alzheimer's disease. *Brain* 142, 2113-2126, doi:10.1093/brain/awz142 (2019).

The invention claimed is:

1. A method of identifying a subject likely to respond to an Alzheimer's disease (AD) treatment, the method comprising:
   (a) segmenting an image of a brain of the subject into one or a plurality of regions;
   (b) analyzing an amount of amyloid-beta (Aβ) protein deposition in a first region of the one or a plurality of regions within the brain of the subject;
   (c) analyzing an amount of tau protein deposition in the first region within the brain of the subject;
   (d) comparing the relative quantities of Aβ protein deposition and tau protein deposition by
      (i) determining the relative quantities of Aβ protein deposition versus tau protein deposition in the first region of the brain; and
      (ii) calculating a first normalized score corresponding to a degree of interaction between tau-positive neural tissue and Aβ-positive neural tissue based upon Aβ protein deposition and tau protein deposition in the first region of the brain.

2. A method of identifying a subject responsive to an Alzheimer's disease (AD) treatment comprising:
   (a) segmenting an image of a brain of the subject into a plurality of regions;
   (b) analyzing an amount of amyloid-beta (Aβ) protein deposition in a first region of the plurality of regions and a second region of the plurality of regions within the brain of the subject;
   (c) analyzing an amount of tau protein deposition in the first region and the second region within the brain of the subject; and
   (d) comparing the relative quantities of Aβ protein deposition and tau protein deposition by
      (i) determining the relative quantities of Aβ protein deposition versus tau protein deposition in the first region of the brain and determining the relative quantities of Aβ protein deposition versus tau protein deposition in the second region of the brain; and
      (ii) calculating a first normalized score corresponding to a degree of interaction between tau-positive neural tissue and Aβ-positive neural tissue based upon Aβ protein deposition and tau protein deposition in the first region of the brain, and calculating a second normalized score corresponding to interaction of Aβ protein deposition and tau protein deposition in the second region of the brain of the subject.

3. The method of claim 2, wherein the step of imaging the brain is performed through a positron emission tomography (PET) scan.

4. A method of predicting a likelihood of a subject or population of subjects does or does not respond to an Aβ modulating agent comprising:

(a) segmenting an image of a brain of the subject into a plurality of regions;
   (b) analyzing an amount of amyloid-beta (Aβ) protein deposition in a first region of the plurality of regions and a second region of the plurality of regions within the brain of the subject;
   (c) analyzing an amount of tau protein deposition in the first region and the second region within the brain of the subject; and
   (d) comparing the relative quantities of Aβ protein deposition and tau protein deposition in the first and second region by
      (i) determining the relative quantities of Aβ protein deposition versus tau protein deposition in the first region of the brain and determining the relative quantities of Aβ protein deposition versus tau protein deposition in the second region of the brain; and
      (ii) calculating a first normalized score corresponding to a degree of interaction between tau-positive neural tissue and Aβ-positive neural tissue based upon Aβ protein deposition and tau protein deposition in the first region of the brain, and calculating a second normalized score corresponding to interaction of Aβ protein deposition and tau protein deposition in the second region of the brain of the subject.

5. The method of claim 4 further comprising:
   (e) comparing the first normalized score to a first threshold and comparing a second normalized score to a second threshold; and
   (f) classifying the subject as being likely to respond to Aβ modulating agent based upon results of comparing of step (e) relative to the first and/or second threshold, wherein each of steps (e) and (f) are performed after step (d), and wherein the first threshold is calculated relative to a first control dataset and the second threshold is calculated relative to a second control.

6. A method of predicting a pathological prognosis and/or a clinical outcome of a subject or population of subjects suffering from Alzheimer's disease comprising:
   (a) segmenting an image of a brain of the subject into a plurality of regions;
   (b) analyzing an amount of amyloid-beta (Aβ) protein deposition in a first region of the plurality of regions and a second region of the plurality of regions within the brain of the subject;
   (c) analyzing an amount of tau protein deposition in the firs region and the second region within the brain of the subject; and
   (d) comparing the relative quantities of Aβ protein deposition and tau protein deposition by
      (i) determining the relative quantities of Aβ protein deposition versus tau protein deposition in the at first region of the brain and determining the relative quantities of Aβ protein deposition versus tau protein deposition in the second region of the brain; and (ii) calculating a first normalized score corresponding a degree of interaction between tau-positive neural tissue and Aβ-positive neural tissue based upon Aβ protein deposition and tau protein deposition in the first region of the brain, and calculating a second normalized score corresponding to a degree of interaction between tau-positive neural tissue and Aβ-positive neural tissue based upon Aβ protein deposition and tau protein deposition in the second region of the brain of the subject.

7. A method of selecting or optimizing an AD therapy of a disease or disorder in a subject or population of subjects, the method comprising:
   (a) segmenting an image of a brain of the subject into a plurality of regions;
   (b) analyzing an amount of amyloid-beta (Aβ) protein deposition in a first region of the plurality of regions and a second region of the plurality of regions within the brain of the subject;
   (c) analyzing an amount of tau protein deposition in a first region of the plurality of regions and a second region of the plurality of regions within the brain of the subject; and
   (d) comparing the relative quantities of Aβ protein deposition and tau protein deposition by
      (i) determining the relative quantities of Aβ protein deposition versus tau protein deposition in the at least one region of the brain;
      (ii) calculating a first normalized score corresponding to a degree of interaction between tau-positive neural tissue and Aβ-positive neural tissue based upon Aβ protein deposition and tau protein deposition in the first region of the brain, and calculating a second normalized score corresponding to a degree of interaction between tau-positive neural tissue and Aβ-positive neural tissue based upon Aβ protein deposition and tau protein deposition in the second region of the brain of the subject.

8. A computer program product encoded on a computer-readable storage medium comprising instructions for:
   (a) segmenting an image of a brain of the subject into one or a plurality of regions;
   (b) analyzing an amount of amyloid-beta (Aβ) protein deposition in a first region of the one or a plurality of regions within the brain of the subject;
   (c) analyzing an amount of tau protein deposition in the first region within the brain of the subject; and
   (d) comparing the relative quantities of Aβ protein deposition and tau protein deposition by
      (i) determining the relative quantities of Aβ protein deposition versus tau protein deposition in the first region of the brain;
      (ii) calculating a first normalized score corresponding to a degree of interaction between tau-positive neural tissue and Aβ-positive neural tissue based upon Aβ protein deposition and tau protein deposition in the first region of the brain.

9. A system comprising:
   (i) the computer program product of claim 8; and
   (ii) a processor operable to execute programs; and/or a memory associated with the processor.

10. A system for identifying a protein interaction network in a subject or population of subjects comprising:
   a processor operable to execute programs;
   a memory associated with the processor;
   a database associated with said processor and said memory;

a program stored in the memory and executable by the processor, the program being operable for:
   (a) segmenting an image of a brain of the subject into one or a plurality of regions;
   (b) analyzing amyloid-beta (Aβ) protein deposition in a first region of the one or a plurality of regions within the brain of the subject;
   (c) analyzing tau protein deposition in the first region within the brain of the subject; and
   (d) comparing the relative quantities of Aβ protein deposition and tau protein deposition by
      (i) determining the relative quantities of Aβ protein deposition versus tau protein deposition in the at least one region of the brain;
      (ii) calculating a first normalized score corresponding to a degree of interaction between tau-positive neural tissue and Aβ-positive neural tissue based upon Aβ protein deposition and tau protein deposition in the first region of the brain.

11. The method of claim 1 further comprising (e) classifying the subject as a responder to AD treatment based upon the first normalized score.

12. The method of claim 1, wherein the step of imaging the brain is performed through a positron emission tomography (PET) scan.

13. The method of claim 1, wherein calculating the first normalized score comprises calculating a likelihood of tau-positive neural tissue in an entorhinal cortex (ERC) region of the brain of the subject interacting with Aβ-positive neural tissue in a non-ERC region of the brain.

14. The method of claim 1, wherein step (b) further comprises analyzing an amount of amyloid-beta (Aβ) protein deposition in at least one second region within the brain of the subject, step (c) further comprises analyzing an amount of tau protein deposition in the at least one second region within the brain of the subject, step (d)(i) further comprises determining the relative quantities of Aβ protein deposition versus tau protein deposition in the at least one second region of the brain, and step (d)(ii) further comprises calculating a second normalized score corresponding a degree of interaction between tau-positive neural tissue and Aβ-positive neural tissue based upon Aβ protein deposition and tau protein deposition in the at least one second region of the brain of the subject.

15. The method of claim 14 further comprising:
   (e) comparing the first normalized score to a first threshold and comparing a second normalized score to a second threshold; and
   (f) classifying the subject as being likely to respond to an AD treatment based upon results of comparing of step (e) relative to the first and/or second threshold, wherein each of steps (e) and (f) are performed after step (d), and wherein the first threshold is calculated relative to a first control dataset and the second threshold is calculated relative to a second control dataset.

16. The method of claim 15, wherein calculating the first normalized score comprises calculating a likelihood of tau-positive neural tissue in an entorhinal cortex (ERC) region of the brain of the subject interacting with Aβ-positive neural tissue in a non-ERC region of the brain and calculating the second normalized score comprises calculating a likelihood of tau-positive neural tissue interacting with Aβ-positive neural tissue locally within left and/or right inferior temporal gyri (ITG) of the brain.

17. The method of claim 16, wherein the first threshold is from about 1 to about 10 in each cerebral hemisphere and is determined by the following formula:

$$a_1 \times b_1$$

wherein $a_1$ is a regional cutoff value of remote Aβ influence metric at the ERC region calculated by iteratively removing outliers within the ERC region's data from the control population until no outlier arises and multiplies the maximum of remaining values by a small number as a buffer, values higher than about 1.5×the interquartile range over the third quartile are considered as outliers, and about the $95^{th}$ percentile value of the remaining data after removing outliers being identified as the regional cutoff value of remote Aβ influence metric at the ERC region, and wherein $b_1$ is a tau W-score threshold of about 2.5; and/or wherein the second threshold is from about 1 to about 10 in each cerebral hemisphere and is determined by the following formula:

$$a_2 \times b_2$$

wherein $a_2$ is a regional cutoff value of local Aβ deposition value at the ITG region calculated by iteratively removing outliers within the ITG region's data from the control population until no outlier arises and multiplies the maximum of remaining values by a small number as a buffer, values higher than about 1.5×the interquartile range over the third quartile are considered as outliers, and about the $95^{th}$ percentile value of the remaining data after removing outliers being identified as the regional cutoff value of local Aβ deposition value at the ITG region, and wherein $b_2$ is a tau W-score threshold of about 2.5.

18. The method of claim 14, wherein calculating the first normalized score comprises comparing the interaction of tau protein deposition in the at least one first region of interest of the brain as compared to Aβ protein deposition in one or a plurality of regions of the brain outside of the first region of interest and calculating the second normalized score comprises comparing Aβ protein deposition and tau protein deposition in the at least one second region of interest of the brain of the subject.

19. The method of claim 18, wherein the first normalized score is calculated by the following formula:

$$(\Sigma_j \delta_{ij} \cdot A\beta \ SUVR_j) \times (Tau \ W\text{-}score_i)$$

wherein $\Sigma_j \delta_{ij}$ is the structural or functional connectivity between the at least one first region of interest, region i, and the one or plurality of regions, denoted here as region(s) j, of the brain outside of the at least one first region of interest; wherein $SUVR_j$ is a first standardized uptake value ratio (SUVR) corresponding to the Aβ protein deposition in the one or plurality of regions, denoted here as region(s) j, of the brain outside of the at least one first region of interest, wherein Tau $W\text{-}score_i$ is a first standardized value corresponding to the tau protein deposition in the at least one first region of interest of the brain, the first standardized value being calculated based on a control population of subjects, wherein the second normalized score is calculated by the following formula:

$$(A\beta \ SUVR_k) \times (Tau \ W\text{-}score_k)$$

wherein $SUVR_k$ is a second SUVR corresponding to the Aβ protein deposition in the at least one second region of interest of the brain, denoted here as region k, and wherein Tau $W\text{-}score_k$ is a second standardized value corresponding to the tau protein deposition in the at least one second region of interest of the brain, denoted here as k, the second standardized value being calculated based on the control population of subjects.

20. The method of claim 15, wherein comparing the Aβ protein deposition and/or the tau protein deposition comprises quantifying a relative amount of Aβ protein deposition within left and/or right inferior temporal gyri (ITG) and quantifying a relative amount of tau protein deposition within left and/or right ITG.

21. The method of claim 14, wherein calculating the second normalized score comprises calculating a likelihood of tau-positive neural tissue interacting with Aβ-positive neural tissue locally within left and/or right inferior temporal gyri (ITG) of the brain of the subject.

22. The method of claim 21, wherein a subject is identified as being likely to respond to an Aβ modulating treatment as the AD treatment if the normalized first and second scores of step (d) comprise a high degree of interactions between ERC neural tissue with tau protein deposition and non-ERC neural tissue with Aβ protein deposition and a low degree of local interactions between tau protein deposition and Aβ protein deposition within the ITG.

* * * * *

SEQUENCE LISTING

<160> NUMBER OF SEQ ID NOS: 2

<210> SEQ ID NO 1
<211> LENGTH: 770
<212> TYPE: PRT
<213> ORGANISM: Homo sapiens

<400> SEQUENCE: 1

```
Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
```

-continued

```
              275                    280                    285
Glu Val Cys Ser Glu Gln Ala Glu Thr Gly Pro Cys Arg Ala Met Ile
    290                    295                    300

Ser Arg Trp Tyr Phe Asp Val Thr Glu Gly Lys Cys Ala Pro Phe Phe
305                    310                    315                    320

Tyr Gly Gly Cys Gly Gly Asn Arg Asn Asn Phe Asp Thr Glu Glu Tyr
                325                    330                    335

Cys Met Ala Val Cys Gly Ser Ala Met Ser Gln Ser Leu Leu Lys Thr
            340                    345                    350

Thr Gln Glu Pro Leu Ala Arg Asp Pro Val Lys Leu Pro Thr Thr Ala
        355                    360                    365

Ala Ser Thr Pro Asp Ala Val Asp Lys Tyr Leu Glu Thr Pro Gly Asp
    370                    375                    380

Glu Asn Glu His Ala His Phe Gln Lys Ala Lys Glu Arg Leu Glu Ala
385                    390                    395                    400

Lys His Arg Glu Arg Met Ser Gln Val Met Arg Glu Trp Glu Glu Ala
                405                    410                    415

Glu Arg Gln Ala Lys Asn Leu Pro Lys Ala Asp Lys Lys Ala Val Ile
            420                    425                    430

Gln His Phe Gln Glu Lys Val Glu Ser Leu Glu Gln Glu Ala Ala Asn
        435                    440                    445

Glu Arg Gln Gln Leu Val Glu Thr His Met Ala Arg Val Glu Ala Met
    450                    455                    460

Leu Asn Asp Arg Arg Arg Leu Ala Leu Glu Asn Tyr Ile Thr Ala Leu
465                    470                    475                    480

Gln Ala Val Pro Pro Arg Pro Arg His Val Phe Asn Met Leu Lys Lys
                485                    490                    495

Tyr Val Arg Ala Glu Gln Lys Asp Arg Gln His Thr Leu Lys His Phe
            500                    505                    510

Glu His Val Arg Met Val Asp Pro Lys Lys Ala Ala Gln Ile Arg Ser
        515                    520                    525

Gln Val Met Thr His Leu Arg Val Ile Tyr Glu Arg Met Asn Gln Ser
    530                    535                    540

Leu Ser Leu Leu Tyr Asn Val Pro Ala Val Ala Glu Glu Ile Gln Asp
545                    550                    555                    560

Glu Val Asp Glu Leu Leu Gln Lys Glu Gln Asn Tyr Ser Asp Asp Val
                565                    570                    575

Leu Ala Asn Met Ile Ser Glu Pro Arg Ile Ser Tyr Gly Asn Asp Ala
            580                    585                    590

Leu Met Pro Ser Leu Thr Glu Thr Lys Thr Thr Val Glu Leu Leu Pro
        595                    600                    605

Val Asn Gly Glu Phe Ser Leu Asp Asp Leu Gln Pro Trp His Ser Phe
    610                    615                    620

Gly Ala Asp Ser Val Pro Ala Asn Thr Glu Asn Glu Val Glu Pro Val
625                    630                    635                    640

Asp Ala Arg Pro Ala Ala Asp Arg Gly Leu Thr Thr Arg Pro Gly Ser
                645                    650                    655

Gly Leu Thr Asn Ile Lys Thr Glu Glu Ile Ser Glu Val Lys Met Asp
            660                    665                    670

Ala Glu Phe Arg His Asp Ser Gly Tyr Glu Val His His Gln Lys Leu
        675                    680                    685

Val Phe Phe Ala Glu Asp Val Gly Ser Asn Lys Gly Ala Ile Ile Gly
    690                    695                    700
```

-continued

```
Leu Met Val Gly Gly Val Val Ile Ala Thr Val Ile Val Ile Thr Leu
705             710             715             720

Val Met Leu Lys Lys Lys Gln Tyr Thr Ser Ile His His Gly Val Val
        725             730             735

Glu Val Asp Ala Ala Val Thr Pro Glu Glu Arg His Leu Ser Lys Met
        740             745             750

Gln Gln Asn Gly Tyr Glu Asn Pro Thr Tyr Lys Phe Phe Glu Gln Met
        755             760             765

Gln Asn
    770

<210> SEQ ID NO 2
<211> LENGTH: 758
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5               10              15

Thr Tyr Gly Leu Gly Asp Arg Lys Asp Gln Gly Gly Tyr Thr Met His
            20              25              30

Gln Asp Gln Glu Gly Asp Thr Asp Ala Gly Leu Lys Glu Ser Pro Leu
        35              40              45

Gln Thr Pro Thr Glu Asp Gly Ser Glu Glu Pro Gly Ser Glu Thr Ser
    50              55              60

Asp Ala Lys Ser Thr Pro Thr Ala Glu Asp Val Thr Ala Pro Leu Val
65              70              75              80

Asp Glu Gly Ala Pro Gly Lys Gln Ala Ala Ala Gln Pro His Thr Glu
            85              90              95

Ile Pro Glu Gly Thr Thr Ala Glu Glu Ala Gly Ile Gly Asp Thr Pro
            100             105             110

Ser Leu Glu Asp Glu Ala Ala Gly His Val Thr Gln Glu Pro Glu Ser
        115             120             125

Gly Lys Val Val Gln Glu Gly Phe Leu Arg Glu Pro Gly Pro Pro Gly
    130             135             140

Leu Ser His Gln Leu Met Ser Gly Met Pro Gly Ala Pro Leu Leu Pro
145             150             155             160

Glu Gly Pro Arg Glu Ala Thr Arg Gln Pro Ser Gly Thr Gly Pro Glu
            165             170             175

Asp Thr Glu Gly Gly Arg His Ala Pro Glu Leu Leu Lys His Gln Leu
            180             185             190

Leu Gly Asp Leu His Gln Glu Gly Pro Pro Leu Lys Gly Ala Gly Gly
        195             200             205

Lys Glu Arg Pro Gly Ser Lys Glu Glu Val Asp Glu Asp Arg Asp Val
    210             215             220

Asp Glu Ser Ser Pro Gln Asp Ser Pro Pro Ser Lys Ala Ser Pro Ala
225             230             235             240

Gln Asp Gly Arg Pro Pro Gln Thr Ala Ala Arg Glu Ala Thr Ser Ile
            245             250             255

Pro Gly Phe Pro Ala Glu Gly Ala Ile Pro Leu Pro Val Asp Phe Leu
            260             265             270

Ser Lys Val Ser Thr Glu Ile Pro Ala Ser Glu Pro Asp Gly Pro Ser
        275             280             285

Val Gly Arg Ala Lys Gly Gln Asp Ala Pro Leu Glu Phe Thr Phe His
```

-continued

```
           290                   295                   300

Val Glu Ile Thr Pro Asn Val Gln Lys Glu Gln Ala His Ser Glu Glu
305                   310                   315                   320

His Leu Gly Arg Ala Ala Phe Pro Gly Ala Pro Gly Glu Gly Pro Glu
                  325                   330                   335

Ala Arg Gly Pro Ser Leu Gly Glu Asp Thr Lys Glu Ala Asp Leu Pro
                  340                   345                   350

Glu Pro Ser Glu Lys Gln Pro Ala Ala Ala Pro Arg Gly Lys Pro Val
                  355                   360                   365

Ser Arg Val Pro Gln Leu Lys Ala Arg Met Val Ser Lys Ser Lys Asp
                  370                   375                   380

Gly Thr Gly Ser Asp Asp Lys Lys Ala Lys Thr Ser Thr Arg Ser Ser
385                   390                   395                   400

Ala Lys Thr Leu Lys Asn Arg Pro Cys Leu Ser Pro Lys His Pro Thr
                  405                   410                   415

Pro Gly Ser Ser Asp Pro Leu Ile Gln Pro Ser Ser Pro Ala Val Cys
                  420                   425                   430

Pro Glu Pro Pro Ser Ser Pro Lys Tyr Val Ser Ser Val Thr Ser Arg
                  435                   440                   445

Thr Gly Ser Ser Gly Ala Lys Glu Met Lys Leu Lys Gly Ala Asp Gly
                  450                   455                   460

Lys Thr Lys Ile Ala Thr Pro Arg Gly Ala Ala Pro Pro Gly Gln Lys
465                   470                   475                   480

Gly Gln Ala Asn Ala Thr Arg Ile Pro Ala Lys Thr Pro Pro Ala Pro
                  485                   490                   495

Lys Thr Pro Pro Ser Ser Gly Glu Pro Pro Lys Ser Gly Asp Arg Ser
                  500                   505                   510

Gly Tyr Ser Ser Pro Gly Ser Pro Gly Thr Pro Gly Ser Arg Ser Arg
                  515                   520                   525

Thr Pro Ser Leu Pro Thr Pro Pro Thr Arg Glu Pro Lys Lys Val Ala
                  530                   535                   540

Val Val Arg Thr Pro Pro Lys Ser Pro Ser Ser Ala Lys Ser Arg Leu
545                   550                   555                   560

Gln Thr Ala Pro Val Pro Met Pro Asp Leu Lys Asn Val Lys Ser Lys
                  565                   570                   575

Ile Gly Ser Thr Glu Asn Leu Lys His Gln Pro Gly Gly Gly Lys Val
                  580                   585                   590

Gln Ile Ile Asn Lys Lys Leu Asp Leu Ser Asn Val Gln Ser Lys Cys
                  595                   600                   605

Gly Ser Lys Asp Asn Ile Lys His Val Pro Gly Gly Gly Ser Val Gln
                  610                   615                   620

Ile Val Tyr Lys Pro Val Asp Leu Ser Lys Val Thr Ser Lys Cys Gly
625                   630                   635                   640

Ser Leu Gly Asn Ile His His Lys Pro Gly Gly Gly Gln Val Glu Val
                  645                   650                   655

Lys Ser Glu Lys Leu Asp Phe Lys Asp Arg Val Gln Ser Lys Ile Gly
                  660                   665                   670

Ser Leu Asp Asn Ile Thr His Val Pro Gly Gly Gly Asn Lys Lys Ile
                  675                   680                   685

Glu Thr His Lys Leu Thr Phe Arg Glu Asn Ala Lys Ala Lys Thr Asp
                  690                   695                   700

His Gly Ala Glu Ile Val Tyr Lys Ser Pro Val Val Ser Gly Asp Thr
705                   710                   715                   720
```

-continued

```
Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
        755
```